(12) United States Patent
Gardner et al.

(10) Patent No.: US 8,309,537 B2
(45) Date of Patent: Nov. 13, 2012

(54) COMPOSITIONS AND METHODS FOR TREATING COLITIS

(75) Inventors: Joseph H. Gardner, Cincinnati, OH (US); Robert Shalwitz, Bexley, OH (US)

(73) Assignee: Aerpio Therapeutics Inc., Cincinnati, OH (US)

( * ) Notice: Subject to any disclaimer, the term of this patent is extended or adjusted under 35 U.S.C. 154(b) by 187 days.

(21) Appl. No.: 12/940,901

(22) Filed: Nov. 5, 2010

(65) Prior Publication Data

US 2011/0112055 A1 May 12, 2011

Related U.S. Application Data

(60) Provisional application No. 61/258,914, filed on Nov. 6, 2009, provisional application No. 61/258,918, filed on Nov. 6, 2009.

(51) Int. Cl.
*A61K 31/444* (2006.01)
*A61K 31/4439* (2006.01)
*A61K 31/4545* (2006.01)
*A61K 31/496* (2006.01)
*A61K 31/505* (2006.01)
*A61K 31/5377* (2006.01)
*A61K 31/541* (2006.01)
*A61K 31/55* (2006.01)

(52) U.S. Cl. ............... 514/110; 514/252.02; 514/253.12; 514/316; 514/318; 514/341; 514/342

(58) Field of Classification Search ............... 514/110, 514/252.02, 253.12, 316, 318, 333, 341, 514/342
See application file for complete search history.

(56) References Cited

U.S. PATENT DOCUMENTS

| | | |
|---|---|---|
| 3,853,900 A | 12/1974 | Shone et al. |
| 3,894,920 A | 7/1975 | Kondo et al. |
| 5,358,949 A | 10/1994 | Tabusa et al. |
| 5,397,799 A | 3/1995 | Kress et al. |
| 5,407,948 A | 4/1995 | Fey et al. |
| 5,620,995 A | 4/1997 | Weidemann et al. |
| 5,849,587 A | 12/1998 | Hanauske-Abel et al. |
| 6,020,350 A | 2/2000 | Weidemann et al. |
| 6,046,219 A | 4/2000 | Hanauske-Abel et al. |
| 6,080,766 A | 6/2000 | Hanauske-Abel et al. |
| 6,566,088 B1 | 5/2003 | Knight et al. |
| 6,589,758 B1 | 7/2003 | Zhu |
| 6,930,117 B2 | 8/2005 | Warshakoon et al. |
| 6,946,479 B2 | 9/2005 | Warshakoon et al. |
| 7,183,287 B2 | 2/2007 | Durley |
| 7,247,632 B2 | 7/2007 | Warshokoon et al. |
| 7,247,648 B2 | 7/2007 | Warshokoon et al. |
| 7,588,924 B2 | 9/2009 | Evdokimov et al. |
| 7,790,748 B2 | 9/2010 | Warshakoon et al. |
| 7,811,595 B2 | 10/2010 | Kawamoto et al. |
| 2002/0192737 A1 | 12/2002 | Kaelin, Jr. et al. |
| 2003/0153503 A1 | 8/2003 | Klaus et al. |
| 2003/0176317 A1 | 9/2003 | Guenzler-Pukall et al. |
| 2004/0146964 A1 | 7/2004 | Maxwell et al. |
| 2004/0254215 A1 | 12/2004 | Arend et al. |
| 2006/0276477 A1 | 12/2006 | Klaus et al. |
| 2007/0154482 A1 | 7/2007 | Sukhatme et al. |
| 2007/0213335 A1 | 9/2007 | Fitch et al. |
| 2007/0249550 A1 | 10/2007 | Sitkovsky |
| 2007/0270407 A1 | 11/2007 | Warshakoon et al. |
| 2007/0299086 A1 | 12/2007 | Kawamoto et al. |
| 2008/0124740 A1 | 5/2008 | Evdokimov et al. |
| 2008/0213404 A1 | 9/2008 | Johnson et al. |
| 2008/0300262 A1 | 12/2008 | Snutch |
| 2009/0082357 A1 | 3/2009 | Fitch et al. |
| 2009/0093483 A1 | 4/2009 | Allen et al. |

FOREIGN PATENT DOCUMENTS

| | | |
|---|---|---|
| CA | 2433158 | 7/2002 |
| DE | 2 443 714 | 3/1975 |
| EP | 1 558 579 B1 | 8/2005 |
| WO | WO 96/22021 A1 | 7/1996 |
| WO | WO 97/41103 A2 | 11/1997 |
| WO | WO 02/074980 A2 | 9/2002 |
| WO | WO 02/074981 A2 | 9/2002 |
| WO | WO 03/028663 A2 | 4/2003 |
| WO | WO 2004/035812 A2 | 4/2004 |
| WO | WO 2005/007192 A2 | 1/2005 |
| WO | WO 2005/118836 A2 | 12/2005 |
| WO | WO 2006/114213 A1 | 11/2006 |
| WO | WO 2007/038571 A2 | 4/2007 |
| WO | WO 2007/047194 A2 | 4/2007 |
| WO | WO 2007/070359 A2 | 6/2007 |
| WO | WO 2007/082899 A1 | 7/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |
| WO | WO 2008/144266 A1 | 11/2008 |
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |

(Continued)

OTHER PUBLICATIONS

Dannhardt et al., "Z-s-Z-Enaminone und—thione mit semicyclishcher C=C-Bindung," Chemiker-Zeitung, 111(7-8):237-40 (1987) (translation provided).

(Continued)

*Primary Examiner* — Raymond Henley, III
(74) *Attorney, Agent, or Firm* — Richard S. Echler

(57) ABSTRACT

Disclosed herein are compositions and methods for treating colitis and other inflammatory bowel diseases, inter alia, indeterminate colitis, Crohn's disease, irritable bowel syndrome and ischemic colitis.

42 Claims, 3 Drawing Sheets

FOREIGN PATENT DOCUMENTS

| WO | WO 2009/073497 A2 | 6/2009 |
|---|---|---|
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |

OTHER PUBLICATIONS

Muellner, F.W. et al., "The Synthesis of 1,4-ethano-1,2,3,4-tetrahydroisoquinolines as rigid analogues of adrenergic agents," *J. Heterocyclic Chemistry*, (1983), 20, 1581-1584.
Pedersen, et al., "Studies on Organophosphorus compound XX—Synthesis of Thioketones," *Bulletin Des Societes Chimiques Belges*, 87(3):223- (1978).
Posner, G.H. et al., "Diels-Alder cycloadditions using nucleophilic 2-pridones. Regiocontrolled and stereocontrolled synthesis of unsaturated, bridged, bicyclic lactams," J. Organic Chemistry, (1992), 57:15, 4088-4097.
Altschul et al., "Gapped BLAST and PSI-BLAST: A New Generation of Protein Database Search Programs," *Nucleic Acids Res.*, 25(27):3389-3402 (1997).
Annex et al., "Growth Factor-Induced Therapeutic Angiogenesis in the Heart: Protein Therapy," *Cardiovascular Research*, 65(3):649-655 (2005).
Ardelt et al., "Estradiol Regulates Angiopoietin-1 mRNA Expression Through Estrogen Receptor-αin a Rodent Experimental Stroke Model," *Stroke*, 36:337-341 (2005).
Auerbach et al., "Angiogenesis Assays: A Critical Overview," *Clinical Chemistry*, 49:32-40 (2003).
Barany et al., "Solid-phase Peptide Synthesis: A Silver Anniversary Report, " *Int. J. Peptide Protein Res.*, 30(6):705-739 (1987).
Bartlett et al., "Molecular Recognition in Chemical and Biological Problems, " *Special Pub., Royal Chem. Soc.*, 78, 182-196 Caveat: A Program to Facilitate the Structure-derived Design of Biologically Active Molecules (Apr. 1989).
Böhm, "The Computer Program LUDI: A New Method for the Novo Design of Enzyme Inhibitors," *J. Computer-Aided Molecular Design*, 6:61-78 (1992).
Bussolino, "Molecular Mechanisms of Blood Vessel Formation," *Trends Biochem. Sci.*,22(7):251-256 (1997).
Cunliffe et al., "Novel Inhibitors of Prolyl 4-Hydroxylase 3. Inhibition by the Substrate Analogue N-Oxaloglycine and Its Derivatives," *J. Med. Chem.* 35:2652-2658 (1992).
Elson et al., "Induction of Hypervascularity Without Leakage or Inflammation in Transgenic Mice Overexpressing Hypoxia-Indicible Factor-1α," *Genes & Dev.*,15:2520-2532 (2001).
Flower, "Modelling G-protein-coupled receptors for drug design," *Biochimica et Biophysica Acta*, 1422:207-234 (1999).
Folkman et al., "Tumor Angiogenesis," *The Molecular Basis of Cancer*, Mendelsohn et al., eds., W. B. Saunders, Chapter 10, pp. 206-232 (1995).
Franklin et al., "Approaches to the Design of Anti-Fibrotic Drugs," *Biochem. Soc. Trans.*, 19(4):812-5 (Nov. 1991).
Goodford, "A Computational Procedure for Determining Energetically Favorable Binding Sites on Biologically Important Macromolecules," *J. Med. Chem.*, 28(7):849-857 (1985).
Goodsell et al., "Automated Docking of Substrates to Proteins by Simulated Annealing," *Proteins: Structure, Function, and Genetics*, 8:195-202 (1990).
Jones et al., "Molecular Recognition of Receptor Sites Using a Genetic Algorithm with a Description of Desolvation," *J. Mol. Biol.*, 245:43-53 (1995).
Kaelin, "Proline Hydroxylation and Gene Expression," *Annu. Rev. Biochem.*, 74:115-125 (2005).
Krantz, "Erythropoietin," *Blood*, 77:419-434 (1991).
Kuntz et al., "A Geometric Approach to Macromolecule—Ligand Interactions," *J. Mol. Biol.*, 161:269-288 (1982).
Lee et al., "Structure of Human FIH-1 Reveals a Unique Active Site Pocket and Interaction Sites for HIF-1 and von Hippel Lindau," *JBC*, 278:7558-7563 (2003).
Li et al., "PR39, A Peptide Regulator of Angiogenesis," *Nat Med.*, 6(1):49-55 (2000).
Mancini et al., "Effect of Erythropoietin on Exercise Capacity in Patients with Moderate to Severe Chronic Heart Failure," *Circulation*, 107:294-299 (2003).
McDonough et al., "Cellular Oxygen Sensing: Crystal Structure of Hypoxia-Inducible Factor Prolyl Hydroxylase (PHD2)," *PNAS*, 103(26):9814-9819 (2006).
Miranker et al., "Functionality Maps of Binding Sites: A Multiple Copy Simultaneous Search Method," *Proteins: Structure, Function and Genetics*, 11:29-34 (1991).
Nguyen et al., "Cellular Interactions in Vascular Growth and Differentiation," *Int. Review of Cytology*, 204:1-48 (2001).
Nishibata et al., "Automatic Creation of Drug Candidate Structures Based on Receptor Structure. Starting Point for Artificial Lead Generation," *Tetrahedron*, 47(43):8985-8990 (1991).
O'Reilly et al., "Angiostatin: A Novel Angiogenesis Inhibitor that Mediates the Suppression of Metastases by a Lewis Lung Carcinoma," *Cell*, 79:315-328 (1994).
O'Reilly et al., "Endostatin: An Endogenous Inhibitor of Angiogenesis and Tumor Growth," *Cell*, 88:277-285 (1997).
Peyssonnaux et al., "HIF-1αExpression Regulates the Bactericidal Capacity of Phagocytes," *J. Clinical Invest.*, 115(7):1806-1815.
Schoneberg et al., "Structural Basis of G Protein-Coupled Receptor Function," *Molecular and Cellular Endocrinology*, 151:181-193 (1999).
Semenza, "Signal Transduction to Hypoxia-inducible Factor 1," *Biochem. Pharmacol*, 64:993-998 (2002).
Semenza, "Regulation of Erythropoietin Porduction: New Insights into Molecular Mechanisms of Oxygen Homeostasis," *Hematol. Oncol. Clin. North Am.*, 8:863-884 (1994).
Semenza et al., "Transcriptional Regulation of Genes Encoding Glycolytic Enzymes by Hypoxia-Inducible Factor 1," *J. Biol. Chem.*, 269:23757-23763 (1994).
Sexton, "Recent advances in our understanding of peptide hormone receptors and RAMPS," *Current Opinion in Drug Discovery and Development*, 2(5):440-448 (1999).
Sheehan, "3-Hydroxypicolinic Acid and Some of its Derivatives," *J. Organic Chemistry* 31(3):636-638 (1996).
Teicher et al., "Potentiation of Cytotoxic Cancer Therapies by TNP-470 Alone and with Other Anti-Angiogenic Agents," *Int. J. Cancer*, 57:920-925 (1994).
Vincent et al., "Angiogenesis is Induced in a Rabbit Model of Hindlimb Ischemia by Naked DNA Encoding an HIF-1α/VP16 Hybrid Transcription Factor," *Circulation*, 102:2255-2261 (2000).
Warnecke et al., "Activation of the Hypoxia-Inducible Factor Pathway and Stimulation of Angiogenesis by Application of Prolyl Hydroxylase Inhibitors," *FASEB Journal*, 17:1186-1188 (2003).
Warner et al., "Epolones induce erythropoietin expression via hypoxia-inducible factor-1αactivation," *Blood*, 96(4): 1558-1565 (2000).
Wax et al., "SM-20 is a Novel 20-kd Protein Whose Expression in the Arterial Wall is Restricted to Smooth Muscle," *Lab. Invest.*, 74(4):797-808 (1996).
Weidner et al., "Tumor Angiogenesis and Metastasis—Correlation in Invasive Breast Carcinoma," *New Eng. J Med.*, 324(1):1-8 (1991).
Wright et al., "Activation of the Prolyl Hydroxylase Oxygen-Sensor Results in Induction of GLUT1, Heme Oxygenase-1, and Nitric-Oxide Synthase Proteins and Confers Protection from Metabolic Inhibition to Cardiomyocytes," *J. Bio. Chem.*, 278(22):20235-20239 (2003).

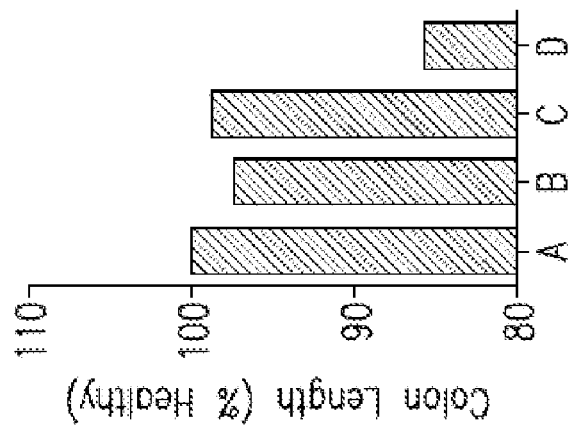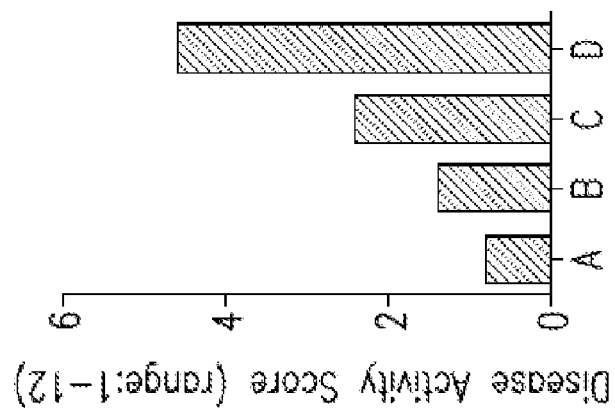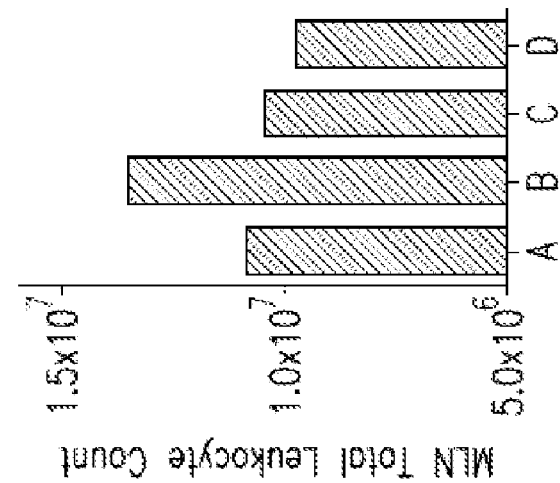

US 8,309,537 B2

COMPOSITIONS AND METHODS FOR TREATING COLITIS

PRIORITY

This application claims the benefit of Provisional Application Ser. No. 61/258,914 and Provisional Application Ser. No. 61/258,918 that were both filed on Nov. 6, 2009, the entirety of which applications are incorporated herein by reference.

FIELD OF THE DISCLOSURE

Disclosed herein are compositions and methods for treating colitis and other inflammatory bowel diseases, inter alia, ulcerative colitis, Crohn's disease, irritable bowel syndrome and ischemic colitis.

SUMMARY

Colitis is the term used to describe inflammation of the colon. There are a variety of causes of colitis including infections, poor blood supply, and autoimmune reactions. The wall of the colon has numerous layers. There is a smooth muscle layer that wraps the outside and is responsible for squeezing the undigested food through the length of the colon. The inner layers, or mucosa, come into contact with the fluid and allow water and electrolyte absorption to help solidify the feces. The mucosal layer is where the colon inflammation occurs and is responsible for the symptoms of colitis.

There are two types of inflammatory bowel disease. The first, ulcerative colitis, is thought to be an autoimmune illness in which the body's immune system attacks the colon and causes inflammation. Ulcerative colitis begins in the rectum and may gradually spread throughout the colon. The signs and symptoms are generally abdominal pain and bloody bowel movements.

Crohn's disease is a second type of inflammatory bowel disease, and can involve any part of the digestive tract from the esophagus and stomach to both the small and large intestine. It often has skip lesions, that is diseased areas are interspersed with healthy areas of tissue.

The inflammatory bowel diseases (IBDs), ulcerative colitis and Crohn's disease, are currently controlled by a combination of medications that are used in a step-wise approach. Initially, anti-inflammatory medications are used, and if these are less than successful, medications that suppress the immune system can be added. In the most severe cases, surgery may be required to remove all or parts of the colon and small intestine. Treatment for ischemic colitis is initially supportive, using intravenous fluids to rest the bowel and prevent dehydration. If adequate blood supply to the bowel isn't restored, surgery may be required to remove parts of the bowel that have lost blood supply.

The disclosed compositions and methods comprise compounds that can stabilize HIF-1α and HIF-2α, as well as other factors that are present in the compromised, depleted or over taxed immune system of a subject suffering from colitis or other inflammatory bowel disease. As such, the causes of colitis and colitis related diseases can be successfully treated without the need for surgical intervention.

BRIEF DESCRIPTION OF THE FIGURES

FIG. 2a depicts the percent colon length found in the following treatment groups: (A) healthy mice; (B) mice having TNBS-induced colitis pre-treated with 5 mg/kg a compound disclosed in Table VIII one day prior to disease induction; (C) mice having TNBS-induced colitis post-treated with 5 mg/kg a compound disclosed in Table VIII two days post disease induction; and (D) mice having TNBS-induced colitis receiving only vehicle treatment.

FIG. 2b depicts the disease activity scores for (A) healthy mice; (B) mice having TNBS-induced colitis pre-treated with 5 mg/kg a compound disclosed in Table VIII one day prior to disease induction; (C) mice having TNBS-induced colitis post-treated with 5 mg/kg a compound disclosed in Table VIII two days post disease induction; and (D) mice having TNBS-induced colitis receiving only vehicle treatment.

FIG. 2c shows the mesenteric lymph node (MLN) total leukocyte count for animals receiving vehicle (A), TNBS-induced colitis receiving only ethanol vehicle (B), animals without TNBS-induced colitis receiving 10 mg/kg a compound disclosed in Table VIII; and animals having TNBS-induced colitis and receiving 10 mg/kg a compound disclosed in Table VIII.

DETAILED DISCLOSURE

Figure 1:
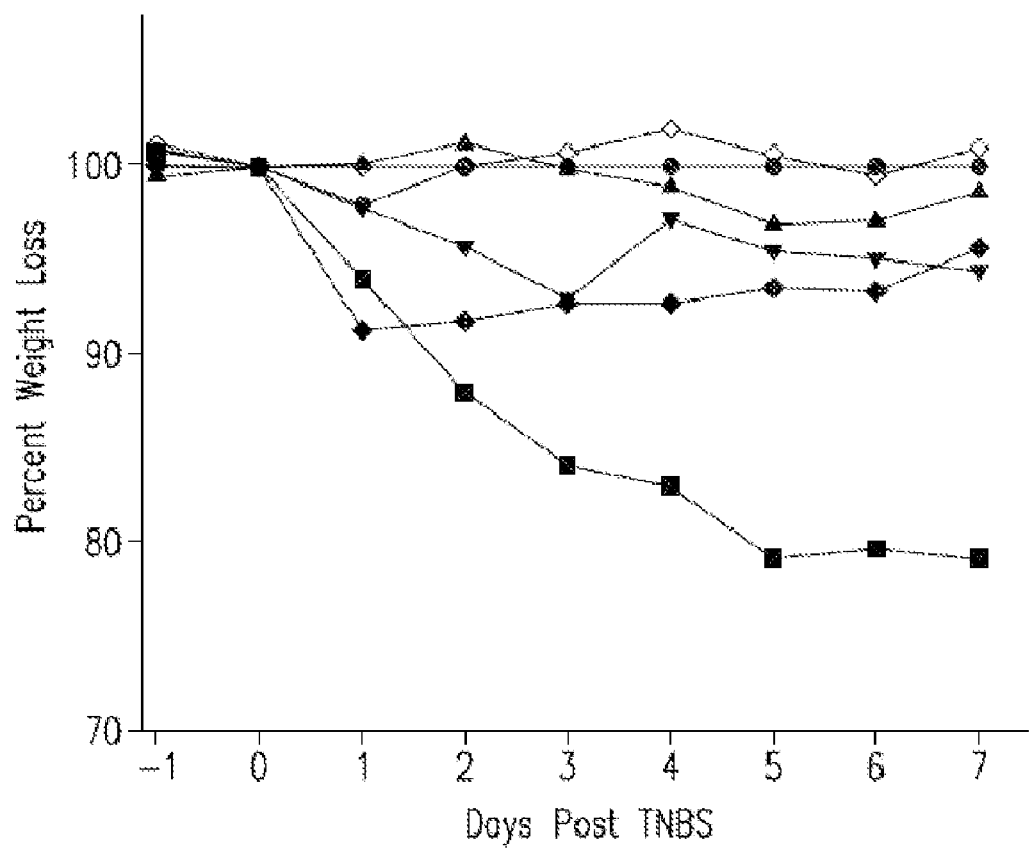
FIG. 1 depicts the prevention of weight loss in mice with TNBS-induced colitis due to pre-treatment with a compound disclosed in Table VIII. The data represented by solid circles (●) represent control animals without induced colitis and pretreated with vehicle, solid squares (■) represent control animals with TNBS-induced colitis and pre-treated with vehicle, solid triangles (▲) represent animals without induced colitis that were pre-treated with 5 mg/kg of a compound disclosed in Table VIII, solid inverted triangles (▼) represent animals with TNBS-induced colitis that were pre-treated with 0.3 mg/kg of a compound disclosed in Table VIII, solid diamonds (♦) represent animals with TNBS-induced colitis that were pre-treated with 1 mg/kg of a compound disclosed in Table VIII, and open circles (○) represent animals with TNBS-induced colitis that were pre-treated with 5 mg/kg of a compound disclosed in Table VIII.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

"Optional" or "optionally" means that the subsequently described event or circumstance can or cannot occur, and that the description includes instances where the event or circumstance occurs and instances where it does not.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "effective amount" as used herein means "an amount of one or more of the disclosed HIF-1α prolyl hydroxylase inhibitors, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "Treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., infection caused by a microorganism). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. By "antimicrobial" is meant the ability to treat or control (e.g., reduce, prevent, inhibit, break-down, or eliminate) microorganism growth or survival at any concentration. Similarly, the terms "antibacterial," "antiviral," and "antifungal" respectively mean the ability to treat or control (e.g., reduce, prevent, inhibit, break-down, or eliminate) bacterial, viral, and fungal growth or survival at any concentration.

The term "anion" is a type of ion and is included within the meaning of the term "ion". An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion". A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

"Chemotherapeutic agent" is used herein to include any other pharmaceutically active compound that can be used in conjunction with the disclosed HIF-1α prolyl hydroxylase inhibitors, for example, cytotoxic drugs such as 6-hydroxymethylacylfulvene, cyclophosphamide, dacarbazine, carmustine, doxorubicin, and methotrexate. Other chemotherapeutic agents also include anti-inflammatory drugs, i.e., non-steroidal anti-inflammatory compounds such as aspirin.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (carbocyclic and aryl rings) or can comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decalinyl ($C_{10}$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$).

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

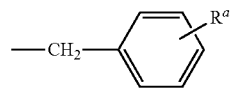

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

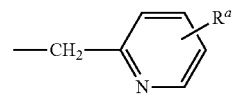

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan can have alternative characterizations. For example, 1,2,3,4-tetrahydroquinoline having the formula:

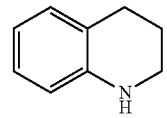

is, for the purposes of the present disclosure, considered a heterocyclic unit. 6,7-Dihydro-5H-cyclopentapyrimidine having the formula:

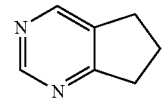

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

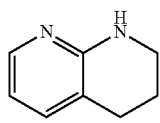

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms can be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) substituted or unsubstituted $C_1$-$C_{12}$ linear, $C_3$-$C_{12}$ branched, or $C_3$-$C_{12}$ cyclic alkyl; for example, methyl ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;

iv) substituted or unsubstituted $C_6$ or $C_{10}$ aryl; for example, phenyl, 2-chlorophenyl, 3-hydroxyphenyl, 4-nitrophenyl, 2-fluoro-4-methylphenyl, 3,5-dinitrophenyl, 8-hydroxynaphth-1-yl, 6-sulfonylnapth-2-yl, and the like;

v) substituted or unsubstituted $C_1$-$C_9$ heterocyclic; for example, as defined further herein;

vi) substituted or unsubstituted $C_1$-$C_{11}$ heteroaryl; for example, as defined further herein;

vii) halogen; for example, fluoro, chloro, bromo, and iodo;

viii) —[C($R^{23a}$)($R^{23b}$)]$_x$O$R^{10}$;

$R^{10}$ is chosen from:
a) —H;
b) substituted or unsubstituted $C_1$-$C_{12}$ linear, $C_3$-$C_{12}$ branched, or $C_3$-$C_{12}$ cyclic alkyl;
c) $C_6$ or $C_{10}$ substituted or unsubstituted aryl or alkylenearyl;
d) $C_1$-$C_9$ substituted or unsubstituted heterocyclic;
e) $C_1$-$C_{11}$ substituted or unsubstituted heteroaryl;

ix) —[C($R^{23a}$)($R^{23b}$)]$_x$N($R^{11a}$)($R^{11b}$);

$R^{11a}$ and $R^{11b}$ are each independently chosen from:
a) —H;
b) —O$R^{12}$;
$R^{12}$ is hydrogen or $C_1$-$C_4$ linear alkyl;
c) substituted or unsubstituted $C_1$-$C_{12}$ linear, $C_3$-$C_{12}$ branched, or $C_3$-$C_{12}$ cyclic alkyl;
d) $C_6$ or $C_{10}$ substituted or unsubstituted aryl;
e) $C_1$-$C_9$ substituted or unsubstituted heterocyclic;
f) $C_1$-$C_{11}$ substituted or unsubstituted heteroaryl; or
g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;

x) —[C($R^{23a}$)($R^{23b}$)]$_x$C(O)$R^{13}$;

$R^{13}$ is:
a) substituted or unsubstituted $C_1$-$C_{12}$ linear, $C_3$-$C_{12}$ branched, or $C_3$-$C_{12}$ cyclic alkyl;
b) —O$R^{14}$;
$R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
c) —N($R^{15a}$)($R^{15b}$);
$R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xi) —[C($R^{23a}$)($R^{23b}$)]$_x$OC(O)$R^{16}$;

$R^{16}$ is:
a) substituted or unsubstituted $C_1$-$C_{12}$ linear, $C_3$-$C_{12}$ branched, or $C_3$-$C_{12}$ cyclic alkyl;
b) —N($R^{17a}$)($R^{17b}$);
$R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —[C(R$^{23a}$)(R$^{23b}$)]$_x$NR$^{18}$C(O)R$^{19}$;
R$^{18}$ is:
a) —H; or
b) substituted or unsubstituted C$_1$-C$_4$ linear, C$_3$-C4 branched, or C$_3$-C4 cyclic alkyl;
R$^{19}$ is:
a) substituted or unsubstituted C$_1$-C$_{12}$ linear, C$_3$-C$_{12}$ branched, or C$_3$-C$_{12}$ cyclic alkyl;
b) —N(R$^{20a}$)(R$^{20b}$);
R$^{20a}$ and R$^{20b}$ are each independently hydrogen, substituted or unsubstituted C$_1$-C$_{12}$ linear, C$_3$-C$_{12}$ branched, or C$_3$-C$_{12}$ cyclic alkyl; C$_6$ or C$_{10}$ substituted or unsubstituted aryl; C$_1$-C$_9$ substituted or unsubstituted heterocyclic; C$_1$-C$_{11}$ substituted or unsubstituted heteroaryl; or R$^{20a}$ and R$^{20b}$ can be taken together to form a substituted or unsubstituted ring having from 3 to 10 carbon atoms and from 0 to 3 heteroatoms chosen from oxygen, nitrogen, and sulfur;
xiii) —[C(R$^{23a}$)(R$^{23b}$)]$_x$CN;
xiv) —[C(R$^{23a}$)(R$^{23b}$)]$_x$NO$_2$;
xv) —[C(R$^{23a}$)(R$^{23b}$)]$_x$R$^{21}$;
R$^{21}$ is C$_1$-C$_{10}$ linear, C$_3$-C$_{10}$ branched, or C$_3$-C$_{10}$ cyclic alkyl substituted by from 1 to 21 halogen atoms chosen from —F, —Cl, —Br, or —I;
xvi) —[C(R$^{23a}$)(R$^{23b}$)]$_x$SO$_2$R$^{22}$;
R$^{22}$ is hydrogen, hydroxyl, substituted or unsubstituted C$_1$-C$_4$ linear or C$_3$-C$_4$ branched alkyl; substituted or unsubstituted C$_6$, C$_{10}$, or C$_{14}$ aryl; C$_2$-C$_{15}$ alkylenearyl; C$_1$-C$_9$ substituted or unsubstituted heterocyclic; or C$_1$-C$_{11}$ substituted or unsubstituted heteroaryl;
R$^{23a}$ and R$^{23b}$ are each independently hydrogen or C$_1$-C$_4$ alkyl; and
the index x is an integer from 0 to 5.

The compounds disclosed herein include all salt forms, for example, salts of both basic groups, inter alia, amines, as well as salts of acidic groups, inter alia, carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

For the purposes of the present disclosure the terms "compound," "analog," and "composition of matter" stand equally well for one another and include all enantiomeric forms, diastereomeric forms, salts, and the like, and the terms "compound," "analog," and "composition of matter."

HIF-1α Prolyl Hydroxylase Inhibitors

The disclosed compounds have the following formulae:

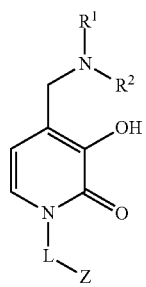

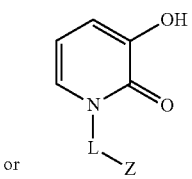

wherein L is chosen from CH$_2$ or SO$_2$, thereby providing for N-substituted benzyl or N-substituted sulfonylaryl-3-hydroxypyridin-2-(1H)-ones. Y, R$^1$ and R$^2$ are further defined herein below.

Disclosed herein are N-substituted benzyl and N-substituted sulfonylaryl-4-aminomethylene-3-hydroxypyridin-2-(1H)-ones that are HIF-1α prolyl hydroxylase inhibitors having the formula:

wherein R$^1$ and R$^2$ are further defined herein below.

Alkyl Piperizine-1-Carboxylates

One category of these compounds relates to C$_1$-C$_4$ linear or branched alkyl 4-{[(1-N-(chloro- or fluoro-substituted)-benzyl]-3-hydroxy-2-oxo-1,2-dihydropyridin-4-yl) methyl}piperazine-1-carboxylates having the formula:

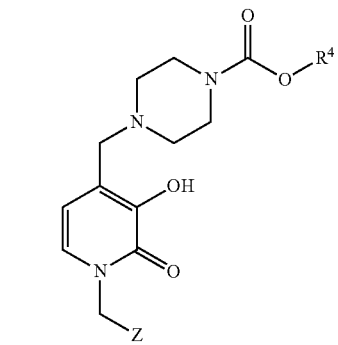

wherein Z is a phenyl group that is substituted with from 1 to 5 halogen atoms that are chosen from chloro and fluoro, and R$^1$ and R$^2$ are taken together to form a piperazine ring that is substituted with alkylcarboxy unit wherein R$^4$ is chosen from C$_1$-C$_4$ linear or C$_3$-C$_4$ branched alkyl, for example, tert butyl 4{[1-(4chlorobenzyl)-3-hydroxy-2-oxo1,2-dihydropyridin-4-yl]methyl}piperazine-1-carboxylate having the formula:

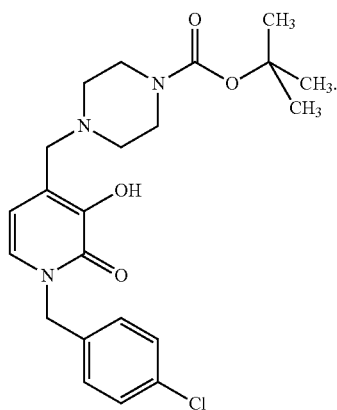

One aspect of $R^4$ units relates to compounds wherein $R^4$ is tert-butyl ($C_4$). Another aspect of $R^4$ units relates to compounds wherein $R^4$ is methyl ($C_1$). A further aspect of $R^4$ units relates to compounds wherein $R^4$ is ethyl ($C_2$). A still further aspect of $R^4$ units relates to compounds wherein $R^4$ is chosen from n-propyl ($C_3$), iso-propyl ($C_3$), n-butyl ($C_4$), sec-butyl ($C_4$), and iso-butyl ($C_4$). $R^4$ is not hydrogen, therefore, a carboxylate unit having the formula: —$CO_2H$ is expressly excluded from this category, but may be included in other categories as described herein below.

Z is phenyl substituted with from 1 to 5 halogens chosen from fluorine and chlorine. One aspect of Z units relates to compounds wherein Z is 4-chlorophenyl. Another aspect of Z units relates to compounds wherein Z is chosen from 2-chlorophenyl, 3-chlorophenyl, 2-fluorophenyl, 3-fluorophenyl, or 4-fluorophenyl. A further aspect of Z units relates to compounds wherein Z is chosen from 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, and 2,6-dichlorophenyl.

The following are non-limiting examples of compounds according to this category:

methyl 4-{[1-(4-chlorobenzyl)-3-hydroxy-2-oxo-1,2-dihydropyridin-4-yl]methyl}-piperazine-1-carboxylate having the formula:

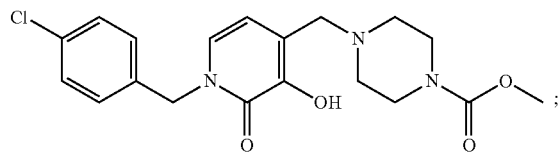

methyl 4-{[1-(3-chlorobenzyl)-3-hydroxy-2-oxo-1,2-dihydropyridin-4-yl]methyl}-piperazine-1-carboxylate having the formula:

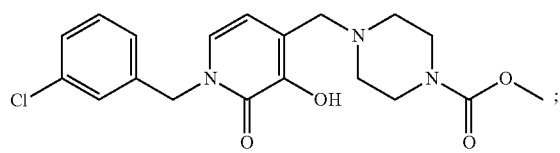

methyl 4-{[1-(2-chlorobenzyl)-3-hydroxy-2-oxo-1,2-dihydropyridin-4-yl]methyl}-piperazine-1-carboxylate having the formula:

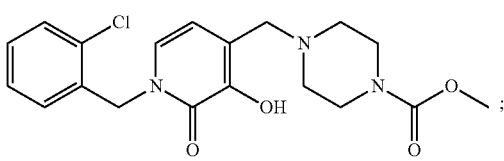

ethyl 4-{[1-(4-chlorobenzyl)-3-hydroxy-2-oxo-1,2-dihydropyridin-4-yl]methyl}-piperazine-1-carboxylate having the formula:

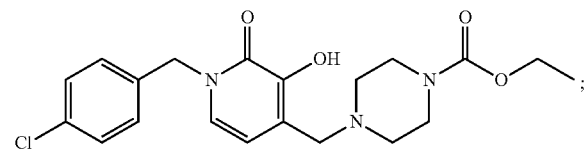

ethyl 4-{[1-(3-chlorobenzyl)-3-hydroxy-2-oxo-1,2-dihydropyridin-4-yl]methyl}-piperazine-1-carboxylate having the formula:

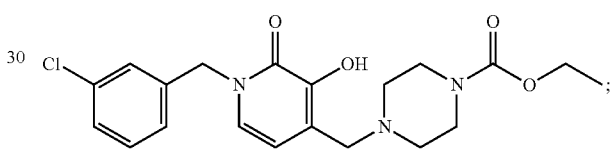

ethyl 4-{[1-(2-chlorobenzyl)-3-hydroxy-2-oxo-1,2-dihydropyridin-4-yl]methyl}-piperazine-1-carboxylate having the formula:

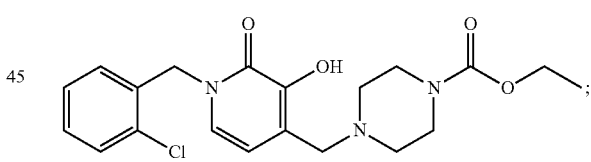

tert-butyl 4-{[1-(4-chlorobenzyl)-3-hydroxy-2-oxo-1,2-dihydropyridin-4-yl]methyl}-piperazine-1-carboxylate having the formula:

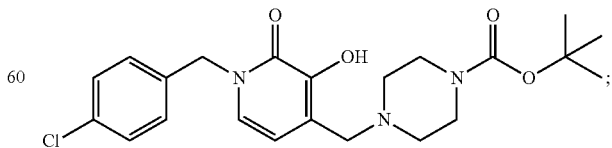

tert-butyl 4-{[1-(3-chlorobenzyl)-3-hydroxy-2-oxo-1,2-dihydropyridin-4-yl]methyl}-piperazine-1-carboxylate having the formula:

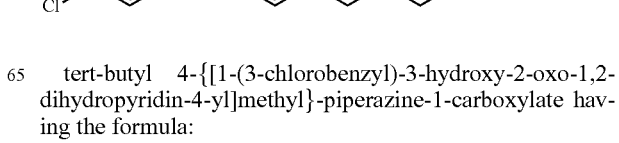

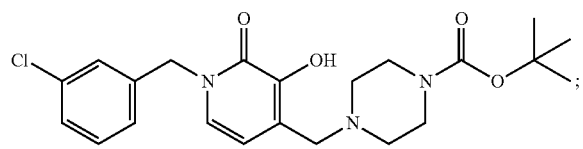

tert-butyl 4-{[1-(2-chlorobenzyl)-3-hydroxy-2-oxo-1,2-dihydropyridin-4-yl]methyl}-piperazine-1-carboxylate having the formula:

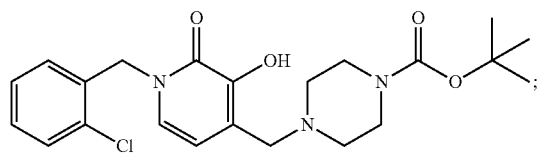

methyl 4-{[1-(4-fluorobenzyl)-3-hydroxy-2-oxo-1,2-dihydropyridin-4-yl]methyl}-piperazine-1-carboxylate having the formula:

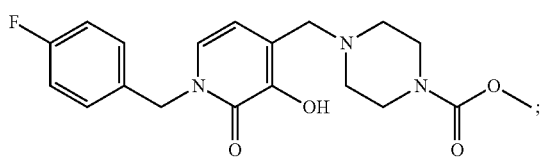

methyl 4-{[1-(3-fluorobenzyl)-3-hydroxy-2-oxo-1,2-dihydropyridin-4-yl]methyl}-piperazine-1-carboxylate having the formula:

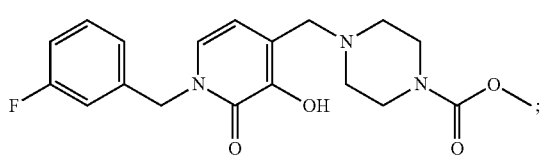

methyl 4-{[1-(2-fluorobenzyl)-3-hydroxy-2-oxo-1,2-dihydropyridin-4-yl]methyl}-piperazine-1-carboxylate having the formula:

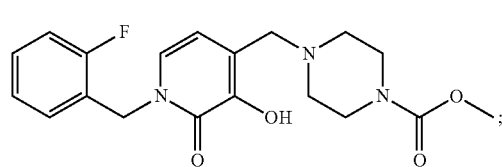

ethyl 4-{[1-(4-fluorobenzyl)-3-hydroxy-2-oxo-1,2-dihydropyridin-4-yl]methyl}-piperazine-1-carboxylate having the formula:

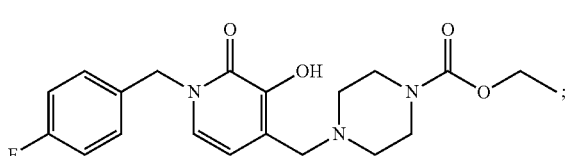

ethyl 4-{[1-(3-fluorobenzyl)-3-hydroxy-2-oxo-1,2-dihydropyridin-4-yl]methyl}-piperazine-1-carboxylate having the formula:

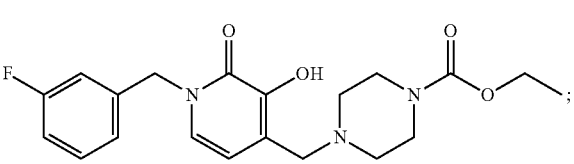

ethyl 4-{[1-(2-fluorobenzyl)-3-hydroxy-2-oxo-1,2-dihydropyridin-4-yl]methyl}-piperazine-1-carboxylate having the formula:

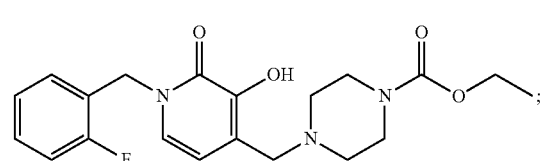

tert-butyl 4-{[1-(4-fluorobenzyl)-3-hydroxy-2-oxo-1,2-dihydropyridin-4-yl]methyl}-piperazine-1-carboxylate having the formula:

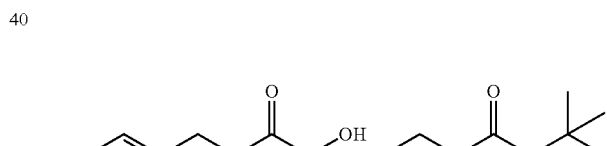

tert-Butyl 4-{[1-(3-fluorobenzyl)-3-hydroxy-2-oxo-1,2-dihydropyridin-4-yl]methyl}-piperazine-1-carboxylate having the formula:

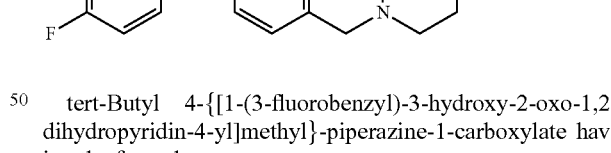

and tert-butyl 4-{[1-(2-fluorobenzyl)-3-hydroxy-2-oxo-1,2-dihydropyridin-4-yl]methyl}piperazine-1-carboxylate having the formula:

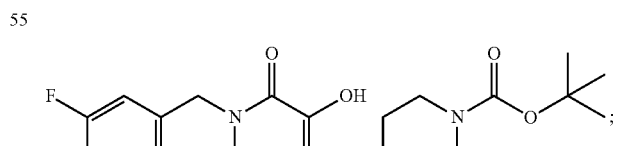

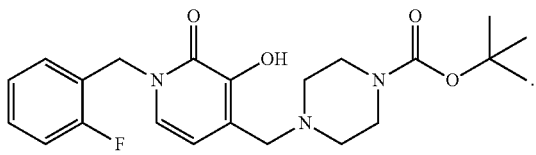

Another category of compounds relates to N-unsubstituted-benzyl-4-aminomethyl-3-hydroxypyridin-2-(1H)-ones, wherein Z is an unsubstituted phenyl group, having the formula:

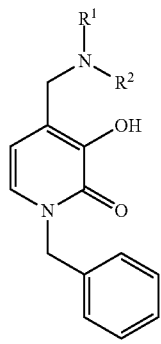

wherein $R^1$ and $R^2$ are be taken together to form a substituted or unsubstituted heterocyclic or heteroaryl ring.

A first aspect of this category relates to compounds having the formula:

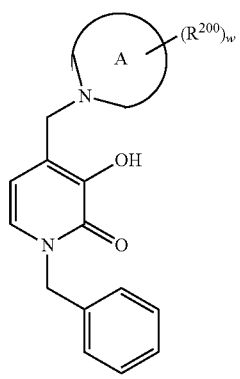

wherein $R^1$ and $R^2$ are be taken together to form a substituted or unsubstituted heterocyclic or heteroaryl ring represented by ring A having from 2 to 20 carbon atoms and from 1 to 7 heteroatoms, and $R^{200}$ represents from 0 to 40 substitutions form hydrogen. The index w is an integer from 0 to 40. Non-limiting examples of rings include diazirinyl ($C_1$), 1,2,3,4-tetrazolyl ($C_1$), aziridinyl ($C_2$), urazolyl ($C_2$), [1,2,3]triazolyl ($C_2$), [1,2,4]triazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), 1H-imidazolyl ($C_3$), pyrrolidinyl ($C_4$), morpholinyl ($C_4$), piperazinyl ($C_4$), piperidinyl ($C_4$), piperidin-2-onyl (valerolactam) ($C_5$), 7H-purinyl ($C_5$), 9H-purinyl ($C_5$), 6-amino-9H-purinyl ($C_5$), 2,3,4,5-tetrahydro-1H-azepinyl ($C_6$), 5H-pyrrolo[3,2-d]pyrimidinyl ($C_6$), 7H-pyrrolo[2,3-d]pyrimidinyl ($C_6$), and 1,2,3,4-tetrahydroquinoline ($C_9$).

Each $R^{200}$ unit is independently chosen from:
i) substituted or unsubstituted $C_1$-$C_{12}$ linear, $C_3$-$C_{12}$ branched, or $C_3$-$C_{12}$ cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_1$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;

iv) substituted or unsubstituted $C_6$ or $C_{10}$ aryl; for example, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-cyano-naphthylen-1-yl ($C_{10}$), and the like;

v) substituted or unsubstituted $C_1$-$C_9$ heterocyclic; for example, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydropyranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), and the like;

vi) substituted or unsubstituted $C_1$-$C_{11}$ heteroaryl; for example, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), pyridinyl ($C_5$), and the like;

vii) halogen; for example, —F, —Cl, —Br, or —I;

viii) —[C($R^{37a}$)($R^{37b}$)]$_y$O$R^{24}$;

$R^{24}$ is chosen from:

a) —H;

b) substituted or unsubstituted $C_2$-$C_{12}$ linear, $C_3$-$C_{12}$ branched, or $C_3$-$C_{12}$ cyclic alkyl;

c) substituted or unsubstituted $C_6$ or $C_{10}$ aryl or $C_7$ or $C_{10}$ alkylenearyl; for example, phenyl or benzyl d) substituted or unsubstituted $C_1$-$C_9$ heterocyclic;

e) substituted or unsubstituted $C_1$-$C_{11}$ heteroaryl;

for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

ix) —[C(R$^{37a}$)(R$^{37b}$)]$_y$N(R$^{25a}$)(R$^{25b}$);
R$^{25a}$ and R$^{25b}$ are each independently chosen from:
a) —H;
b) —OR$^{26}$;
R$^{26}$ is hydrogen or C$_1$-C$_4$ linear alkyl;
c) substituted or unsubstituted C$_2$-C$_{12}$ linear, C$_3$-C$_{12}$ branched, or C$_3$-C$_{12}$ cyclic alkyl;
d) substituted or unsubstituted C$_6$ or C$_{10}$ aryl;
e) substituted or unsubstituted C$_1$-C$_9$ heterocyclic;
f) substituted or unsubstituted C$_1$-C$_{11}$ heteroaryl; or
g) R$^{25a}$ and R$^{25b}$ can be taken together to form a substituted or unsubstituted ring having from 3 to 10 carbon atoms and from 0 to 3 heteroatoms chosen from oxygen, nitrogen, and sulfur;
for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;
x) —[C(R$^{37a}$)(R$^{37b}$)]$_y$C(O)R$^{27}$;
R$^{27}$ is:
a) substituted or unsubstituted C$_2$-C$_{12}$ linear, C$_3$-C$_{12}$ branched, or C$_3$-C$_{12}$ cyclic alkyl;
b) —OR$^{28}$;
R$^{28}$ is hydrogen, substituted or unsubstituted C$_1$-C$_4$ linear alkyl, substituted or unsubstituted C$_6$ or C$_{10}$ aryl, substituted or unsubstituted C$_1$-C$_9$ heterocyclic, substituted or unsubstituted C$_1$-C$_{11}$ heteroaryl;
c) —N(R$^{29a}$)(R$^{29b}$);
R$^{29a}$ and R$^{29b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; or R$^{29a}$ and R$^{29b}$ can be taken together to form a substituted or unsubstituted ring having from 3 to 10 carbon atoms and from 0 to 3 heteroatoms chosen from oxygen, nitrogen, and sulfur;
for example, —COCH$_3$, —CH$_2$COCH$_3$, —OCH$_2$CH$_3$, —CH$_2$COCH$_2$CH$_3$, —COCH$_2$CH$_2$CH$_3$, —CH$_2$COCH$_2$CH$_2$CH$_3$, and the like;
xi) —[C(R$^{37a}$)(R$^{37b}$)]$_y$OC(O)R$^{30}$;
R$^{30}$ is:
a) C$_1$-C$_{12}$ substituted or unsubstituted linear, branched, or cyclic alkyl;
b) —N(R$^{31a}$)(R$^{31b}$);
R$^{31a}$ and R$^{31b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; or R$^{31a}$ and R$^{31b}$ can be taken together to form a substituted or unsubstituted ring having from 3 to 10 carbon atoms and from 0 to 3 heteroatoms chosen from oxygen, nitrogen, and sulfur;
for example, —OC(O)CH$_3$, —CH$_2$OC(O)CH$_3$, —OC(O)NH$_2$, —CH$_2$OC(O)NH$_2$, —OC(O)NHCH$_3$, —CH$_2$OC(O)NHCH$_3$, —OC(O)N(CH$_3$)$_2$, —CH$_2$OC(O)N(CH$_3$)$_2$, and the like;
xii) —[C(R$^{37a}$)(R$^{37b}$)]$_y$NR$^{32}$C(O)R$^{33}$;
R$^{32}$ is:
a) —H; or
b) substituted or unsubstituted C$_1$-C$_4$ linear, C$_3$-C$_4$ branched, or C$_3$-C$_4$ cyclic alkyl;

R$^{33}$ is:
a) substituted or unsubstituted C$_2$-C$_{12}$ linear, C$_3$-C$_{12}$ branched, or C$_3$-C$_{12}$ cyclic alkyl;
b) —N(R$^{34a}$)(R$^{34b}$);
R$^{34a}$ and R$^{34b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; C$_1$-C$_{11}$ substituted or unsubstituted heteroaryl; or R$^{34a}$ and R$^{34b}$ can be taken together to form a substituted or unsubstituted ring having from 3 to 10 carbon atoms and from 0 to 3 heteroatoms chosen from oxygen, nitrogen, and sulfur;
for example, —NHC(O)CH$_3$, —CH$_2$NHC(O)CH$_3$, —NHC(O)NH$_2$, —CH$_2$NHC(O)NH$_2$, —NHC(O)NHCH$_3$, —CH$_2$NHC(O)NHCH$_3$, —OC(O)N(CH$_3$)$_2$, —CH$_2$NHC(O)N(CH$_3$)$_2$, and the like;
xiii) —[C(R$^{37a}$)(R$^{37b}$)]$_y$CN; for example; —CN, —CH$_2$CN, and —CH$_2$CH$_2$CN;
xiv) —[C(R$^{37a}$)(R$^{37b}$)]$_y$NO$_2$; for example; —NO$_2$, —CH$_2$NO$_2$, and —CH$_2$CH$_2$NO$_2$;
xv) —[C(R$^{37a}$)(R$^{37b}$)]$_y$R$^{35}$; for example, —CH$_2$F, —CHF$_2$, —CF$_3$, —CCl$_3$, or —CBr$_3$;
R$^{35}$ is C$_1$-C$_{10}$ linear, C$_3$-C$_{10}$ branched, or C$_3$-C$_{10}$ cyclic alkyl substituted by from 1 to 21 halogen atoms chosen from —F, —Cl, —Br, or —I;
xvi) —[C(R$^{37a}$)(R$^{37b}$)]$_y$SO$_2$R$^{36}$;
R$^{36}$ is hydrogen, hydroxyl, substituted or unsubstituted C$_1$-C$_4$ linear or C$_3$-C$_4$ branched alkyl; substituted or unsubstituted C$_6$, C$_{10}$, or C$_{14}$ aryl; C$_7$-C$_{15}$ alkylenearyl; substituted or unsubstituted C$_1$-C$_9$ heterocyclic; or substituted or unsubstituted C$_1$-C$_{11}$ heteroaryl;
for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xv) two hydrogen atoms on a ring carbon atom can be substituted to form a =O, =S, or =NH unit;
R$^{37a}$ and R$^{37b}$ are each independently hydrogen or C$_1$-C$_4$ alkyl; and
the index y is an integer from 0 to 5.

A first embodiment of this aspect relates to compounds wherein R$^1$ and R$^2$ are taken together to form a 5-member substituted or unsubstituted C$_1$-C$_4$ heterocyclic or a substituted or unsubstituted C$_1$-C$_4$ heteroaryl ring, non-limiting examples of which include a ring chosen from:

i)

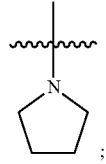
;

ii)

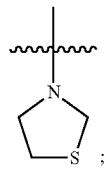
;

ii) 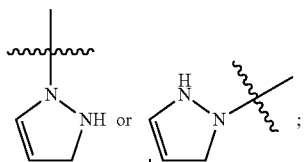

iii) 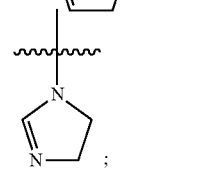

iv) 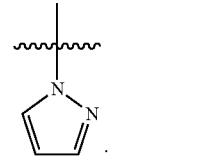

v) 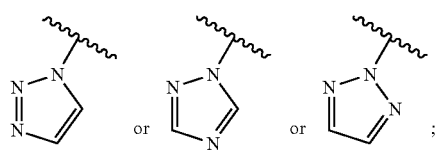

vi) 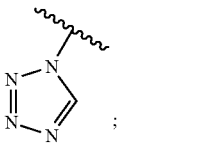

vii) 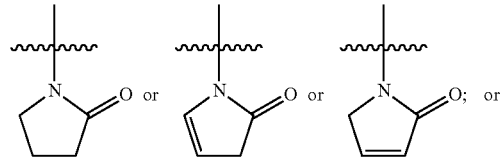

viii) 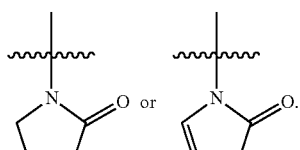

A first iteration of this embodiment relates to HIF-1α prolyl hydroxylase inhibitors having the formula:

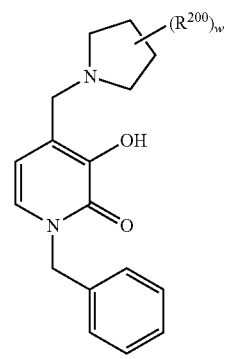

$R^{200}$ represents from 0 to 2 substitutions for a ring hydrogen, wherein the substitutions for hydrogen are independently chosen from:
  i) $C_1$-$C_4$ linear or $C_3$-$C_4$ branched alkyl;
  ii) $C_1$-$C_4$ linear or $C_3$-$C_4$ branched alkoxy;
  iii) hydroxyl;
  iv) cyano;
  v) nitro;
  vi) amino, methylamino, or dimethylamino;
  vii) carboxy, methyl carboxy; or ethyl carboxy;
  viii) formyl, acetyl, or propionyl;
  ix) amido, methyl amido, or dimethyl amido;
  x) halogen;
  xi) heterocyclic; or
  xii) heteroaryl.

Non-limiting examples of this iteration include HIF-1α prolyl hydroxylase inhibitors having the formula:

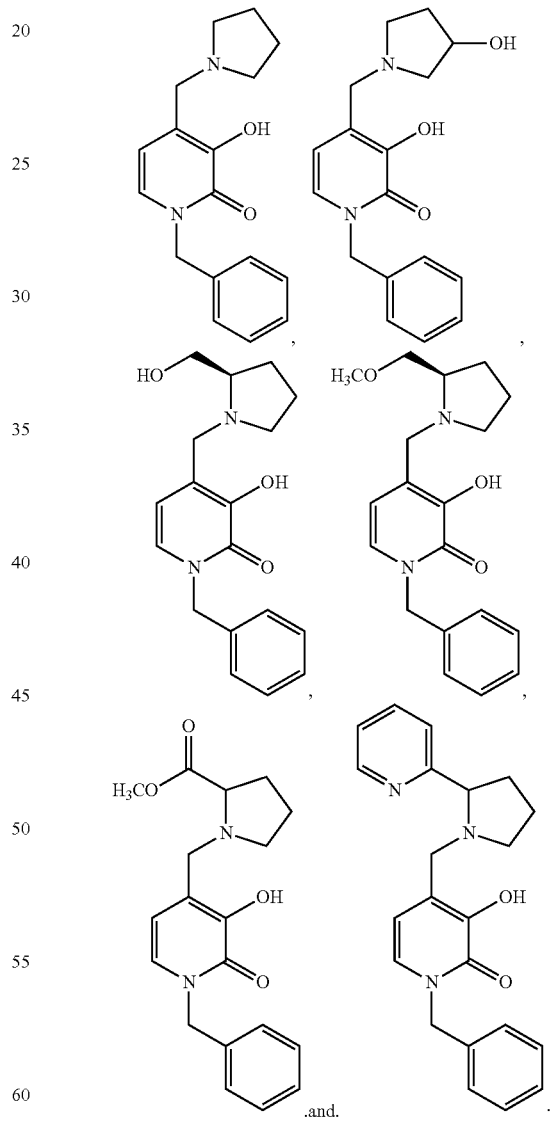

A further iteration of this embodiment relates to HIF-1α prolyl hydroxylase inhibitors wherein $R^1$ and $R^2$ are taken together to form a 5-member substituted or unsubstituted heterocyclic or heteroaryl ring having more than one heteroatom in the ring. Non-limiting examples include:

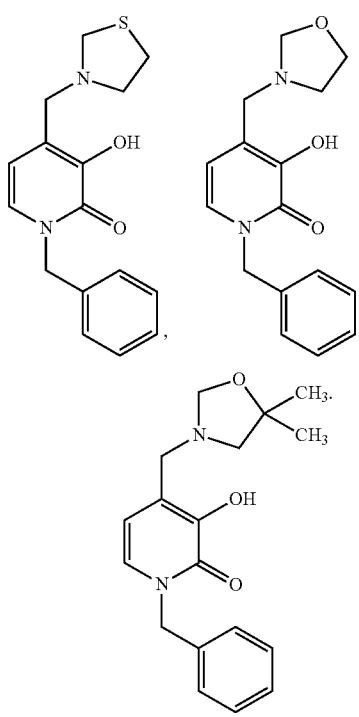
, and
Another embodiment of this aspect relates to HIF-1α prolyl hydroxylase inhibitors wherein $R^1$ and $R^2$ are taken together to form a substituted or unsubstituted $C_4$-$C_{11}$ heterocyclic or a substituted or unsubstituted $C_4$-$C_{11}$ heteroaryl ring, non-limiting examples of which are chosen from:
i)
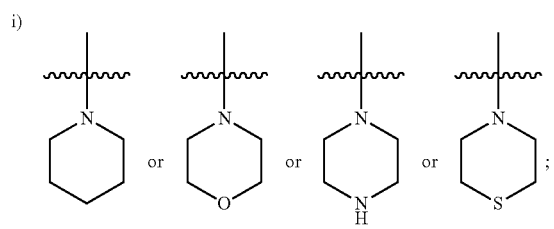
ii)
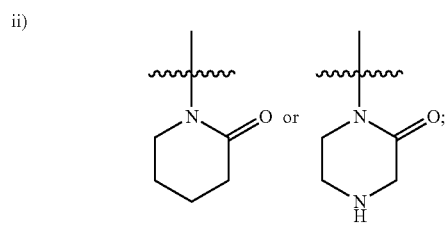
iii)
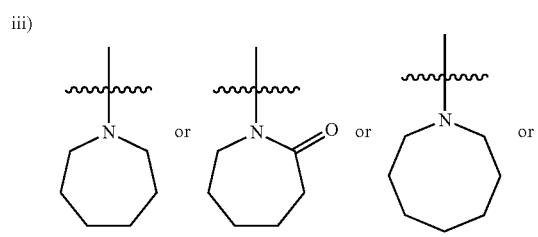
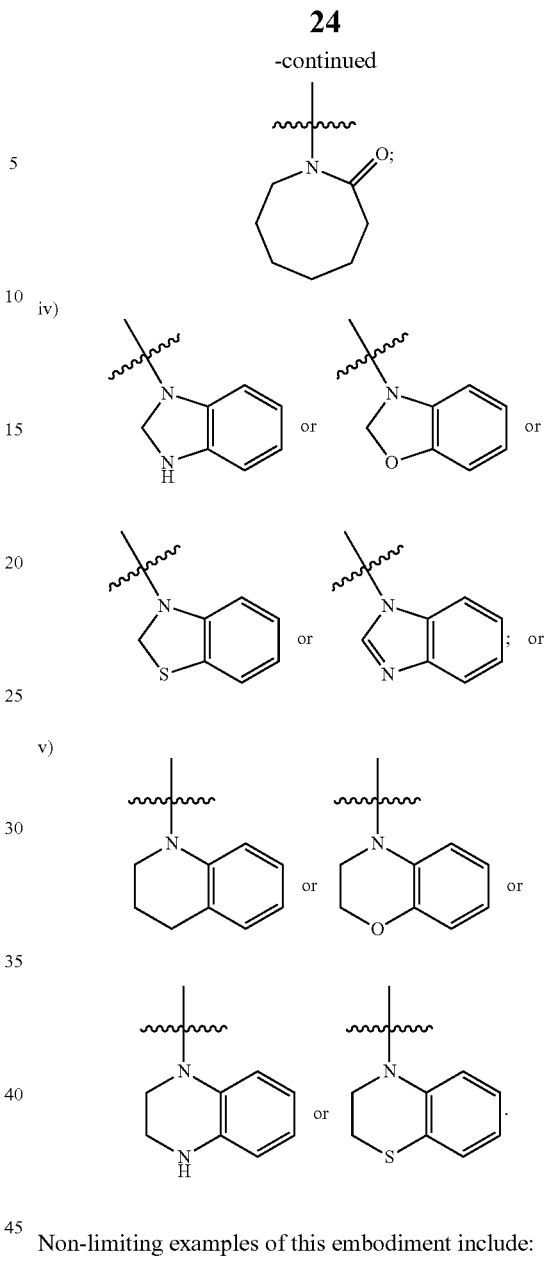
Non-limiting examples of this embodiment include:
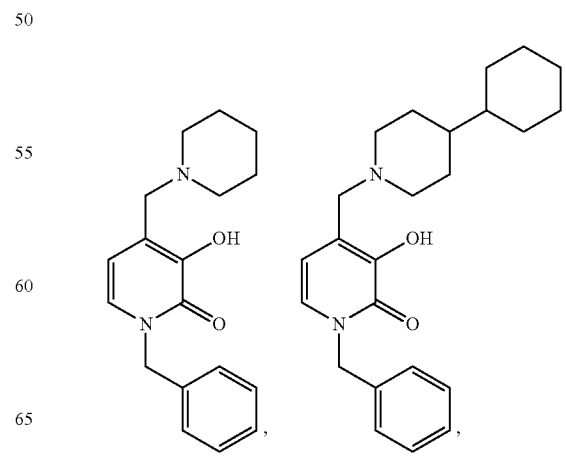

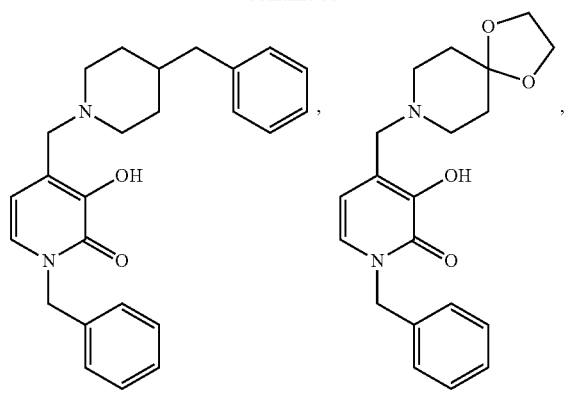

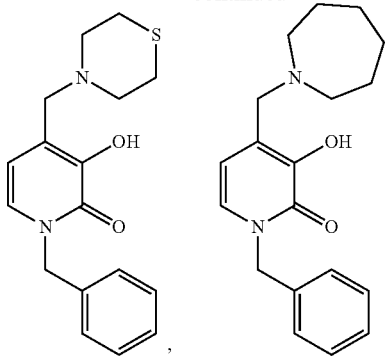

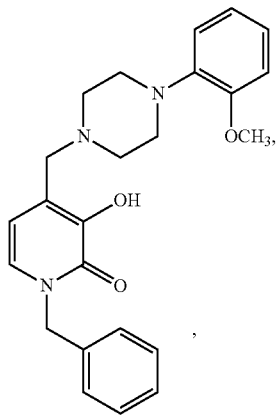

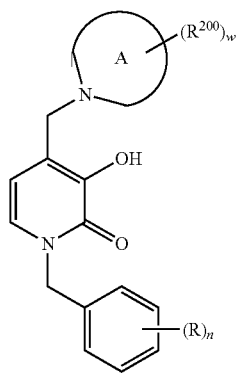

Another category of compounds has the formula:

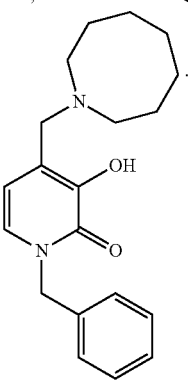

wherein $R^{200}$ and the index w are the same as defined herein above. R represents from 0 to 5 substitutions for hydrogen, wherein each R is independently chosen from:

i) $C_1$-$C_{12}$ substituted or unsubstituted linear, branched, or cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) $C_2$-$C_{12}$ substituted or unsubstituted linear, branched, or cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl (C$_4$), cyclobutenyl (C$_4$), cyclopentenyl (C$_5$), cyclopentadienyl (C$_5$), cyclohexenyl (C$_6$), 7-hydroxy-7-methyloct-4-en-2-yl (C$_9$), and 7-hydroxy-7-methyloct-3,5-dien-2-yl (C$_9$), and the like;

iii) C$_2$-C$_{12}$ substituted or unsubstituted linear or branched alkynyl; for example, ethynyl (C$_2$), prop-2-ynyl (also propargyl) (C$_3$), propyn-1-yl (C$_3$), 2-methyl-hex-4-yn-1-yl (C$_7$); 5-hydroxy-5-methylhex-3-ynyl (C$_7$), 6-hydroxy-6-methylhept-3-yn-2-yl (C$_8$), 5-hydroxy-5-ethylhept-3-ynyl (C$_9$), and the like;

iv) C$_6$ or C$_{10}$ substituted or unsubstituted aryl; for example, phenyl (C$_6$), naphthylen-1-yl (C$_{10}$), naphthylen-2-yl (C$_{10}$), 4-fluorophenyl (C$_6$), 2-hydroxyphenyl (C$_6$), 3-methylphenyl (C$_6$), 2-amino-4-fluorophenyl (C$_6$), 2-(N,N-diethylamino)phenyl (C$_6$), 2-cyanophenyl (C$_6$), 2,6-di-tert-butylphenyl (C$_6$), 3-methoxyphenyl (C$_6$), 8-hydroxynaphthylen-2-yl (C$_{10}$), 4,5-dimethoxynaphthylen-1-yl (C$_{10}$), 6-cyano-naphthylen-1-yl (C$_{10}$), and the like;

v) C$_1$-C$_9$ substituted or unsubstituted heterocyclic; for example, diazirinyl (C$_1$), aziridinyl (C$_2$), urazolyl (C$_2$), azetidinyl (C$_3$), pyrazolidinyl (C$_3$), imidazolidinyl (C$_3$), oxazolidinyl (C$_3$), isoxazolinyl (C$_3$), isoxazolyl (C$_3$), thiazolidinyl (C$_3$), isothiazolyl (C$_3$), isothiazolinyl (C$_3$), oxathiazolidinonyl (C$_3$), oxazolidinonyl (C$_3$), hydantoinyl (C$_3$), tetrahydropyranyl (C$_4$), pyrrolidinyl (C$_4$), morpholinyl (C$_4$), piperazinyl (C$_4$), piperidinyl (C$_4$), dihydropyranyl (C$_5$), tetrahydropyranyl (C$_5$), piperidin-2-onyl (valerolactam) (C$_5$), and the like;

vi) C$_1$-C$_{11}$ substituted or unsubstituted heteroaryl; for example, 1,2,3,4-tetrazolyl (C$_1$), [1,2,3]triazolyl (C$_2$), [1,2,4]triazolyl (C$_2$), triazinyl (C$_3$), thiazolyl (C$_3$), 1H-imidazolyl (C$_3$), oxazolyl (C$_3$), furanyl (C$_4$), thiopheneyl (C$_4$), pyrimidinyl (C$_4$), pyridinyl (C$_5$), and the like;

vii) halogen; for example, —F, —Cl, —Br, or —I;

viii) —[C(R$^{23a}$)(R$^{23b}$)]$_x$OR$^{10}$;
R$^{10}$ is chosen from:
a) —H;
b) C$_1$-C$_{12}$ substituted or unsubstituted linear, branched, or cyclic alkyl;
c) C$_6$ or C$_{10}$ substituted or unsubstituted aryl or alkylenearyl;
d) C$_1$-C$_9$ substituted or unsubstituted heterocyclic;
e) C$_1$-C$_{11}$ substituted or unsubstituted heteroaryl;
for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

ix) —[C(R$^{23a}$)(R$^{23b}$)]$_x$N(R$^{11a}$)(R$^{11b}$);
R$^{11a}$ and R$^{11b}$ are each independently chosen from:
a) —H;
b) —OR$^{12}$;
R$^{12}$ is hydrogen or C$_1$-C4 linear alkyl;
c) C$_1$-C$_{12}$ substituted or unsubstituted linear, branched, or cyclic alkyl;
d) C$_6$ or C$_{10}$ substituted or unsubstituted aryl;
e) C$_1$-C$_9$ substituted or unsubstituted heterocyclic;
f) C$_1$-C$_{11}$ substituted or unsubstituted heteroaryl; or
g) R$^{11a}$ and R$^{11b}$ can be taken together to form a substituted or unsubstituted ring having from 3 to 10 carbon atoms and from 0 to 3 heteroatoms chosen from oxygen, nitrogen, and sulfur;
for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;

x) —[C(R$^{23a}$)(R$^{23b}$)]$_x$C(O)R$^{13}$;
R$^{13}$ is:
a) C$_1$-C$_{12}$ substituted or unsubstituted linear, branched, or cyclic alkyl;
b) —OR$^{14}$;
R$^{14}$ is hydrogen, substituted or unsubstituted C$_1$-C$_4$ linear alkyl, C$_6$ or C$_{10}$ substituted or unsubstituted aryl, C$_1$-C$_9$ substituted or unsubstituted heterocyclic, C$_1$-C$_{11}$ substituted or unsubstituted heteroaryl;
c) —N(R$^{15a}$)(R$^{15b}$);
R$^{15a}$ and R$^{15b}$ are each independently hydrogen, C$_1$-C$_{12}$ substituted or unsubstituted linear, branched, or cyclic alkyl; C$_6$ or C$_{10}$ substituted or unsubstituted aryl; C$_1$-C$_9$ substituted or unsubstituted heterocyclic; C$_1$-C$_{11}$ substituted or unsubstituted heteroaryl; or R$^{15a}$ and R$^{15b}$ can be taken together to form a substituted or unsubstituted ring having from 3 to 10 carbon atoms and from 0 to 3 heteroatoms chosen from oxygen, nitrogen, and sulfur;
for example, —COCH$_3$, —CH$_2$COCH$_3$, —OCH$_2$CH$_3$, —CH$_2$COCH$_2$CH$_3$, —COCH$_2$CH$_3$, —CH$_2$COCH$_2$CH$_2$CH$_3$, and the like;

xi) —[C(R$^{23a}$)(R$^{23b}$)]$_x$OC(O)R$^{16}$;
R$^{16}$ is:
a) C$_1$-C$_{12}$ substituted or unsubstituted linear, branched, or cyclic alkyl;
b) —N(R$^{17a}$)(R$^{17b}$);
R$^{17a}$ and R$^{17b}$ are each independently hydrogen, C$_1$-C$_{12}$ substituted or unsubstituted linear, branched, or cyclic alkyl; C$_6$ or C$_{10}$ substituted or unsubstituted aryl; C$_1$-C$_9$ substituted or unsubstituted heterocyclic; C$_1$-C$_{11}$ substituted or unsubstituted heteroaryl; or R$^{17a}$ and R$^{17b}$ can be taken together to form a substituted or unsubstituted ring having from 3 to 10 carbon atoms and from 0 to 3 heteroatoms chosen from oxygen, nitrogen, and sulfur;

xii) —[C(R$^{23a}$)(R$^{23b}$)]$_x$NR$^{18}$C(O)R$^{19}$;
R$^{18}$ is:
a) —H; or
b) C$_1$-C$_4$ substituted or unsubstituted linear, branched, or cyclic alkyl;
R$^{19}$ is:
a) C$_1$-C$_{12}$ substituted or unsubstituted linear, branched, or cyclic alkyl;
b) —N(R$^{20a}$)(R$^{20b}$);
R$^{20a}$ and R$^{20b}$ are each independently hydrogen, C$_1$-C$_{12}$ substituted or unsubstituted linear, branched, or cyclic alkyl; C$_6$ or C$_{10}$ substituted or unsubstituted aryl; C$_1$-C$_9$ substituted or unsubstituted heterocyclic; C$_1$-C$_{11}$ substituted or unsubstituted heteroaryl; or R$^{20a}$ and R$^{20b}$ can be taken together to form a substituted or unsubstituted ring having from 3 to 10 carbon atoms and from 0 to 3 heteroatoms chosen from oxygen, nitrogen, and sulfur;
for example, —NHC(O)CH$_3$, —CH$_2$NHC(O)CH$_3$, —NHC(O)NH$_2$, —CH$_2$NHC(O)NH$_2$, —NHC(O)NHCH$_3$, —CH$_2$NHC(O)NHCH$_3$, —OC(O)N(CH$_3$)$_2$, —CH$_2$NHC(O)N(CH$_3$)$_2$, and the like;

xiii) —[C(R$^{23a}$)(R$^{23b}$)]$_x$CN; for example; —CN, —CH$_2$CN, and —CH$_2$CH$_2$CN;

xiv) —[C(R$^{23a}$)(R$^{23b}$)]$_x$NO$_2$; for example; —NO$_2$, —CH$_2$NO$_2$, and —CH$_2$CH$_2$NO$_2$;

xv) —[C(R$^{23a}$)(R$^{23b}$)]$_x$R$^{21}$; for example, —CH$_2$F, —CHF$_2$, —CF$_3$, —CCl$_3$, or —CBr$_3$;
R$^{21}$ is C$_1$-C$_{10}$ linear, branched, or cyclic alkyl substituted by from 1 to 21 halogen atoms chosen from —F, —Cl, —Br, or —I;

xvi) —[C(R$^{23a}$)(R$^{23b}$)]$_x$SO$_2$R$^{22}$;

$R^{22}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl; for example, —$SO_2H$, —$CH_2SO_2H$, —$SO_2CH_3$, —$CH_2SO_2CH_3$, —$SO_2C_6H_5$, and —$CH_2SO_2C_6H_5$;

$R^{23a}$ and $R^{23b}$ are each independently hydrogen or $C_1$-$C_4$ alkyl; and the index x is an integer from 0 to 5.

Non-limiting examples of this category include compounds having the formula:

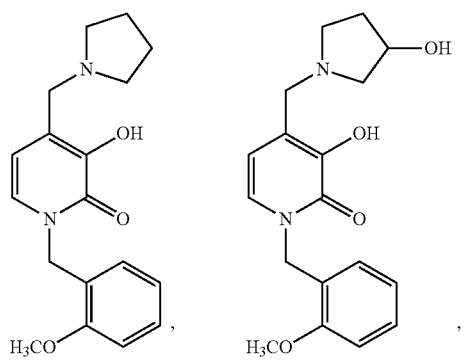

,

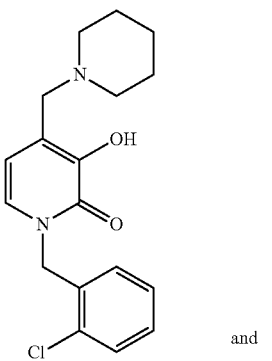

and

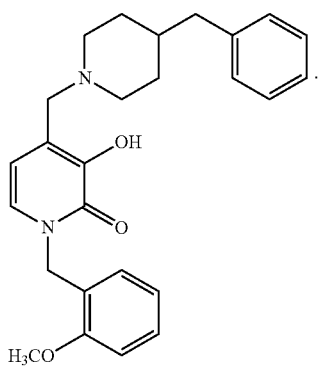

.

A further category of compounds relates to unsubstituted N-benzyl-4-aminomethyl-3-hydroxypyridin-2-(1H)-ones having the formula:

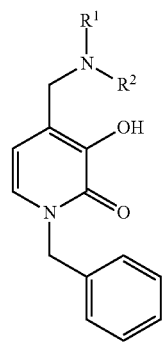

wherein $R^1$ and $R^2$ are each independently chosen from:
i) hydrogen;
ii) substituted or unsubstituted $C_1$-$C_{10}$ linear, branched, or cyclic alkyl;
iii) substituted or unsubstituted $C_2$-$C_{10}$ linear, branched, or cyclic alkenyl;
iv) substituted or unsubstituted $C_2$-$C_{10}$ linear or branched alkynyl;
v) substituted or unsubstituted $C_6$ or $C_{10}$ aryl;
vi) substituted or unsubstituted $C_1$-$C_9$ heterocyclic; or
vii) substituted or unsubstituted $C_1$-$C_9$ heteroaryl.

The first aspect of this category relates to HIF-1α prolyl hydroxylase inhibitors wherein $R^2$ is hydrogen and $R^1$ is substituted or unsubstituted $C_1$-$C_9$ heterocyclic or $C_1$-$C_9$ heteroaryl. In a first embodiment, $R^1$ is a substituted heterocyclic group, non-limiting examples of which include aziridinyl ($C_2$), azetidinyl ($C_3$), pyrrolidinyl ($C_4$), morpholinyl ($C_4$), piperazinyl ($C_4$), piperidinyl ($C_4$), piperidin-2-onyl (valerolactam) ($C_5$), and azepan-2-only (caprolactam) ($C_6$), wherein the $R^1$ unit can be bonded to the nitrogen atom at any position in the ring. In addition, the $C_1$-$C_9$ heterocyclic or $C_1$-$C_9$ heteroaryl ring can be substituted at any position whether a ring carbon or a ring heteroatom, for example, a ring nitrogen. Non-limiting examples of this embodiment include:

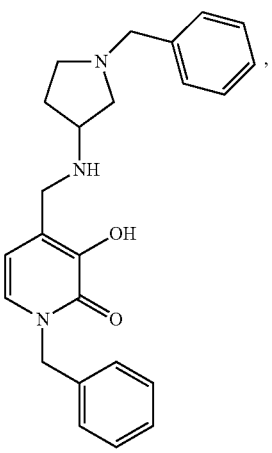

-continued

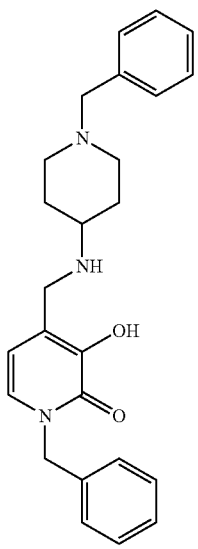
and
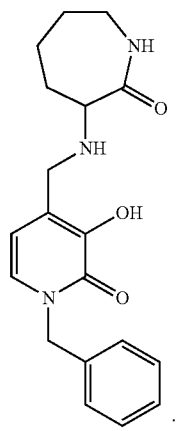
.

In another embodiment, $R^2$ is hydrogen and $R^1$ is substituted or unsubstituted $C_3$-$C_{12}$ cycloalkyl wherein the cycloalkyl ring can be substituted at any ring position. Non-limiting examples of this embodiment include:

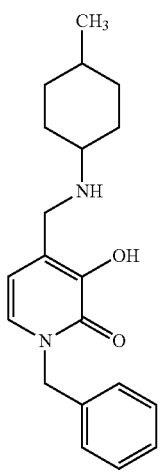
and
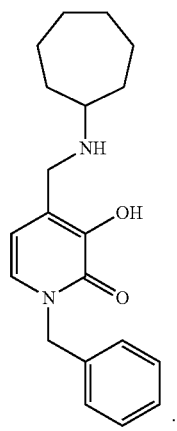
.

A yet further category of compounds relates to unsubstituted N-benzyl-4-aminomethyl-3-hydroxypyridin-2-(1H)-ones having the formula:

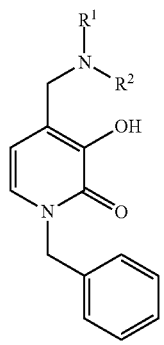

$R^1$ and $R^2$ are each independently hydrogen or substituted or unsubstituted $C_1$-$C_{10}$ linear or branched alkyl, wherein the alkyl unit can be substituted by one or more units independently chosen from:

i) $C_1$-$C_8$ linear, branched, or cyclic alkoxy;

ii) hydroxy;

iii) halogen;

iv) cyano;

v) amino, $C_1$-$C_8$ mono-alkylamino, $C_1$-$C_8$ di-alkylamino;

vi) —$SR^{40}$; $R^{40}$ is hydrogen or $C_1$-$C_4$ linear or branched alkyl;

vii) substituted or unsubstituted $C_6$ of $C_{10}$ aryl;

viii) substituted or unsubstituted $C_1$-$C_9$ heterocyclic; or ix) substituted or unsubstituted $C_1$-$C_9$ heteroaryl.

Non-limiting examples of this category include:

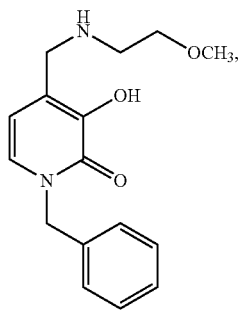
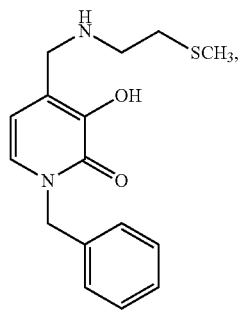

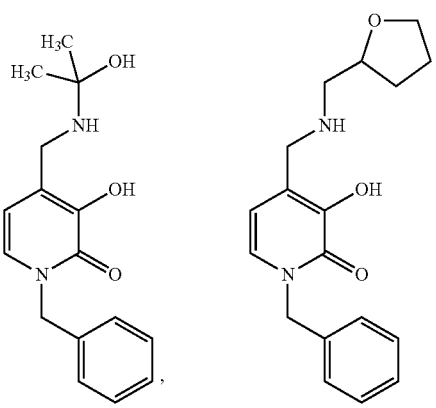

,

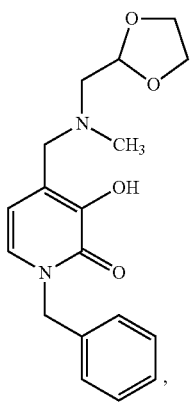
,
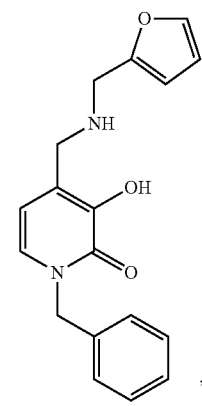
,

-continued

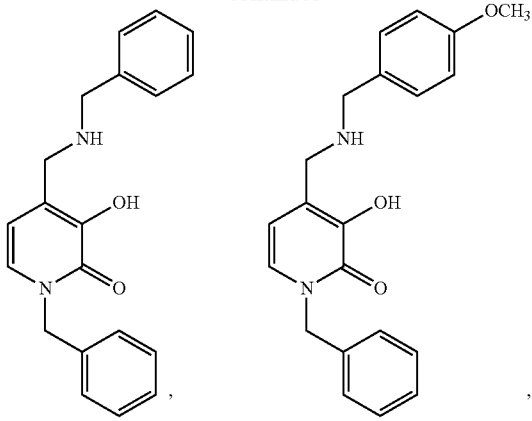

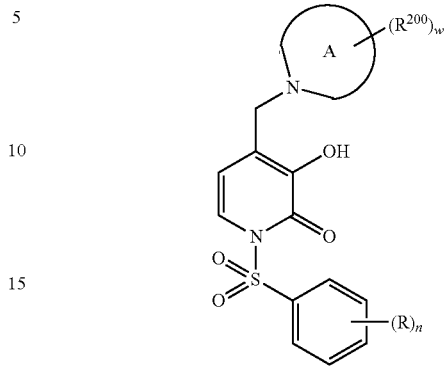

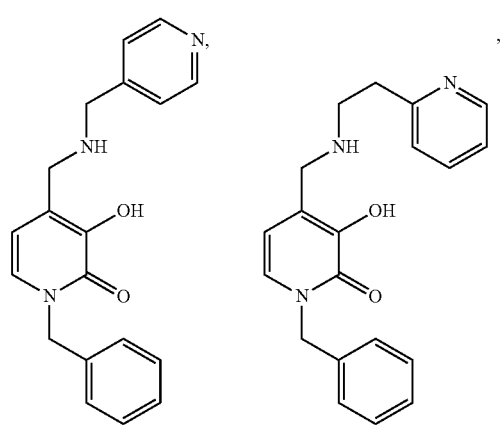

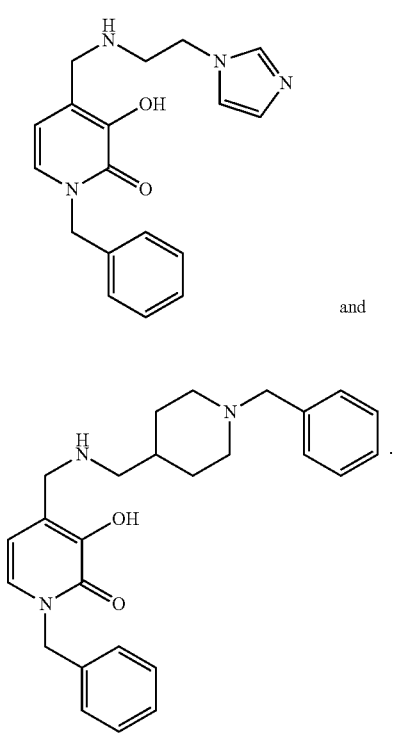

and

A still further category of the disclosed compounds has the formula:

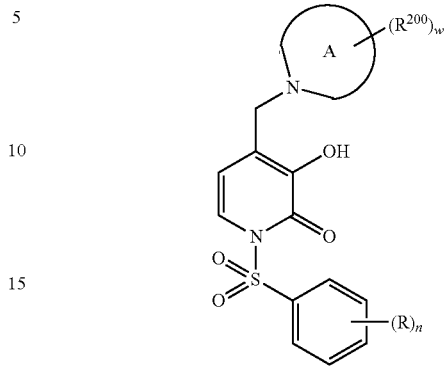

wherein $R^{200}$ and the index w are the same as defined herein above. R represents from 0 to 5 substitutions for hydrogen, wherein each R is independently chosen from:

i) substituted or unsubstituted $C_1$-$C_{12}$ linear, $C_3$-$C_{12}$ branched, or $C_3$-$C_{12}$ cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethyl-hept-3-ynyl ($C_9$), and the like;

iv) substituted or unsubstituted $C_6$ or $C_{10}$ aryl; for example, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-cyano-naphthylen-1-yl ($C_{10}$), and the like;

v) substituted or unsubstituted $C_1$-$C_9$ heterocyclic; for example, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydropyranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), and the like;

vi) substituted or unsubstituted $C_1$-$C_{11}$ heteroaryl; for example, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), pyridinyl ($C_5$), and the like;
vii) halogen; for example, —F, —Cl, —Br, or —I;
viii) —[C($R^{23a}$)($R^{23b}$)]$_x$O$R^{10}$;
$R^{10}$ is chosen from:
a) —H;
b) substituted or unsubstituted $C_1$-$C_{12}$ linear, $C_3$-$C_{12}$ branched, or $C_3$-$C_{12}$ cyclic alkyl;
c) substituted or unsubstituted $C_6$ or $C_{10}$ aryl or $C_7$ or $C_{10}$ alkylenearyl;
d) substituted or unsubstituted $C_1$-$C_9$ heterocyclic;
e) substituted or unsubstituted $C_1$-$C_{11}$ heteroaryl;
for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
ix) —[C($R^{23a}$)($R^{23b}$)]$_x$N($R^{11a}$)($R^{11b}$);
$R^{11a}$ and $R^{11b}$ are each independently chosen from:
a) —H;
b) —O$R^{12}$;
$R^{12}$ is hydrogen or $C_1$-C4 linear alkyl;
c) substituted or unsubstituted $C_1$-$C_{12}$ linear, $C_3$-$C_{12}$ branched, or $C_3$-$C_{12}$ cyclic alkyl;
d) substituted or unsubstituted $C_6$ or $C_{10}$ aryl;
e) substituted or unsubstituted $C_1$-$C_9$ heterocyclic;
f) substituted or unsubstituted $C_1$-$C_{11}$ heteroaryl; or
g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;
for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;
x) —[C($R^{23a}$)($R^{23b}$)]$_x$C(O)$R^{13}$;
$R^{13}$ is:
a) substituted or unsubstituted $C_1$-$C_{12}$ linear, $C_3$-$C_{12}$ branched, or $C_3$-$C_{12}$ cyclic alkyl;
b) —O$R^{14}$;
$R^{14}$ is hydrogen, substituted or unsubstituted $C_1$-$C_4$ linear alkyl, substituted or unsubstituted $C_6$ or $C_{10}$ aryl, substituted or unsubstituted $C_1$-$C_9$ heterocyclic, substituted or unsubstituted $C_1$-$C_{11}$ heteroaryl;
c) —N($R^{15a}$)($R^{15b}$);
$R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;
for example, —COCH$_3$, —CH$_2$COCH$_3$, —OCH$_2$CH$_3$, —CH$_2$COCH$_2$CH$_3$, —COCH$_2$CH$_2$CH$_3$, —CH$_2$COCH$_2$CH$_2$CH$_3$, and the like;
xi) —[C($R^{23a}$)($R^{23b}$)]$_x$OC(O)$R^{16}$;
$R^{16}$ is:
a) substituted or unsubstituted $C_1$-$C_{12}$ linear, $C_3$-$C_{12}$ branched, or $C_3$-$C_{12}$ cyclic alkyl;
b) —N($R^{17a}$)($R^{17b}$);
$R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;
xii) —[C($R^{23a}$)($R^{23b}$)]$_x$N$R^{18}$C(O)$R^{19}$;
$R^{18}$ is:
a) —H; or
b) substituted or unsubstituted $C_1$-$C_4$ linear, $C_3$-$C_4$ branched, or $C_3$-$C_4$ cyclic alkyl;
$R^{19}$ is:
a) substituted or unsubstituted $C_1$-$C_{12}$ linear, $C_3$-$C_{12}$ branched, or $C_3$-$C_{12}$ cyclic alkyl;
b) —N($R^{20a}$)($R^{20b}$);
$R^{20a}$ and $R^{20b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;
for example, —NHC(O)CH$_3$, —CH$_2$NHC(O)CH$_3$, —NHC(O)NH$_2$, —CH$_2$NHC(O)NH$_2$, —NHC(O)NHCH$_3$, —CH$_2$NHC(O)NHCH$_3$, —OC(O)N(CH$_3$)$_2$, —CH$_2$NHC(O)N(CH$_3$)$_2$, and the like;
xiii) —[C($R^{23a}$)($R^{23b}$)]$_x$CN; for example; —CN, —CH$_2$CN, and —CH$_2$CH$_2$CN;
xiv) —[C($R^{23a}$)($R^{23b}$)]$_x$NO$_2$; for example; —NO$_2$, —CH$_2$NO$_2$, and —CH$_2$CH$_2$NO$_2$;
xv) —[C($R^{23a}$)($R^{23b}$)]$_x$$R^{21}$; for example, —CH$_2$F, —CHF$_2$, —CF$_3$, —CCl$_3$, or —CBr$_3$;
$R^{21}$ is $C_1$-$C_{10}$ linear, branched, or cyclic alkyl substituted by from 1 to 21 halogen atoms chosen from —F, —Cl, —Br, or —I;
xvi) —[C($R^{23a}$)($R^{23b}$)]$_x$SO$_2$$R^{22}$;
$R^{22}$ is hydrogen, hydroxyl, substituted or unsubstituted $C_1$-$C_4$ linear or $C_3$-$C_4$ branched alkyl; substituted or unsubstituted $C_6$, $C_{10}$, or $C_{14}$ aryl; $C_7$-$C_{15}$ alkylenearyl; substituted or unsubstituted $C_1$-$C_9$ heterocyclic; or substituted or unsubstituted $C_1$-$C_{11}$ heteroaryl; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$;
$R^{23a}$ and $R^{23b}$ are each independently hydrogen or $C_1$-$C_4$ alkyl; and
the index x is an integer from 0 to 5.

One aspect embodiment of this category relates to HIF-1α prolyl hydroxylase inhibitors wherein $R^1$ and $R^2$ are taken together to form a 5-member substituted or unsubstituted $C_1$-$C_4$ heterocyclic or a substituted or unsubstituted $C_1$-$C_4$ heteroaryl ring, non-limiting examples of which include a ring chosen from:

i) 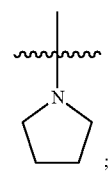
;

ii) 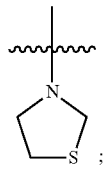

ii) 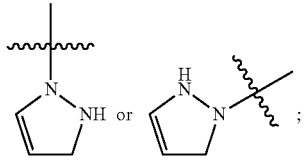

iii) 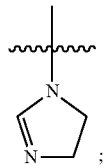

iv) 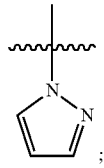

v) 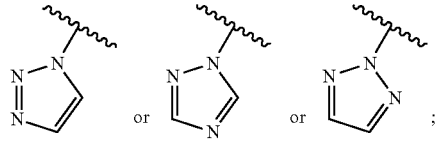

vi) 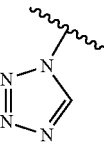

vii) 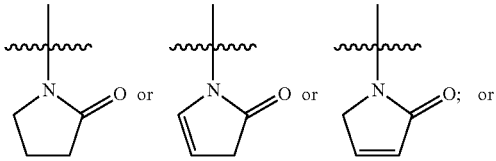

viii) 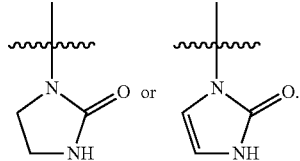

Another aspect of this category relates to HIF-1α prolyl hydroxylase inhibitors wherein $R^1$ and $R^2$ are taken together to form a substituted or unsubstituted $C_4$-$C_{11}$ heterocyclic or a substituted or unsubstituted $C_4$-$C_{11}$ heteroaryl ring, non-limiting examples of which are chosen from:

i) 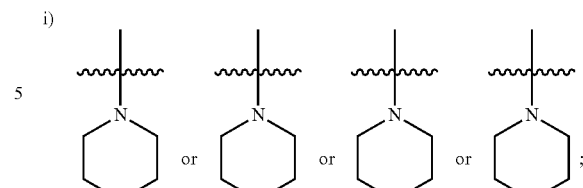

ii) 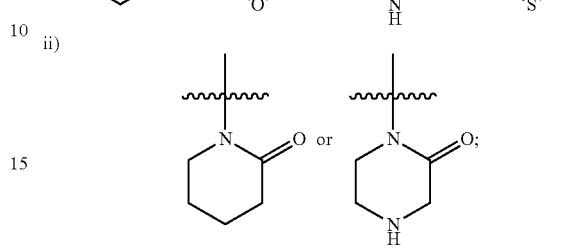

iii) 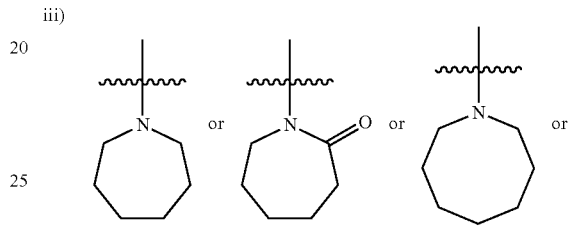

iv) 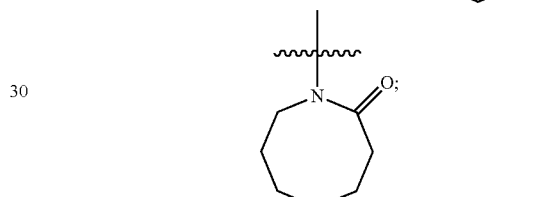

v) 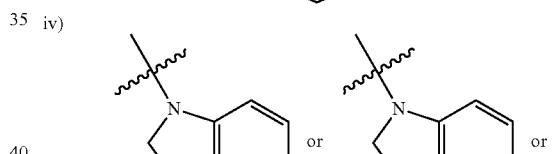

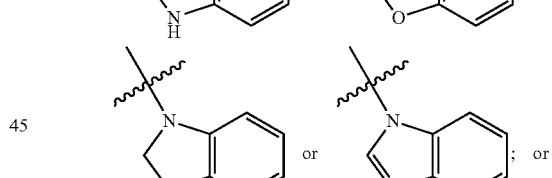

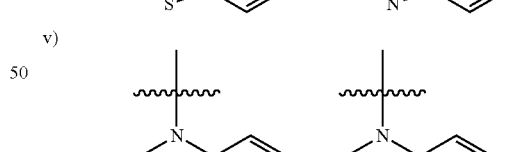

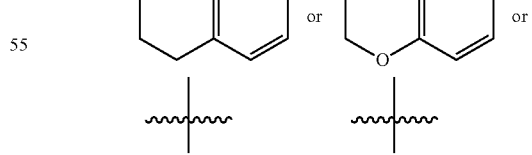

Non-limiting examples of this category include compounds having the formula:

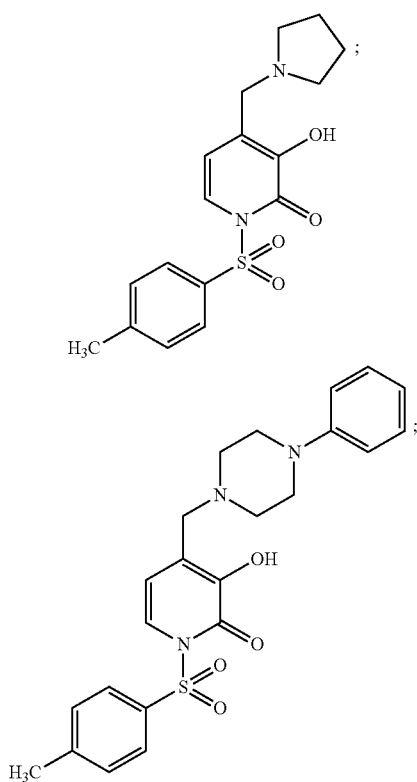
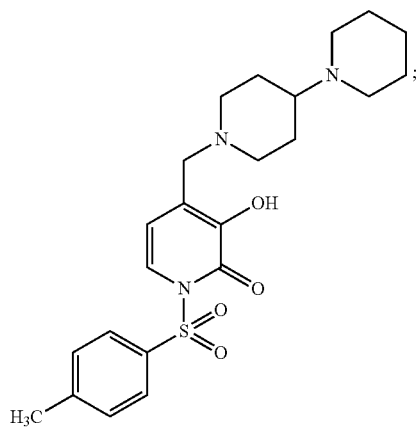
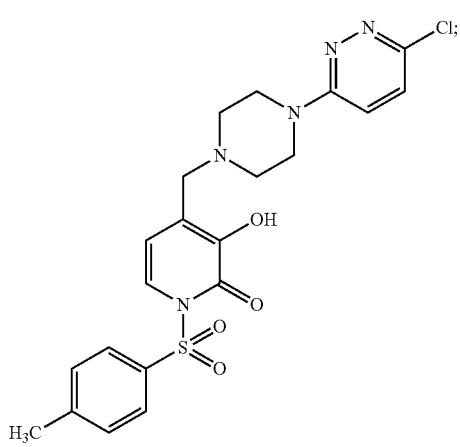
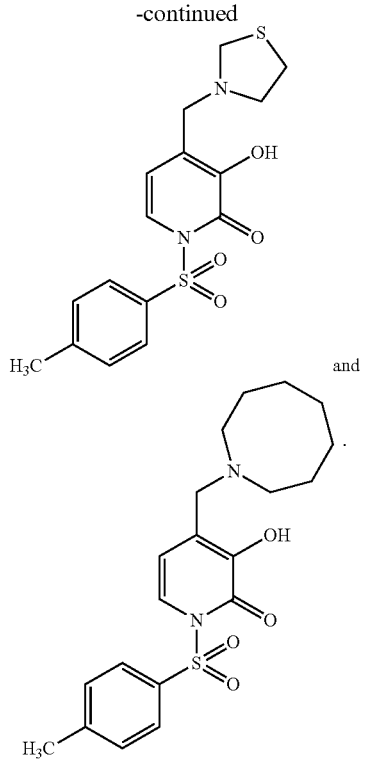

A further category of the disclosed compounds has the formula:

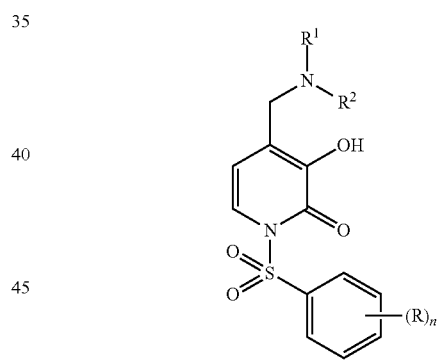

wherein R represents from 1 to 5 optional substitutions for a phenyl ring hydrogen atom, $R^1$ and $R^2$ are each independently hydrogen or substituted or unsubstituted $C_1$-$C_{10}$ linear or branched alkyl, wherein the alkyl unit can be substituted by one or more units independently chosen from:

i) $C_1$-$C_8$ linear, $C_3$-$C_8$ branched, or $C_3$-$C_8$ cyclic alkoxy;
ii) hydroxy;
iii) halogen;
iv) cyano;
v) amino, $C_1$-$C_8$ mono-alkylamino, $C_1$-$C_8$ di-alkylamino;
vi) —$SR^{40}$; $R^{40}$ is hydrogen or $C_1$-$C_4$ linear or branched alkyl;
vii) substituted or unsubstituted $C_6$ of $C_{10}$ aryl;
viii) substituted or unsubstituted $C_1$-$C_9$ heterocyclic; or
ix) substituted or unsubstituted $C_1$-$C_9$ heteroaryl.

Non-limiting examples of this category include:

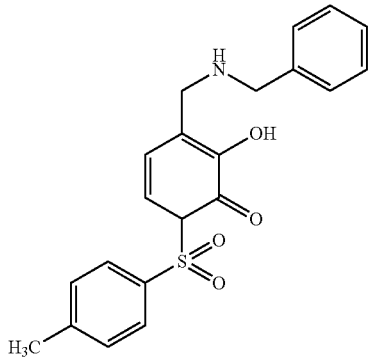

and

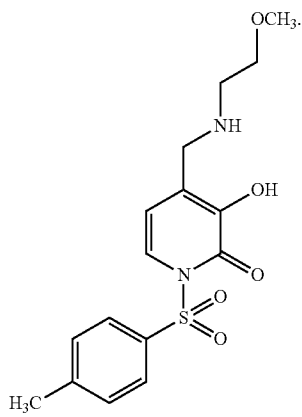

A still yet further category of the disclosed HIF-1α prolyl hydroxylase inhibitors relates to compounds having the formula:

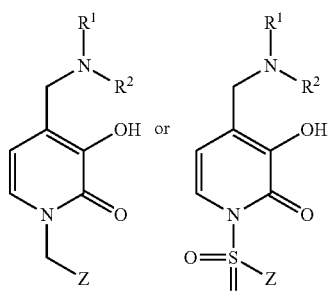

wherein $R^1$ and $R^2$ are taken together to form a substituted or unsubstituted piperazine ring, the substitutions on the ring as defined for $R^{200}$ herein above.

A yet still further category of the disclosed HIF-1α prolyl hydroxylase inhibitors have the formula:

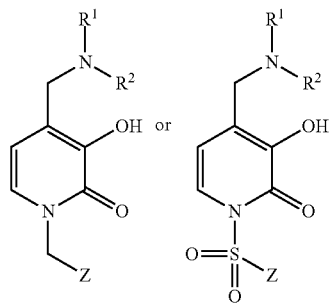

wherein $R^1$ and $R^2$ can be taken together to form a substituted or unsubstituted heterocyclic or heteroaryl ring having from 2 to 20 carbon atoms and from 1 to 7 heteroatoms wherein the rings formed exclude a piperazine ring.

Also disclosed herein are N-substituted benzyl or N-substituted sulfonylaryl-3-hydroxypyridin-2-(1H)-ones having the formula:

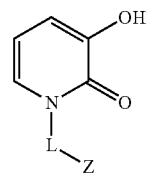

that can be used to stimulate the cellular immune response in a subject. For these compounds, Z and L are the same as disclosed herein above. Non-limiting examples of these compounds include:

1-(4-chlorobenzyl)-3-hydroxypyridin-2(1H)-one having the formula:

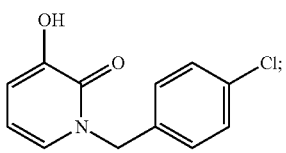

1-(3-chlorobenzyl)-3-hydroxypyridin-2(1H)-one having the formula:

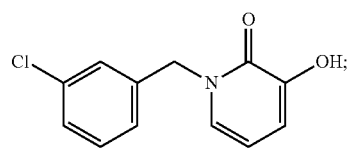

and 1-(2-chlorobenzyl)-3-hydroxypyridin-2(1H)-one having the formula:

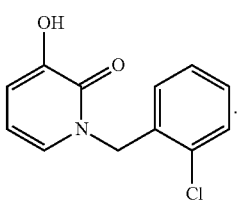

Further disclosed herein are N-substituted benzyl or N-substituted sulfonylaryl-5-substituted-3-hydroxypyridin-2-(1H)-ones having the formula:

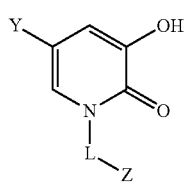

wherein Y is substituted or unsubstituted phenyl, Z and L are the same as defined herein above.

One aspect of Y relates to a phenyl group that is substituted with from 1 to 5 halogen atoms, for example, Y is chosen from 2-chlorophenyl, 3-chlorophenyl, 2-fluorophenyl, 3-fluorophenyl, or 4-fluorophenyl. A further aspect of Y units relates to compounds wherein Y is chosen from 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, and 2,6-dichlorophenyl.

A non-limiting example of compounds according to this category include 1-(4-chlorobenzyl)-5-(4-chlorophenyl)-3-hydroxypyridin-2(1H)-one having the formula:

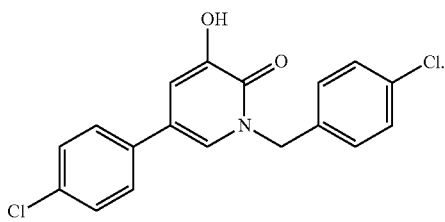

Further non-limiting examples include:
1-(2-chlorobenzyl)-5-(2-chlorophenyl)-3-hydroxypyridin-2(1H)-one;
1-(2-chlorobenzyl)-5-(3-chlorophenyl)-3-hydroxypyridin-2(1H)-one;
1-(2-chlorobenzyl)-5-(4-chlorophenyl)-3-hydroxypyridin-2(1H)-one;
1-(3-chlorobenzyl)-5-(2-chlorophenyl)-3-hydroxypyridin-2(1H)-one;
1-(3-chlorobenzyl)-5-(3-chlorophenyl)-3-hydroxypyridin-2(1H)-one;
1-(3-chlorobenzyl)-5-(4-chlorophenyl)-3-hydroxypyridin-2(1H)-one;
1-(4-chlorobenzyl)-5-(2-chlorophenyl)-3-hydroxypyridin-2(1H)-one;
1-(4-chlorobenzyl)-5-(3-chlorophenyl)-3-hydroxypyridin-2(1H)-one;
1-(2-fluorobenzyl)-5-(2-chlorophenyl)-3-hydroxypyridin-2(1H)-one;
1-(2-fluorobenzyl)-5-(3-chlorophenyl)-3-hydroxypyridin-2(1H)-one;
1-(2-fluorobenzyl)-5-(4-chlorophenyl)-3-hydroxypyridin-2(1H)-one;
1-(3-fluorobenzyl)-5-(2-chlorophenyl)-3-hydroxypyridin-2(1H)-one;
1-(3-fluorobenzyl)-5-(3-chlorophenyl)-3-hydroxypyridin-2(1H)-one;
1-(3-fluorobenzyl)-5-(4-chlorophenyl)-3-hydroxypyridin-2(1H)-one;
1-(4-fluorobenzyl)-5-(2-chlorophenyl)-3-hydroxypyridin-2(1H)-one;
1-(4-fluorobenzyl)-5-(3-chlorophenyl)-3-hydroxypyridin-2(1H)-one
1-(4-fluorobenzyl)-5-(4-chlorophenyl)-3-hydroxypyridin-2(1H)-one
1-(2-chlorobenzyl)-5-(2-fluorophenyl)-3-hydroxypyridin-2(1H)-one;
1-(2-chlorobenzyl)-5-(3-fluorophenyl)-3-hydroxypyridin-2(1H)-one;
1-(2-chlorobenzyl)-5-(4-fluorophenyl)-3-hydroxypyridin-2(1H)-one;
1-(3-chlorobenzyl)-5-(2-fluorophenyl)-3-hydroxypyridin-2(1H)-one;
1-(3-chlorobenzyl)-5-(3-fluorophenyl)-3-hydroxypyridin-2(1H)-one;
1-(3-chlorobenzyl)-5-(4-fluorophenyl)-3-hydroxypyridin-2(1H)-one;
1-(4-chlorobenzyl)-5-(2-fluorophenyl)-3-hydroxypyridin-2(1H)-one;
1-(4-chlorobenzyl)-5-(3-fluorophenyl)-3-hydroxypyridin-2(1H)-one;
1-(4-chlorobenzyl)-5-(3-fluorophenyl)-3-hydroxypyridin-2(1H)-one
1-(2-fluorobenzyl)-5-(2-fluorophenyl)-3-hydroxypyridin-2(1H)-one;
1-(2-fluorobenzyl)-5-(3-fluorophenyl)-3-hydroxypyridin-2(1H)-one;
1-(2-fluorobenzyl)-5-(4-fluorophenyl)-3-hydroxypyridin-2(1H)-one;
1-(3-fluorobenzyl)-5-(2-fluorophenyl)-3-hydroxypyridin-2(1H)-one;
1-(3-fluorobenzyl)-5-(3-fluorophenyl)-3-hydroxypyridin-2(1H)-one;
1-(3-fluorobenzyl)-5-(4-fluorophenyl)-3-hydroxypyridin-2(1H)-one;
1-(4-fluorobenzyl)-5-(2-fluorophenyl)-3-hydroxypyridin-2(1H)-one;
1-(4-fluorobenzyl)-5-(3-fluorophenyl)-3-hydroxypyridin-2(1H)-one; and
1-(4-fluorobenzyl)-5-(3-fluorophenyl)-3-hydroxypyridin-2(1H)-one.

The disclosed compounds are organized into several categories for the strictly non-limiting purpose of describing alternatives for synthetic strategies for the preparation of subgenera of compounds within the scope of the disclosed compounds that are not expressly exemplified herein. This mental organization into categories does not imply anything with respect to increased or decreased biological efficacy with respect to any of the compounds or compositions of matter described herein.

Category I of the disclosed HIF-1α prolyl hydroxylase inhibitors relates to compounds having the formula:

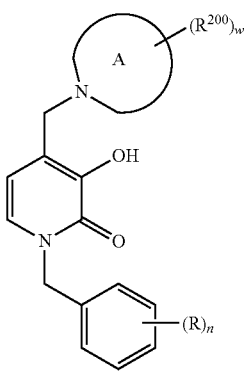

wherein A is a substituted or unsubstituted heterocyclic or heteroaryl ring having from 2 to 20 carbon atoms and from 1 to 7 heteroatoms, $R^{200}$ represents from 0 to 40 substitutions form hydrogen, R represents from 1 to 5 substitutions for hydrogen as defined herein above, and the index n is from 1 to 5. Table I provides representative examples of compounds according to this category.

TABLE I

| No. | R | A ring |
|---|---|---|
| A1 | 3-methoxy | pyrrolidin-1-yl |
| A2 | 3-methoxy | 3-hydroxypyrrolidin-1-yl |
| A3 | 3-methoxy | 2-(pyrdin-2-yl)pyrrolidin-1-yl |
| A4 | 3-methoxy | 2-methylcarboxypyrrolidin-1-yl |
| A5 | 3-methoxy | 2-(methoxymethyl)pyrrolidin-1-yl |
| A6 | 3-methoxy | thiazolidin-3-yl |
| A7 | 3-methoxy | 1H-imidazol-1-yl |
| A8 | 3-methoxy | piperidin-1-yl |
| A9 | 3-methoxy | 4-benzylpiperidin-1-yl |
| A10 | 3-methoxy | 1,4'-bipiperidinyl-1'-yl |
| A11 | 3-methoxy | piperazin-1-yl |
| A12 | 3-methoxy | 4-benzylpiperazin-1-yl |
| A13 | 3-methoxy | 4-(2-methoxyphenyl)piperazin-1-ylmethyl |
| A14 | 3-methoxy | 4-(6-chloropyridazin-3-yl)piperazin-1-yl |
| A15 | 3-methoxy | 1,4-dioxa-8-azaspiro[4,5]dec-8-yl |
| A16 | 3-methoxy | morpholin-4-yl |
| A17 | 3-methoxy | thiomorpholin-4-yl |
| A18 | 3-methoxy | azepan-1-yl |
| A19 | 3-methoxy | azocan-1-yl |
| A20 | 3-methoxy | 3,4-dihydroquinolin-1(2H)-yl |
| A21 | 4-chloro | pyrrolidin-1-yl |
| A22 | 4-chloro | 3-hydroxypyrrolidin-1-yl |
| A23 | 4-chloro | 2-(pyrdin-2-yl)pyrrolidin-1-yl |
| A24 | 4-chloro | 2-methylcarboxypyrrolidin-1-yl |
| A25 | 4-chloro | 2-(methoxymethyl)pyrrolidin-1-yl |
| A26 | 4-chloro | thiazolidin-3-yl |
| A27 | 4-chloro | 1H-imidazol-1-yl |
| A28 | 4-chloro | piperidin-1-yl |
| A29 | 4-chloro | 4-benzylpiperidin-1-yl |
| A30 | 4-chloro | 1,4'-bipiperidinyl-1'-yl |
| A31 | 4-chloro | piperazin-1-yl |
| A32 | 4-chloro | 4-benzylpiperazin-1-yl |
| A33 | 4-chloro | 4-(2-methoxyphenyl)piperazin-1-ylmethyl |
| A34 | 4-chloro | 4-(6-chloropyridazin-3-yl)piperazin-1-yl |
| A35 | 4-chloro | 1,4-dioxB-8-azaspiro[4,5]dec-8-yl |
| A36 | 4-chloro | morpholin-4-yl |
| A37 | 4-chloro | thiomorpholin-4-yl |
| A38 | 4-chloro | azepan-1-yl |
| A39 | 4-chloro | azocan-1-yl |
| A40 | 4-chloro | 3,4-dihydroquinolin-1(2H)-yl |
| A41 | 4-chloro | 4-tert-butoxycarbonylpiperazin-1-yl |

The disclosed compounds of this category can be prepared by the procedure outlined herein below in Scheme I and described in Example 1.

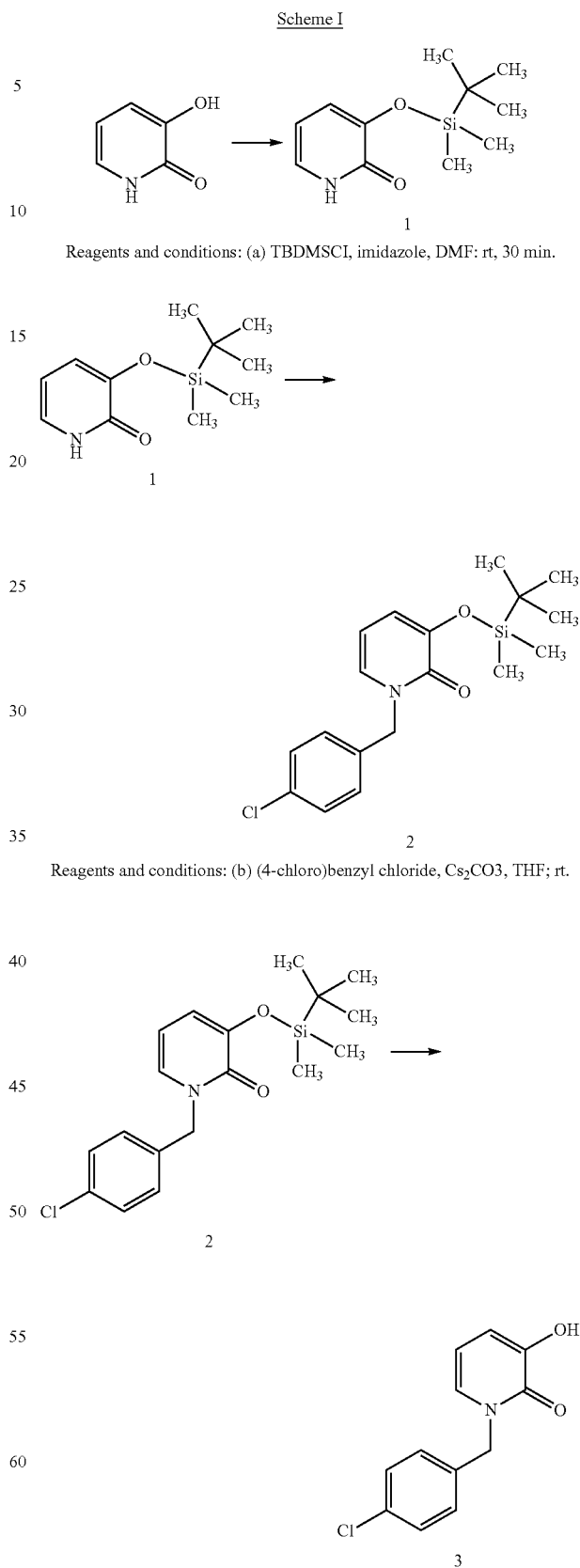

Scheme I

Reagents and conditions: (a) TBDMSCl, imidazole, DMF: rt, 30 min.

Reagents and conditions: (b) (4-chloro)benzyl chloride, $Cs_2CO3$, THF; rt.

Reagents and conditions: (c) 5 M HCl, EtOH; 30 min.

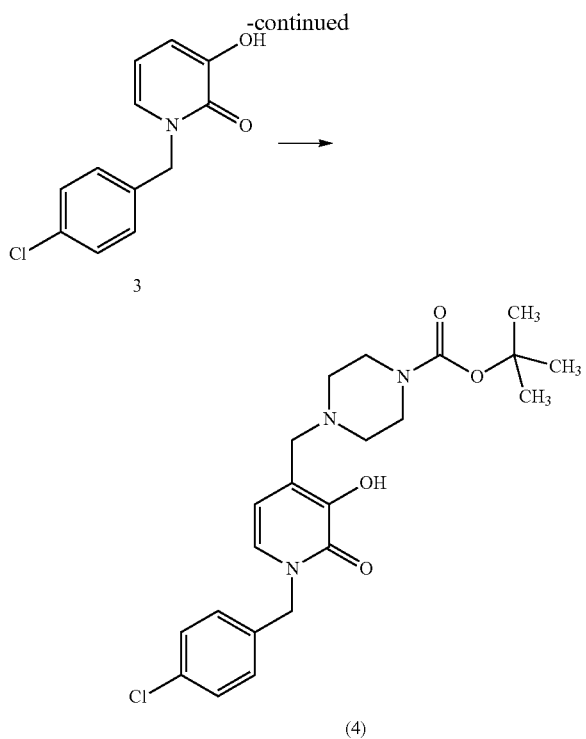

Reagents and conditions: (d)(i) H₂CHO, AcOH, t-Boc-piperazine, EtOH; 3 days.

Example 1 tert-Butyl-{[1-(4-chlorobenzyl)-3-hydroxy-2-oxo-1,2-dihydropyridin-4-yl]methyl}piperazine-1-carboxylate (4)

Preparation of 3-(tert-butyldimethylsilanyloxy)-1H-pyridin-2-one (1): 3-Hydroxypyridin-2(1H)-one (15 g, 135 mmol) and imidazole (23 g, 338 mmol) were suspended in dimethylformamide (200 mL) under inert atmosphere. A solution of tert-butyldimethylsilyl chloride (20.5 g, 136 mmol) in dimethylformamide (200 mL) is added dropwise at room temperature over 30 minutes. The reaction was then allowed to stir overnight. The resulting solution was then poured into water (300 mL) and the mixture extracted with tert-butyl methyl ether (3×500 mL). The combined organic layer was washed with water (300 mL), brine (300 mL) then dried over Na₂SO₄. The solvent is removed under reduced pressure and the crude product crystallized from heptanes to afford 16.3 g (53% yield) of the desired product. $^1$H NMR (250 MHz, CDCl₃) δ ppm 12.98 (1H, m); 6.91 (1H, dd, J=1.0 Hz, J=6.8 Hz); 6.81 (1H, dd, J=1.8 Hz, J=7.2 Hz); 6.02-6.007 (1H, m); 0.90 (9H, s), and 0.17 (6H, s).

Preparation of 3-(tert-butyldimethylsilanyloxy)-1-(3-chlorobenzyl)-1H-pyridin-2-one (2): At 0° C. under an inert atmosphere, a solution of 4-chlorobenzyl chloride (4.44 mmol) in THF (10 mL) was added dropwise to a solution of 3-(tert-butyldimethylsilanyloxy)-1H-pyridin-2-one, 1, (1 g, 4.44 mmol) and CsCO₃ (2.17 g, 6.66 mmol) in THF (10 mL). The reaction solution was allowed to warm to room temperature and stirring was continued overnight. The resulting solution was diluted with water (40 mL) and then extracted with EtOAc (3×30 mL). The combined organic layer was washed with brine (30 mL) then dried over Na₂SO₄. The solvent is removed under reduced pressure and the crude product purified over silica (EtOAc:heptane 4:1) to afford the desired product as a white solid.

Preparation of 1-(4-chlorobenzyl)-3-hydroxypyridin-2 (1H)-one (3): To a solution of 3-(tert-butyldimethylsilanyloxy)-1-(3-chlorobenzyl)-1H-pyridin-2-one, 2, (2.36 g, 10 mmol) in EtOAc (25 mL) as added 5 M HCl (25 mL) with vigorous stirring at room temperature. The reaction was monitored by TLC for the disappearance of starting material and was complete within 30 minutes. The organic layer was decanted and the aqueous phase extracted with dichloromethane (2×50 mL). The combined organic layers were dried over Na₂SO₄ and the solvent removed under reduced pressure. The crude product was recrystallized from dichloromethane. The yield was nearly quantitative. $^1$H NMR (360 MHz, DMSO-d₆) δ ppm 5.12 (2H, s); 6.13 (1H, t, J=7.04); 6.71 (1H, dd, J=7.04, 1.59); 7.23-7.28 (2H, m); 7.36-7.43 (2H, m); 9.10 (1H, br. s).

Preparation of tert-butyl-{[1-(4-chlorobenzyl)-3-hydroxy-2-oxo-1,2-dihydropyridin-4-yl]methyl}piperazine-1-carboxylate (4): tert-Butyl piperazine-1-carboxylate (97.6 mmol), formaldehyde (8 mL of a 37% soln., 97.6 mmol) and acetic acid (8 mL) were dissolved in ethanol (350 mL) and the solution stirred for 1 hour at room temperature. A solution of 1-(4-chlorobenzyl)-3-hydroxypyridin-2(1H)-one, 3, (48.8 mmol) in ethanol (350 mL) was added dropwise over 30 minutes. After 3 days of stirring, formaldehyde (3 mL) was added and the reaction heated to 50° C. after which the reaction solution was concentrated under reduced pressure to approximately 500 mL. The desired product is obtained by crystallization from ethanol. $^1$H NMR (250 MHz, CDCl₃) d ppm 1.46 (s, 9H); 2.38-2.57 (m, 4H); 3.40-3.49 (m, 4H); 3.51 (s, 2H); 5.13 (s, 2H); 6.13 (d, J=7.16 Hz), 1H); 6.79 (d, J=7.16 Hz, 1H); 7.20-7.41 (m, 4H); 8.33-8.85 (m, 1H). The disclosed biological data relate to A41.

Category II of the disclosed prolyl hydroxylase inhibitors relates to compounds having the formula:

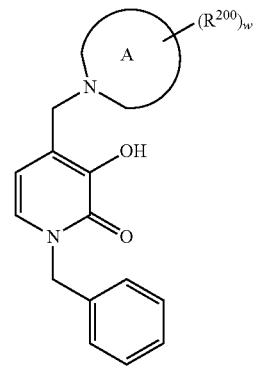

wherein A is a substituted or unsubstituted heterocyclic or heteroaryl ring having from 2 to 20 carbon atoms and from 1 to 7 heteroatoms, and $R^{200}$ represents from 0 to 40 substitutions form hydrogen. Table II provides representative examples of compounds according to this category.

TABLE II

| No. | A ring |
|---|---|
| B1 | pyrrolidin-1-yl |
| B2 | 3-hydroxypyrrolidin-1-yl |
| B3 | 2-(pyrdin-2-yl)pyrrolidin-1-yl |

TABLE II-continued

| No. | A ring |
|---|---|
| B4 | 2-methylcarboxypyrrolidin-1-yl |
| B5 | 2-(methoxymethyl)pyrrolidin-1-yl |
| B6 | thiazolidin-3-yl |
| B7 | 1H-imidazol-1-yl |
| B8 | piperidin-1-yl |
| B9 | 4-benzylpiperidin-1-yl |
| B10 | 1,4'-bipiperidinyl-1'-yl |
| B11 | piperazin-1-yl |
| B12 | 4-benzylpiperazin-1-yl |
| B13 | 4-(2-methoxyphenyl)piperazin-1-ylmethyl |
| B14 | 4-(6-chloropyridazin-3-yl)piperazin-1-yl |
| B15 | 1,4-dioxa-8-azaspiro[4,5]dec-8-yl |
| B16 | morpholin-4-yl |
| B17 | thiomorpholin-4-yl |
| B18 | azepan-1-yl |
| B19 | azocan-1-yl |
| B20 | 3,4-dihydroquinolin-1(2H)-yl |

The compounds according to Category II can be prepared according to the procedure outlined in Scheme I and disclosed in Example 1. The following are further examples of inhibitors according to Category II.

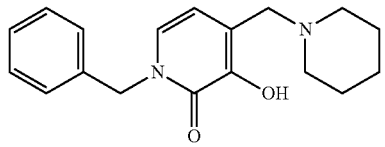

1-Benzyl-3-hydroxy-4-(piperidin-1-ylmethyl)pyridin-2 (1H)-one: $^1$H NMR (300 MHz, CD$_3$OD) δ 1.81 (m, 6H), 3.07 (m, 2H), 3.51 (m, 2H), 4.23 (s, 2H), 5.24 (s, 2H), 6.31 (d, J=6.9 Hz, 1H), 7.35 (m, 6H); $^{19}$F NMR (252 MHz, CD$_3$OD) δ 85.5; 13C NMR (75 MHz, DMSO) δ 21.3, 22.7, 51.8, 52.5, 53.1, 106.4, 117.4, 127.7, 128.0, 128.2, 128.9, 137.3, 147.4, 158.0; ES MS (M+1) 299.12; HRMS Calcd. For C$_{18}$H$_{22}$N$_2$O$_2$, 298.38. Found (M+1) 299.17.

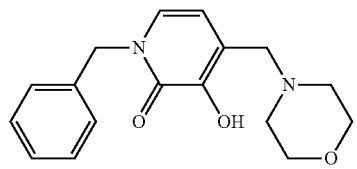

1-Benzyl-3-hydroxy-4-(morpholin-4-ylmethyl)pyridin-2 (1H)-one: $^1$H NMR (300 MHz, DMSO) δ 3.25 (m, 4H), 3.81 (m, 4H), 4.18 (s, 2H), 5.17 (s, 2H), 6.31 (d, J=6.9 Hz, 1H), 7.35 (m, 6H); $^{19}$FNMR (300 MHz, DMSO) δ 88.5; $^{13}$C NMR (300 MHz, DMSO) δ 51.6, 51.8, 53.4, 63.5, 107.9, 119.1, 127.8, 128.0, 128.2, 128.9, 137.3, 147.5, 158.3; ES MS (M+1) 301.12; HRMS Calcd. For C$_{17}$H$_{20}$N$_2$O$_3$, 300.35.

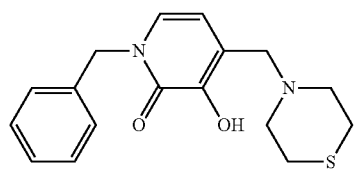

1-Benzyl-3-hydroxy-4-(thiomorpholin-4-ylmethyl)pyridin-2(1H)-one: $^1$HNMR (300 MHz, DMSO) δ 2.92 (m, 4H), 3.38 (m, 4H), 4.17 (s, 2H), 5.16 (s, 2H), 6.29 (d, J=7.5 Hz, 1H), 7.34 (m, 6H), 9.97 (s, 1H); $^{19}$F NMR (300 MHz, DMSO) δ 88.4; $^{13}$C NMR (75 MHz, DMSO) δ 24.3, 51.9, 53.4, 53.7, 107.9, 110.9, 127.8, 128.0, 128.2, 128.8, 137.2, 147.6, 157.6; ES MS (M+1) 317.14; HRMS Calcd. For C$_{17}$H$_{20}$N$_2$O$_2$S, 316.42. Found: (M+1) 317.13.

1-Benzyl-3-hydroxy-4-(thiazolidin-3-ylmethyl)pyridin-2 (1H)-one: $^1$HNMR (300 MHz, DMSO) δ 3.09 (t, J=6.3 Hz, 2H), 3.42 (t, J=6.3 Hz, 2H), 4.03 (s, 2H), 4.29 (s, 2H), 5.16 (s, 2H), 6.34 (d, J=7.2 Hz, 1H), 7.34 (m, 6H), 10.48 (broad s, 1H); $^{19}$FNMR (300 MHz, DMSO) δ 87.9; $^{13}$CNMR (75 MHz, DMSO) δ 28.3, 48.3, 50.1, 56.3, 57.0, 107.4, 122.1, 127.8, 128.2, 128.8, 137.4, 146.3, 157.6; ES MS (M+1) 303.08; Anal. Calcd for C$_{18}$H$_{19}$N$_2$O$_4$SF, C, 51.92; H, 4.60; N, 6.73; S, 7.70. Found: C, 51.67; H, 4.48; N, 6.69; S, 7.65.

1-Benzyl-3-hydroxy-4-(pyrrolidin-1-ylmethyl)pyridin-2 (1H)-one: $^1$H NMR (300 MHz, DMSO) δ 1.96 (s, 4H), 3.16 (s, 2H), 3.43 (s, 2H), 4.23 (s, 4H), 5.17 (s, 2H), 6.34 (d, J=7.2 Hz, 1H), 7.34 (m, 6H); $^{19}$F NMR (252 MHz, DMSO) δ 88.7; $^{13}$C NMR (75 MHz, DMSO) δ 22.8, 50.9, 51.8, 53.7, 107.3, 118.0, 128.0, 128.2, 128.9, 137.3, 146.7, 157.6; ES MS (M+1) 285.13; Anal. Calcd. For C$_{19}$H$_{21}$F$_3$N$_2$O$_4$, C, 57.28; H, 5.31; N, 7.03. Found: C, 57.10; H, 5.11, N, 7.02.

1-Benzyl-3-hydroxy-4-(4-benzylpiperidin-1-ylmethyl) pyridin-2(1H)-one: $^1$H NMR (DMSO) δ 1.43 (m, 2H), 1.72 (m, 4H), 2.96 (m, 2H), 3.41 (m, 3H), 4.09 (s, 2H), 5.16 (s, 2H), 6.34 (d, J=7.2 Hz, 1H), 7.35 (m, 11H); $^{19}$F NMR (252 MHz, DMSO) δ 88.8; $^{13}$C NMR (75 MHz, DMSO) δ; ES MS (M+1) 389.21; HRMS Calcd. For C$_{25}$H$_{28}$N$_2$O$_2$, 388.50. Found (M+1) 389.22.

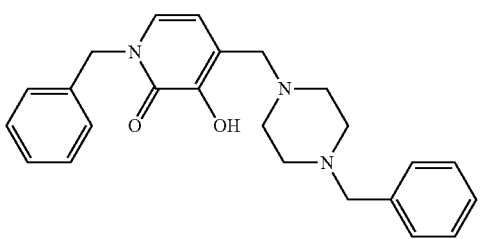

1-Benzyl-3-hydroxy-4-(4-benzylpiperazin-1-ylmethyl)pyridin-2(1H)-one: $^1$H NMR (300 MHz, DMSO) δ 3.11 (broad s, 4H), 3.81 (s, 2H), 4.18 (s, 2H), 5.15 (s, 2H), 6.24 (d, J=7.2 Hz, 1H), 7.34 (m, 6H), 7.46 (m, 5H); $^{19}$F NMR (252 MHz, DMSO) δ 88.2; 13C (75 MHz, DMSO) δ; ES MS (M+1) 390.21; HRMS Calcd. For $C_{24}H_{27}N_3O_2$, 389.49. Found (M+1) 390.21.

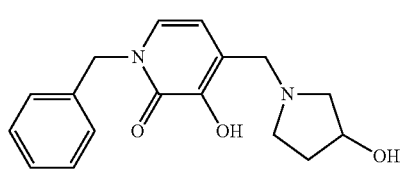

1-Benzyl-3-hydroxy-4-[(3-hydroxypyrrolidin-1-yl)methyl]pyridin-2(1H)-one: $^1$HNMR (300 MHz, DMSO) δ 1.90 (m, 1H), 3.18 (m, 2H), 3.47 (m, 3H), 4.24 (s, 2H), 4.43 (s, 1H), 5.17 (s, 2H), 6.34 (d, J=7.2 Hz, 1H), 7.34 (m, 6H); $^{19}$F NMR (252 MHz, DMSO) δ 89.0; $^{13}$C NMR (75 MHz, DMSO) δ 51.8, 52.6, 61.3, 68.6, 107.4, 117.9, 128.0, 128.2, 128.9, 137.3, 146.7, 157.6; ES MS (M+1) 301.13; HRMS Calcd. For $C_{17}H_{20}N_2O_3$, 300.35. Found: (M+1) 301.15.

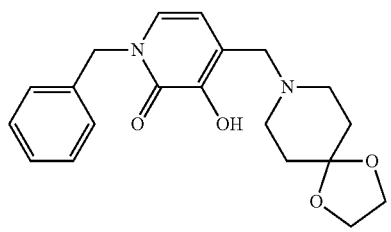

1-Benzyl-3-hydroxy-4-(1,4-dioxa-8-azaspiro[4,5]dec-8-ylmethyl)pyridin-2(1H)-one: $^1$H NMR (300 MHz, DMSO) δ 1.90 (m, 4H), 3.11 (m, 2H), 3.43 (m, 2H), 3.93 (s, 4H), 4.19 (s, 2H), 5.16 (s, 2H), 6.34 (d, J=7.2 Hz, 1H), 7.34 (m, 6H), 10.01 (broad s, 1H); $^{19}$F NMR (252 MHz, DMSO) δ 88.3; $^{13}$C NMR (75 MHz, DMSO) δ 31.7, 50.7, 51.9, 52.5, 64.5, 101.1, 108.0, 116.5, 127.8, 128.0, 128.3, 128.9, 137.3, 147.5 157.6; ES MS (M+1) 357.19; HRMS Calcd. For $C_{20}H_{24}N_4O_2$, 356.42. Found (M+1) 357.18.

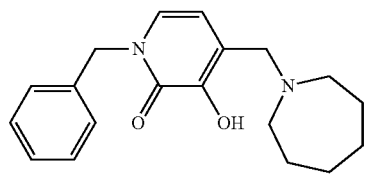

1-Benzyl-3-hydroxy-4-azepan-1-ylmethylpyridin-2(1H)-one: $^1$H NMR (300 MHz, DMSO) δ 1.61 (m, 4H), 1.80 (m, 4H), 3.20 (m, 4H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ 22.8, 26.4, 51.8, 53.4, 54.4, 107.6, 117.2, 127.9, 128.0, 18.2, 128.9, 137.3, 147.2, 157.6; ES MS (M+1) 313.18; HRMS Calcd. For $C_{19}H_{24}N_2O_4$, 312.41. Found (M+1) 313.19.

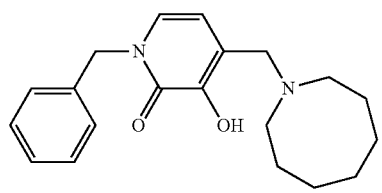

1-Benzyl-3-hydroxy-4-(azocan-1-ylmethyl)pyridin-2(1H)-one: $^1$H NMR (300 MHz, DMSO) δ 1.59 (m, 10H), 3.18 (m, 2H), 3.38 (m, 2H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ; ES MS (M+1) 327.2; HRMS Calcd. For $C_{20}H_{26}N_2O_2$, 326.43. Found (M+1) 327.20.

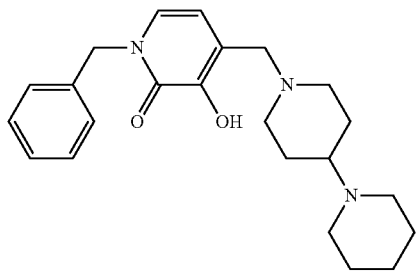

1-Benzyl-3-hydroxy-(1,4'-bipiperidinyl-1'-ylmethyl)pyridin-2(1H)-one: $^1$H NMR (300 MHz, DMSO) δ 1.43-1.98 (m, 10H), 2.21 (m, 2H), 3.01 (m, 4H), 3.43 (m, 3H), 4.12 (s, 2H), 5.16 (s, 2H), 6.34 (d, J=7.2 Hz, 1H), 7.34 (m, 6H), 9.85 (broad s, 1H); $^{19}$F NMR (252 MHz, DMSO) δ 88.7; $^{13}$C NMR (75 MHz, DMSO) δ 21.6, 22.9, 23.8, 49.6, 50.5, 51.8, 53.0, 59.5, 108.0, 127.8, 128.0, 128.2, 128.9, 137.3, 147.5, 157.6; ES MS (M+1) 382.4; HRMS Calcd. For $C_{23}H_{31}N_3O_2$, 383.51. Found (M+1) 382.25.

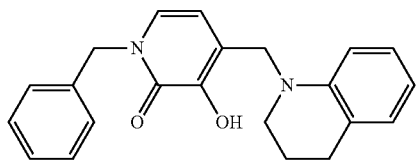

1-Benzyl-3-hydroxy-4-[(3,4-dihydroquinolin-1(2H)-yl)methyl]pyridin-2(1H)-one: $^1$H NMR (300 MHz, DMSO) δ 3.13 (t, J=6.3 Hz, 2H), 3.52 (m, 2H), 4.28 (s, 2H), 4.41 (s, 2H), 5.18 (s, 2H), 6.34 (d, J=7.2 Hz, 1H), 7.23-7.41 (m, 10H), 10.15 (broad s, 1H); $^{19}$F NMR (252 MHz, DMSO) δ 88.9; $^{13}$C NMR (75 MHz, DMSO) δ 25.4; 49.3, 51.8, 52.7, 52.9, 107.6, 11.6, 116.8, 126.9, 127.0, 127.9, 128.0, 128.1, 128.2, 128.8, 128.9, 131.7, 137.3, 147.3, 157.6; ES MS (M+1) 347.40; HRMS Calcd. For $C_{22}H_{22}N_2O_2$, 346.42. Found (M+1) 347.17.

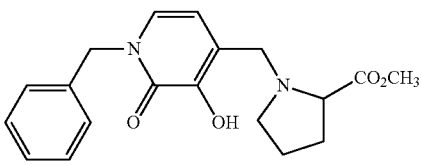

Methyl 1-[(1-benzyl-3-hydroxy-2-oxo-1,2-dihydropyridin-4-yl)methyl]pyrrolidine-2-carboxylate: $^1$H NMR (300 MHz, DMSO) δ 2.01 (m, 3H), 2.45 (m, 1H), 3.26 (m, 1H), 3.53 (m, 1H), 3.69 (s, 3H), 4.30 (m, 3H), 5.17 (s, 2H), 6.27 (d, 6.9 Hz, 1H), 7.35 (m, 6H), $^{19}$F NMR (252 MHz, DMSO) δ 88.3; 13C NMR (75 MHz, DMSO) δ; ES MS (M+1) 343.20; HRMS Calcd. For $C_{19}H_{22}N_2O_4$, 342.39. Found (M+1)

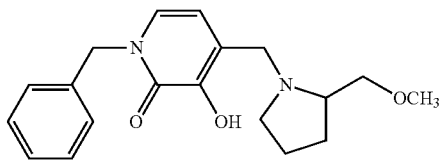

1-Benzyl-3-hydroxy-4-{[2-(methoxymethyl)pyrrolidin-1-yl]methyl}pyridin-2(1H)-one: $^1$H NMR (300 MHz, DMSO) δ 1.71 (m, 1H), 1.84 (m, 1H), 1.99 (m, 1H), 2.15 (m, 1H), 3.19 (m, 1H), 3.30 (s, 3H), 3.41 (m, 1H), 3.62 (m, 2H), 3.77 (m, 1H), 4.15 (m, 1H), 4.39 (m, 1H), 5.17 (s, 2H), 6.34 (d, J=7.2 Hz, 1H), 7.34 (m, 6H); 9.60 (broad s, 1H); $^{19}$F NMR (252 MHz, DMSO) δ 88.3; $^{13}$C NMR (75 MHz, DMSO) δ; ES MS (M+1) 329.2; HRMS Calcd. For $C_{19}H_{24}N_2O_3$, 328.41. Found (M+1)

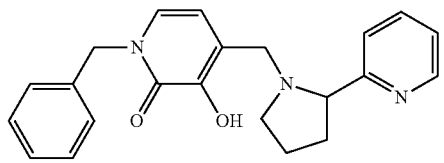

1-Benzyl-3-hydroxy-4-{[2-(pyrdin-2-yl)pyrrolidin-1-yl]methyl}pyridin-2(1H)-one: $^1$H NMR (300 MHz, DMSO) δ 2.12 (m, 4H), 3.39 (m, 1H), 3.63 (m, 1H), 4.07 (m, 2H), 4.60 (m, 1H), 5.10 (m, 2H), 6.15 (d, J=6.9 Hz, 1H), 7.33 (m, 6H), 7.44 (m, 1H), 8.05 (d, J=8.1 Hz, 1H), 8.59 (d, J=4.8 Hz, 1H), 8.74 (s, 1H); $^{19}$F NMR (252 MHz, DMSO) δ 88.0; ES MS (M+1) 362.22; HRMS Calcd. For $C_{22}H_{23}N_3O_2$, 361.44. Found (M+1).

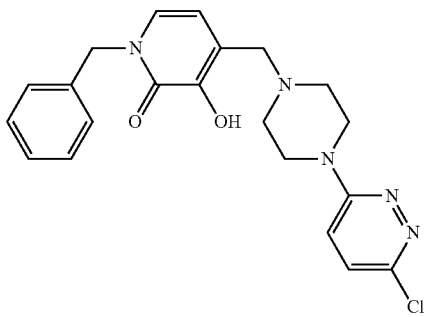

1-Benzyl-3-hydroxy-4-[4-(6-chloropyridazin-3-yl)piperazin-1-ylmethyl]pyridin-2(1H)-one: $^1$H NMR (300 MHz, DMSO) δ 3.18 (m, 2H), 3.48 (m, 4H), 4.19 (s, 2H), 4.46 (m, 2H), 5.16 (s, 2H), 6.62 (d, J=7.2 Hz, 1H), 7.35 (m, 6H), 7.48 (m, 1H), 7.68 (m, 1H), 11.5 (broad s, 1H); $^{13}$C NMR (75 MHz, DMSO) δ 42.1, 50.3, 51.9, 52.5, 108.2, 116.2; 118.0, 128.0, 128.2, 128.9, 129.8, 137.3, 147.4, 157.6, 158.8; ES MS (M+1) 476.09. HRMS Calcd. For $C_{21}H_{22}ClN_5N_3O_2$, 411.88. Found (M+1) 412.76.

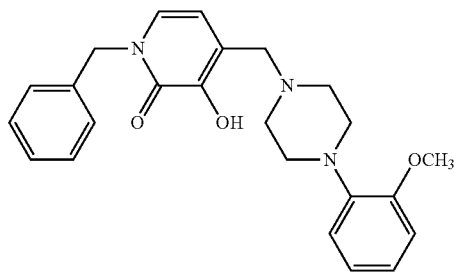

1-Benzyl-3-hydroxy-4-[4-(2-methoxyphenyl)piperazin-1-ylmethyl]pyridin-2(1H)-one: $^1$H NMR (300 MHz, DMSO) δ 2.95 (m, 2H), 3.30 (m, 2H), 3.48 (m, 4H), 3.80 (s, 3H), 4.25 (s, 2H), 5.18 (s, 2H), 6.34 (d, J=7.2 Hz, 1H), 6.93 (m, 2H), 7.01 (m, 2H), 7.34 (m, 6H); $^{19}$F NMR (252 MHz, DMSO) δ 88.5; 13C NMR (75 MHz, DMSO) δ 47.2, 51.8, 53.0, 55.3, 108.1, 112.2, 114.8, 116.2, 118.6, 121.2, 123.8, 127.8, 128.0, 128.9, 137.3, 139.6, 147.5, 152.2, 157.6; ES MS (M+1) 405.82; HRMS Calcd. For $C_{24}H_{27}N_3O_3$, 405.49. Found (M+1) 406.21.

Category III of the disclosed prolyl hydroxylase inhibitors relates to compounds having the formula:

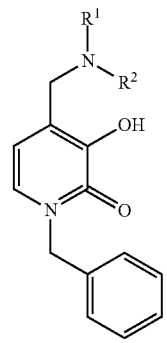

$R^1$ and $R^2$ are each independently hydrogen or substituted or unsubstituted $C_1$-$C_{10}$ linear or branched alkyl, wherein the alkyl unit can be substituted by one or more units independently chosen from:
  i) $C_1$-$C_8$ linear, $C_3$-$C_8$ branched, or $C_3$-$C_8$ cyclic alkoxy;
  ii) hydroxy;
  iii) halogen;
  iv) cyano;
  v) amino, $C_1$-$C_8$ mono-alkylamino, $C_1$-$C_8$ di-alkylamino;
  vi) —$SR^{40}$; $R^{40}$ is hydrogen or $C_1$-$C_4$ linear or $C_3$-$C_4$ branched alkyl;
  vii) substituted or unsubstituted $C_6$ of $C_{10}$ aryl;
  viii) substituted or unsubstituted $C_1$-$C_9$ heterocyclic; or
  ix) substituted or unsubstituted $C_1$-$C_9$ heteroaryl.

Table III herein below provides non-limiting examples of compounds encompassed by this category.

TABLE III

| No. | R¹ | R² |
| --- | --- | --- |
| C1 | benzyl | hydrogen |
| C2 | 4-methoxybenzyl | hydrogen |
| C3 | 4-fluorobenzyl | hydrogen |
| C4 | 4-chlorobenzyl | hydrogen |
| C5 | 4-methylbenzyl | hydrogen |
| C6 | 2-(pyridin-2-yl)ethyl | hydrogen |
| C7 | [1,3]dioxolan-2-ylmethyl | hydrogen |
| C8 | tetrahydrofuran-2-ylmethyl | hydrogen |
| C9 | 2-methoxyethyl | hydrogen |
| C10 | 1-hydroxy-2-methylpropan-2-yl | hydrogen |
| C11 | pyridin-4-ylmethyl | hydrogen |
| C12 | furan-2-ylmethyl | hydrogen |
| C13 | 2-(methylthio)ethyl | hydrogen |
| C14 | 1-phenylethyl | hydrogen |
| C15 | 3-imidazol-1-ylpropyl | hydrogen |
| C16 | cycloheptyl | hydrogen |
| C17 | 4-methylcyclohexyl | hydrogen |
| C18 | 1-benzylpiperidin-4-yl | hydrogen |
| C19 | azepan-2-on-3-yl | hydrogen |
| C20 | 1-benzylpyrrolidin-3-yl | hydrogen |
| C21 | benzyl | methyl |
| C22 | 4-methoxybenzyl | methyl |
| C23 | 4-fluorobenzyl | methyl |
| C24 | 4-chlorobenzyl | methyl |
| C25 | 4-methylbenzyl | methyl |
| C26 | 2-(pyridin-2-yl)ethyl | methyl |
| C27 | [1,3]dioxolan-2-ylmethyl | methyl |
| C28 | tetrahydrofuran-2-ylmethyl | methyl |
| C29 | 2-methoxyethyl | methyl |
| C30 | 1-hydroxy-2-methylpropan-2-yl | methyl |
| C31 | pyridin-4-ylmethyl | methyl |
| C32 | furan-2-ylmethyl | methyl |
| C33 | 2-(methylthio)ethyl | methyl |
| C34 | 1-phenylethyl | methyl |
| C35 | 3-(1H-imidazol-1-yl)propyl | methyl |
| C36 | cycloheptyl | methyl |
| C37 | 4-methylcyclohexyl | methyl |
| C38 | 1-benzylpiperidin-4-yl | methyl |
| C39 | azepan-2-on-3-yl | methyl |
| C40 | 1-benzylpyrrolidin-3-yl | methyl |

The disclosed compounds of this category can be prepared by the procedure outlined herein below in Scheme II and described in Example 2.

Scheme II

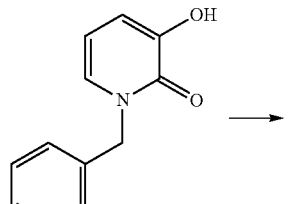

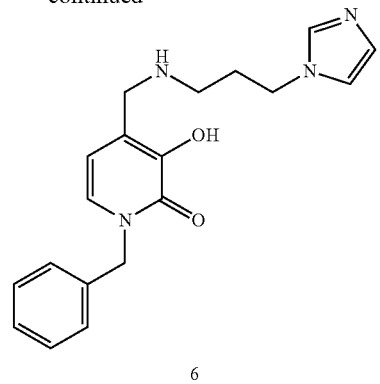

Reagents and conditions: (a)(i) HCHO, EtOH; 0.5 hr (ii) 3-(1-H-imidazol-1-yl)propan-1-amine; 2 hr.

Example 2

1-Benzyl-3-hydroxy-4-{[3-(1-H-imidazol-1-yl)propylamino]methyl}-pyridin-2(1H)-one (6)

N-Benzyl-3-hydroxypyridin-2(1H)-one (5) can be prepared according to Example 1 by substituting benzyl bromide or benzyl chloride into step (b) for (4-chloro)benzyl chloride.

1-Benzyl-3-hydroxy-4-{[3-(1-H-imidazol-1-yl)propylamino]methyl}pyridin-2(1H)-one (6): N-Benzyl-3-hydroxypyridin-2(1H)-one (5) (250 mg, 1.23 mmol) and formaldehyde (200 mg, 273 eq.) are combined in aqueous ethanol (10 mL) and stirred for 30 minutes. 3-(1-H-Imidazol-1-yl)propan-1-amine (340 mg, 2.7 mmol) is then added and the reaction stirred for 12 hours. The solvent is removed by evaporation and the residue dissolved in methanol (2 mL) and purified via prep HPLC eluting with water/acetonitrile to afford the desired product as the trifluoroacetate salt. $^1$H NMR (300 MHz, DMSO) δ 2.19 (m, 2H), 2.97 (m, 2H), 4.02 (s, 2H), 4.30 (t, J=6.6 Hz, 2H); 5.17 (s, 2H), 6.30 (d, J=6.9 Hz, 1H), 7.36 (m, 6H), 7.26 (s, 1H), 7.76 (s, 1H), 9.03 (s, 1H), 9.11 (s, 1H); $^{19}$F NMR (252 MHz, DMSO) δ 88.5; $^{13}$C NMR (75 MHz, DMSO) δ 26.5, 44.0, 46.0, 51.8, 106.8, 118.7, 120.5, 122.2, 127.9, 128.2, 128.9, 135.8, 137.4, 146.0, 158.2; ES MS (M+1) 339.05; HRMS Calcd. For $C_{19}H_{22}N_4O_2$, 338.44. Found (M+1) 339.18.

The following are further non-limiting examples of this aspect of the disclosed HIF-1α prolyl hydroxylase inhibitors.

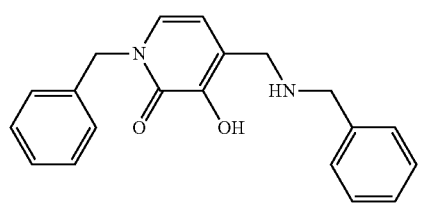

1-Benzyl-3-hydroxy-4-(benzylaminomethyl)pyridin-2(1H)-one: $^1$HNMR (300 MHz, DMSO) δ 4.01 (s, 2H), 4.20 (s, 2H), 5.16 (s, 2H), 6.34 (d, J=7.2 Hz, 1H), 7.36 (m, 11H), 9.16 (broad s, 1H); $^{19}$FNMR (252 MHz, DMSO) δ 88.6; $^{13}$C NMR (75 MHz, DMSO) δ; ES MS (M+1) 321.16; Anal. Calcd. For $C_{22}H_{21}F_3N_2O_4$, C, 60.83; H, 4.87; N, 6.45. Found: C, 60.75; H, 4.56; N, 6.34.

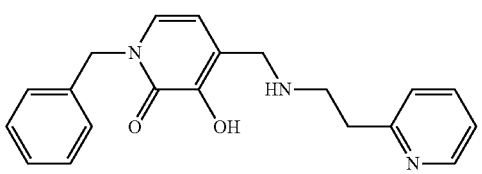

1-Benzyl-3-hydroxy-4-{[(2-(pyridin-2-yl)ethylamino]methyl}pyridin-2(1H)-one: $^1$H NMR (300 MHz, DMSO) δ 3.26 (m, 2H), 3.37 (m, 2H), 4.08 (s, 2H), 5.17 (s, 2H); 6.34 (d, J=7.2 Hz, 1H), 7.38 (m, 6H), 7.86 (d, J=5.7 Hz, 2H), 8.84 (m, 2H), 9.32 (broad s, 1H); $^{19}$FNMR (252 MHz, DMSO) δ 88.6; $^{13}$C NMR (75 MHz, DMSO) δ 31.5, 44.1, 46.3, 51.8, 106.9, 114.8, 127.1, 128.1, 128.8, 137.4, 143.8, 146.1, 155.3, 157.5, 158.4; ES MS (M+1) 336.18; HRMS Calcd For $C_{20}H_{21}N_3O_2$, 335.40. Found: 336.16.

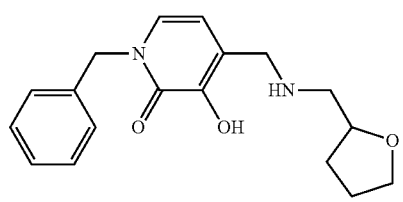

1-Benzyl-3-hydroxy-4-{[(tetrahydrofuran-2-ylmethyl)amino]methyl}pyridin-2(1H)-one: $^1$H NMR (300 MHz, DMSO) δ 1.56 (m, 1H), 1.86 (m, 2H), 1.99 (m, 1H), 2.92 (m, 1H), 3.05 (m, 1H), 3.80 (m, 2H), 4.09 (m, 3H), 5.16 (s, 2H), 6.34 (d, J=7.2 Hz, 1H), 7.34 (m, 6H); 8.91 (broad s, 1H); $^{19}$F NMR (252 MHz, DMSO) δ 88.5; $^{13}$C NMR (75 MHz, DMSO) δ; ES MS (M+1) 315.16; HRMS. Calcd. For $C_{18}H_{22}N_2O_3$, 314.38. Found (M+1) 315.16.

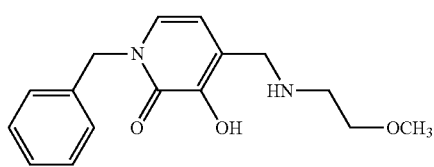

1-Benzyl-3-hydroxy-4-[(2-methoxyethylamino)methyl]pyridin-2(1H)-one: $^1$H NMR (300 MHz, DMSO) δ 3.13 (broad s, 2H), 3.30 (s, 3H), 3.59 (t, J=5.4 Hz, 2H), 4.02 (s, 2H), 5.16 (s, 2H), 6.34 (d, J=7.2 Hz, 1H), 7.34 (m, 6H), 8.91 (broad s, 1H); $^{19}$F NMR (252 MHz, DMSO) δ 88.4; $^{13}$C NMR (252 MHz, DMSO) δ; ES MS (M+1) 289.13; HRMS Calcd. For $C_{16}H_{20}N_2O_3$, 288.34. Found (M+1) 289.15.

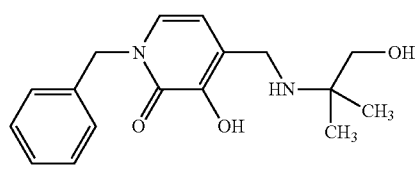

1-Benzyl-3-hydroxy-4-[(1-hydroxy-2-methylpropan-2-ylamino)methyl]pyridin-2(1H)-one: $^1$H NMR (300 MHz, DMSO) δ 1.27 (s, 6H), 3.49 (s, 2H), 3.95 (s, 2H), 5.17 (s, 2H), 6.34 (d, J=7.2 Hz, 1H), 7.34 (m, 6H), 8.47 (broad s, 2H), 9.94 (broad s, 1H); $^{19}$F NMR (252 MHz, DMSO) δ 88.7; 13C NMR (75 MHz, DMSO) δ; ES MS (M+1) 303.19; HRMS Calcd. For $C_{17}H_{22}N_2O_3$, 302.37. Found (M+1) 303.17.

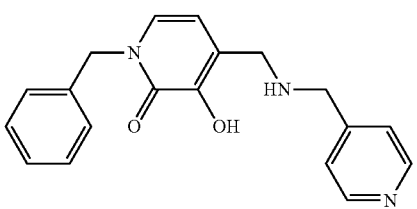

1-Benzyl-3-hydroxy-4-[(pyridin-4-ylmethylamino)methyl]pyridin-2(1H)-one: $^1$H NMR (300 MHz, DMSO) δ 4.07 (s, 2H), 4.32 (s, 2H), 5.16 (s, 2H), 6.34 (d, J=7.2 Hz, 1H), 7.34 (m, 6H); 7.62 (d, J=5.7 Hz, 2H), 8.71 (d, J=4.5 Hz, 2H); $^{19}$F NMR (252 MHz, DMSO) δ 88.0; $^{13}$C NMR (75 MHz, DMSO) δ; ES MS (M+1) 322.17; HRMS Calcd. For $C_{19}H_{19}N_3O_2$, 321.37. Found (M+1) 322.15.

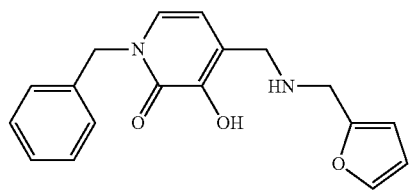

1-Benzyl-3-hydroxy 4-{[(furan-2-ylmethyl)amino]methyl}pyridin-2(1H)-one: $^1$H NMR (300 MHz, DMSO) δ 4.00 (s, 2H), 4.28 (s, 2H), 5.16 (s, 2H), 6.27 (d, J=6.9 Hz, 1H), 6.54 (m, 1H), 6.65 (m, 1H), 7.34 (m, 6H), 7.80 (m, 1H), 9.27 (broad s, 1H); $^{19}$F NMR (252 MHz, DMSO) δ 88.3; $^{13}$C NMR (75 MHz, DMSO) δ; ES MS (M+1) 323.15; HRMS Calcd. For $C_{18}H_{18}N_2O_3$, 310.35. Found (M+1)

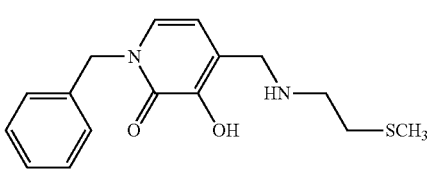

1-Benzyl-3-hydroxy-4-{[2-(methylthio)ethylamino]methyl}pyridin-2(1H)-one: $^1$H NMR (300 MHz, DMSO) δ 2.10 (s, 3H), 2.74 (t, J=6.9 Hz, 2H), 3.16 (t, J=8.1 Hz, 2H), 4.05 (s, 2H), 5.17 (s, 2H), 6.34 (d, J=7.2 Hz, 1H), 7.34 (m, 6H), $^{19}$F NMR (252 MHz, DMSO) δ 89.0; ES MS (M+1) 305.14, HRMS Calcd. For $C_{16}H_{20}N_2O_2S$, 304.41. Found (M+1)

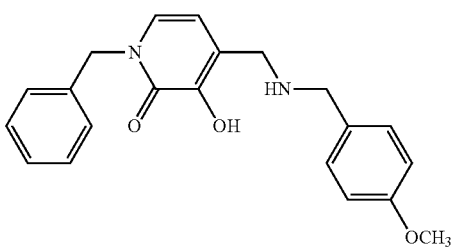

1-Benzyl-3-hydroxy-4-[(4-methoxybenzylamino)methyl]pyridin-2(1H)-one: $^1$H NMR (300 MHz, DMSO) δ 3.70 (s, 3H), 3.98 (s, 2H), 4.13 (s, 2H), 5.16 (s, 2H), 6.28 (d, J=7.5 Hz, 1H), 7.00 (d, J=9.0 Hz, 4H), 7.34 (m, 6H); 9.07 (broad s, 1H); $^{19}$F NMR (252 MHz, DMSO) δ 89.0; ES MS (M+1) 351.10; HRMS Calcd. For $C_{21}H_{22}N_2O_3$, 350.41. Found (M+1) 351.17.

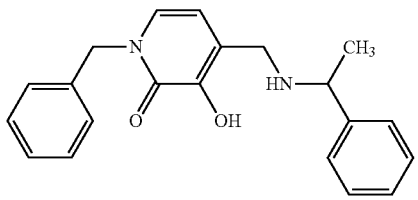

1-Benzyl-3-hydroxy-4-[(1-phenylethylamino)methyl]pyridin-2(1H)-one: $^1$H NMR (300 MHz, DMSO) δ 1.59 (d, J=7.2 Hz, 3H), 3.71-3.93 (m, 2H), 4.45 (m, 1H), 5.15 (s, 2H), 6.28 (d, J=7.5 Hz, 1H), 7.34 (m, 11H); $^{19}$F NMR (252 MHz, DMSO) δ 88.9; $^{13}$C NMR (75 MHz, DMSO) δ 19.6, 42.5, 51.7, 58.0, 106.8, 119.3, 128.0, 128.1, 128.2, 128.9, 129.3, 129.4, 137.3, 145.9, 158.3; ES MS (M+1) 335.13; HRMS Calcd. For $C_{21}H_{22}N_2O_2$, 334.41. Found (M+1) 335.17.

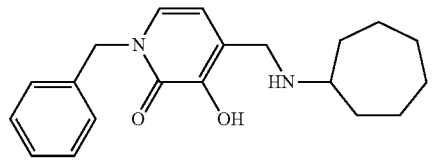

1-Benzyl-3-hydroxy-4-(cycloheptylaminomethyl)pyridin-2(1H)-one: $^1$H NMR (300 MHz, DMSO) δ 1.55 (m, 10H), 2.03 (m, 2H), 3.18 (s, 1H), 3.99 (m, 2H), 5.17 (s, 2H), 6.32 (d, J=6.9 Hz, 1H), 7.35 (m, 6H), 8.65 (broad s, 2H), 9.98 (broad s, 1H); $^{19}$F NMR (252 MHz, DMSO) δ 88.6; $^{13}$C NMR (75 MHz, DMSO) δ 23.0, 27.2, 30.4, 41.6, 51.7, 58.9, 107.0, 111.7, 127.9, 128.0, 128.2, 128.8, 137.4, 146.0, 157.5; ES MS (M+1) 327.13; HRMS Calcd. For $C_{20}H_{26}N_2O_2$, 326.43. Found (M+1) 327.20.

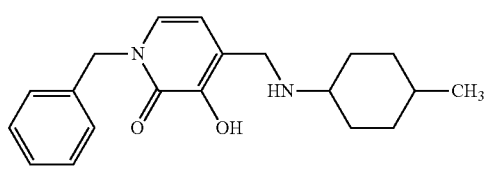

1-Benzyl-3-hydroxy-4-[(4-methylcyclohexylamino)methyl]pyridin-2(1H)-one: $^1$H NMR (300 MHz, DMSO) δ 0.93 (d, J=6.9 Hz, 3H), 1.38 (m, 4H), 1.74 (m, 4H), 2.05 (m, 1H), 3.10 (m, 1H), 4.01 (s, 2H), 5.17 (s, 2H), 6.31 (m, 1H), 7.34 (m, 6H), 8.05 (broad s, 2H), 9.98 (broad s, 1H); $^{19}$F NMR (252 MHz, DMSO) δ 88.9; ES MS (M+1) 327.14; HRMS Calcd. For $C_{20}H_{26}N_2O_2$, 326.43; Found (M+1) 372.20.

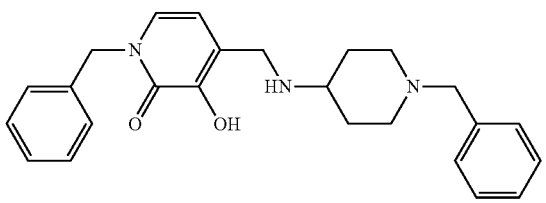

1-Benzyl-3-hydroxy-4-[(1-benzylpiperidin-4-ylamino)methyl]pyridin-2(1H)-one: $^1$H NMR (300 MHz, DMSO) δ 1.77 (m, 2H), 2.31 (m, 2H), 2.98 (m, 2H), 3.30 (m, 3H), 3.46 (m, 2H), 4.03 (s, 2H), 0.29 (s, 2H), 5.16 (s, 2H), 6.30 (d, J=7.5 Hz, 1H), 7.34 (m, 6H), 7.49 (s, 5H), 9.12 (broad s, 1H), 10.05 (broad s, 1H); $^{19}$F NMR (252 MHz, DMSO) δ 88.8; $^{13}$C NMR (75 MHz, DMSO) δ 27.1, 43.4, 51.8, 52.1, 54.2, 54.7, 57.6, 106.9, 118.5, 128.0, 128.1, 128.8, 129.3, 129.8, 130.7, 131.3, 137.3, 146.2, 157.4; ES MS (M+1) 404.56; HRMS Calcd. For $C_{25}H_{28}N_3O_2$, 403.52. Found (M+1) 404.23.

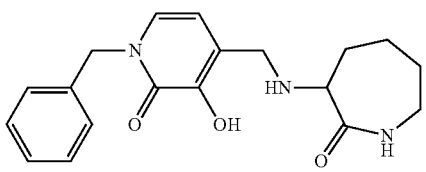

3-[(1-Benzyl-3-hydroxy-2-oxo-1,2-dihydropyridin-4-yl)methylamino]azepan-2-one: $^1$H NMR (300 MHz, DMSO) δ 1.25 (m, 1H), 1.59 (m, 2H), 1.74 (m, 1H), 1.92 (m, 1H), 2.10 (m, 1H), 3.18 (m, 3H), 4.03 (s, 2H), 4.2 (m, 1H), 5.17 (s, 2H), 6.33 (d, J=7.5 Hz, 1H), 7.34 (m, 6H), 8.31 (t, J=5.4 Hz, 1H), 9.07 (broad s, 2H), 9.90 (broad s, 1H); $^{19}$F NMR (252 MHz, DMSO) δ 88.4; $^{13}$C NMR (75 MHz, DMSO) δ 27.0, 27.2, 28.4, 43.4, 51.7, 59.3, 107.1, 118.9, 127.8, 127.9, 128.1, 128.9, 137.4, 146.0, 157.5, 166.3; ES MS (M+1) 342.01; HRMS Calcd. For $C_{19}H_{23}N_3O_3$, 341.40. Found (M+1) 342.18.

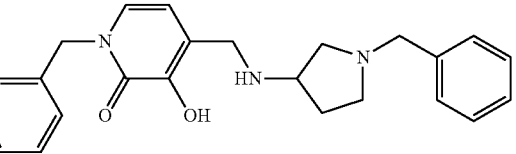

1-Benzyl-3-hydroxy-4-[(1-benzylpyrrolidin-3-ylamino)methyl]pyridin-2(1H)-one: $^1$H NMR (300 MHz, DMSO) δ 2.22 (m, 2H), 2.42 (m, 1H), 3.39 (m, 3H), 3.68 (m, 1H), 4.06 (s, 2H), 4.39 (s, 2H), 5.17 (s, 2H), 6.33 (d, J=7.5 Hz, 1H), 7.30-7.52 (m, 11H); $^{19}$F NMR (252 MHz, DMSO) δ 88.5; $^{13}$C NMR (75 MHz, DMSO) δ 27.1, 43.4, 51.8, 52.1, 54.2, 54.7, 57.5, 106.9, 118.5, 128.0, 128.8, 129.3, 129.8, 130.7, 131.3, 137.3, 146.2, 157.5; ES MS (M+1) 390.14; HRMS Calcd. For $C_{24}H_{27}N_3O_2$, 389.49. Found (M+1) 390.21.

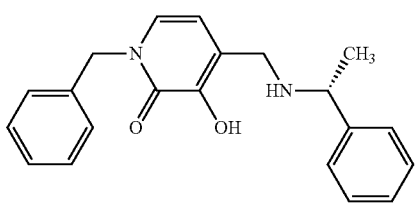

(R)-1-Benzyl-3-hydroxy-4-[(1-phenylethylamino)methyl]pyridin-2(1H)-one: $^1$H NMR (300 MHz, DMSO) δ 1.58 (d, J=6.9 Hz, 3H), 3.74 (m, 2H), 4.44 (m, 1H), 5.14 (s, 2H), 6.23 (d, J=7.2 Hz, 1H), 7.35 (m, 6H); $^{19}$F NMR (252 MHz, DMSO) δ 89.4; $^{13}$C NMR (75 MHz, DMSO) δ 19.6, 42.6, 51.7, 58.0, 106.9, 18.7, 128.0, 128.1, 128.8, 129.3, 129.4, 137.2, 137.4, 145.9, 157.5; ES MS (M+1) 335.13; Anal. Calcd. For $C_{21}H_{22}N_2O_2$, 334.41. Found (M+1) 335.31.

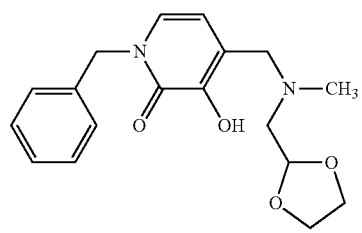

1-Benzyl-3-hydroxy-4-[([1,3]dioxolan-2-ylmethylmethylamino)methyl]pyridin-2(1H)-one: $^1$H NMR (300 MHz, DMSO) δ 2.81 (s, 3H), 3.35 (d, J=3.9 Hz, 2H), 3.89 (m, 2H), 4.01 (m, 2H), 4.21 (m, 2H), 5.17 (s, 2H); 5.27 (t, J=3.9 Hz, 1H), 6.34 (d, J=7.2 Hz, 1H), 7.35 (m, 6H); $^{19}$F NMR (252 MHz, DMSO) δ 88.5; $^{13}$C NMR (75 MHz, DMSO) δ; ES MS (M+1) 331.18; HRMS Calcd. For $C_{18}H_{22}N_2O_4$, 330.38. Found (M+1) 331.16.

Category IV of the disclosed prolyl hydroxylase inhibitors relates to compounds having the formula:

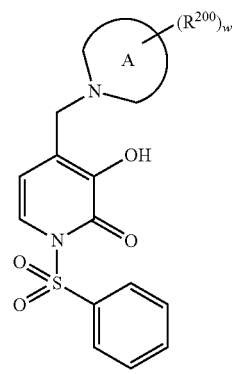

wherein A represents a ring optionally substituted by one or more R$^{200}$ units. Table IV provides non-limiting examples of this category.

TABLE IV

| No. | A ring |
|-----|--------|
| D1  | pyrrolidin-1-yl |
| D2  | 3-hydroxypyrrolidin-1-yl |
| D3  | 2-(pyrdin-2-yl)pyrrolidin-1-yl |
| D4  | 2-methylcarboxypyrrolidin-1-yl |
| D5  | 2-(methoxymethyl)pyrrolidin-1-yl |
| D6  | thiazolidin-3-yl |
| D7  | 1H-imidazol-1-yl |
| D8  | piperidin-1-yl |
| D9  | 4-benzylpiperidin-1-yl |
| D10 | 1,4'-bipiperidinyl-1'-yl |
| D11 | piperazin-1-yl |
| D12 | 4-benzylpiperazin-1-yl |
| D13 | 4-(2-methoxyphenyl)piperazin-1-ylmethyl |
| D14 | 4-(6-chloropyridazin-3-yl)piperazin-1-yl |
| D15 | 1,4-dioxa-8-azaspiro[4,5]dec-8-yl |
| D16 | morpholin-4-yl |
| D17 | thiomorpholin-4-yl |
| D18 | azepan-1-yl |
| D19 | azocan-1-yl |
| D20 | 3,4-dihydroquinolin-1(2H)-yl |

The disclosed compounds of this category can be prepared by the procedure outlined herein below in Scheme III and described in Example 3.

Scheme III

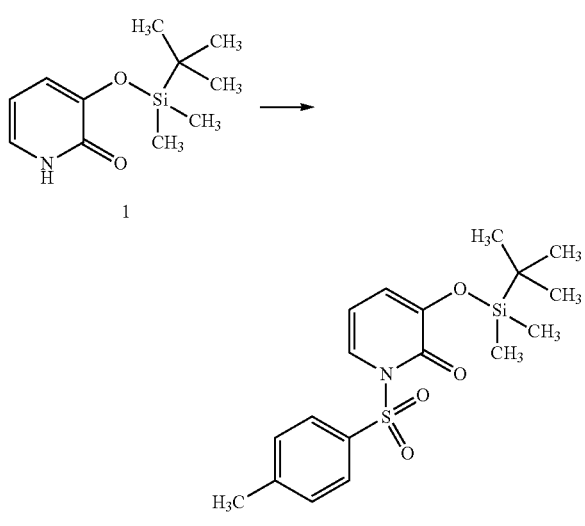

Reagents and conditions:
(a) (i) n-BuLi, TsCl, THF; -78° C. to rt, 1 hr;
   (ii) HCl, MeOH; rt, 1 hr.

-continued

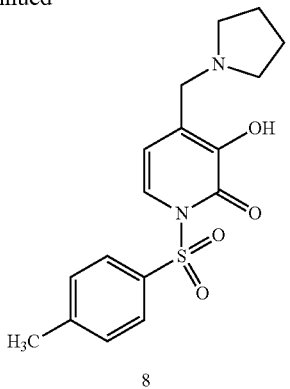

Reagents and conditions:
(b) pyrrolidine, HCHO, H₂O, H₂O/EtOH; rt, 12 hr.

Example 3

1-(4'-Methylbenzenesulfonyl)-3-hydroxy-4-(pyrrolidin-1-ylmethyl)pyridin-2(1H)-one (8)

1-(4'-Methylbenzenesulfonyl)-3-hydroxypyridin-2(1H)-one (7): To stirred solution of 3-[(tert-butyldimethylsilyl)oxy]pyridin-2(1H)-one (1) (4.66 g, 20.7 mmol) in dry THF (150 mL), maintained at −78° C. under a dry nitrogen atmosphere is added n-butyl lithium (1.6 M solution in hexane, 21.0 mmol). After 20 minutes, 4-methylbenzenesulfonyl chloride (3.95 g, 20.7 mmol) is added as a THF solution. The solution is allowed to warm to room temperature over one hour, the water (10 mL) is added and the contents of the reaction vessel is extracted with EtOAc (3×), washed with brine (1×), dried over Na$_2$SO$_4$ and concentrated. The combined organic layers are dried over Na$_2$SO$_4$ and concentrated. The residue is taken up in ethanol (10 mL) and treated with conc. HCl (2 mL). The mixture is allowed to stir for 1 hour and the solvent is removed under reduced pressure to afford the desired compound as a white solid. $^1$H NMR (300 MHz, DMSO) δ 2.43 (s, 3H), 6.14 (t, J=6.9 Hz, 1H), 6.76 (dd, J=7.65 Hz, 1.5 Hz, 1H), 7.18 (dd, J=6.6 Hz, 1.8 Hz, 1H), 7.32 (d, J=7.3 Hz, 2H), 7.98 (d, J=7.9 Hz, 2H).

1-(4'-Methylbenzenesulfonyl)-3-hydroxy-4-(pyrrolidin-1-ylmethyl)pyridin-2(1H)-one (8): 1-(4'-Methylbenzenesulfonyl)-3-hydroxypyridin-2(1H)-one (7) (250 mg, 0.94 mmol) and formaldehyde (200 mg, 2.07 mmol) are combined in aqueous ethanol (10 mL) and stirred for 30 minutes. Pyrrolidine (149 mg, 2.07 mmol) is then added and the reaction stirred for 12 hours. The solvent is removed by evaporation and the residue dissolved in methanol (5 mL) and purified via prep HPLC eluting with water/acetonitrile to afford the desired product. $^1$H NMR (300 MHz, DMSO) δ 1.87 (m, 2H), 1.99 (m, 2H), 2.44 (s, 3H), 3.09 (m, 2H), 3.40 (m, 2H), 4.19 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz, 1H), 9.93 (broad s, 1H); $^{19}$F NMR (252 MHz, DMSO) δ 88.4; 13C NMR (75 MHz, DMSO) δ 21.5, 22.7, 50.5, 53.7, 108.7, 118.6, 119.4, 128.4, 129.7, 130.1, 133.1, 146.8, 147.7, 156.2; ES MS (M+1) 349.25; HRMS Calcd. For C$_{17}$H$_{20}$N$_2$O$_4$S, 348.42. Found (M+1) 349.42.

The following are further non-limiting examples of prolyl hydroxylase inhibitors according to this category.

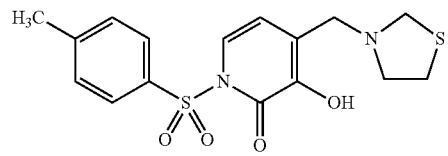

1-(4'-Methylbenzenesulfonyl)-3-hydroxy-4-thiazolidin-3-ylmethylpyridin-2(1H)-one: $^1$H NMR (300 MHz, DMSO) δ 2.43 (s, 3H), 2.94 (t, J=6.6 MHz, 2H), 3.18 (t, J=6.0 Hz, 2H), 3.66 (s, 2H), 4.12 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz, 1H), $^{19}$F NMR (252 MHz, DMSO) δ 87.9; $^{13}$C NMR (75 MHz, DMSO) δ 21.5, 21.9, 24.6, 25.8, 50.3, 51.6, 108.7, 118.6, 120.8, 129.7, 130.1, 133.1, 146.9, 148.1, 156.1, 158.4, 158.8; ES MS (M+1) 367.18; HRMS Calcd. For C$_{16}$H$_{18}$N$_2$O$_4$S$_2$, 366.46. Found (M+1) 367.43.

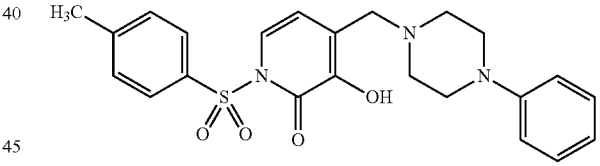

1-(4'-Methylbenzenesulfonyl)-3-hydroxy-4-azocan-1yl-methylpyridin-2(1H)-one: $^1$H NMR (300 MHz, DMSO) δ 1.59 (m, 10H), 2.44 (s, 3H), 3.17 (m, 2H), 3.32 (m, 2H), 4.15 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz); $^{19}$F NMR (252 MHz, DMSO) δ 88.7; $^{13}$C NMR (75 MHz, DMSO) δ 21.5, 21.9, 23.7, 24.6, 25.8, 50.3, 51.6, 108.7, 118.9, 120.8, 129.8, 130.1, 133.1, 146.9, 148.2, 156.1; ES MS (M+1) 391.18; HRMS Calcd. For C$_{20}$H$_{26}$N$_2$O$_4$S, 390.18. Found (M+1) 391.23.

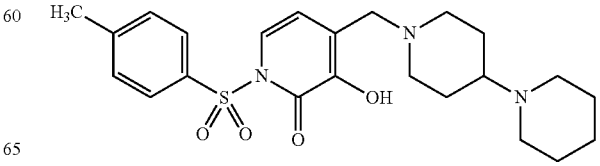

1-(4'-Methylbenzenesulfonyl)-3-hydroxy-4-(4-phenylpiperazin-1-ylmethyl)-pyridin-2(1H)-one: $^1$H NMR (300 MHz, DMSO) δ 2.43 (s, 3H), 3.13 (m, 8H), 3.43 (s, 2H), 6.47 (d, J=7.5 Hz, 1H), 6.78 (t, J=7.2 Hz, 1H), 7.21 9m, 2H), 7.50 (d, J=8.1 Hz, 2H), 7.67 (d, J=7.8 Hz, 1H), 7.97 (d, J=8.4 Hz, 2H); $^{13}$C NMR (75 MHz, DMSO) δ 21.5, 42.6, 45.6, 46.2, 50.8, 51.9, 109.6, 116.4, 116.8, 117.7, 120.6, 121.1, 129.5, 129.6, 129.8, 130.1, 133.2, 146.8, 149.5, 156.1; ES MS (M+1) 440.15; HRMS Calcd. For C$_{23}$H$_{25}$N$_3$O$_5$S, 439.53. Found (M+1) 440.16.

1-(4'-Methylbenzenesulfonyl)-3-hydroxy-4-[1,4']Bipiperidinyl-1'-ylmethylpyridin-2(1H)-one: $^1$H NMR (300 MHz, DMSO) δ 1.43 (m, 1 h), 1.67 (m, 2H), 1.82 (m, 4H), 2.19 (m, 2H), 2.44 (s, 3H), 2.94 (m, 4H), 3.39 (m, 2H), 3.54 (m, 3H), 4.06 (s, 2H), 6.47 (d, J=8.1 Hz, 1H), 7.51 (d, J=8.1 Hz, 2H), 7.73 (d, 7.8 Hz, 1H), 7.99 (d, J=8.4 Hz, 2H); $^{19}$F NMR (252 MHz, DMSO) δ 88.7; $^{13}$C NMR (75 MHz, DMSO) δ 21.4, 22.9, 23.6, 48.4, 49.5, 59.4, 109.3, 114.8, 117.6, 120.5, 122.7, 129.7, 130.1, 133.1, 146.9, 148.6, 156.2; ES MS (M+1) 446.19; HRMS Calcd. For $C_{23}H_{31}N_3O_4S$, 445.58. Found (M+1) 446.21.

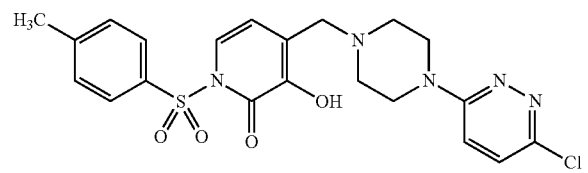

1-(4'-Methylbenzenesulfonyl)-3-hydroxy-4-[4-(6-chloropyridazin-3-yl)piperazin-1-ylmethyl]pyridin-2(1H)-one: $^1$H NMR (300 MHz, DMSO) δ 2.44 (s, 3H), 3.17 (m, 2H), 3.46 (m, 4H), 4.17 (s, 2H), 4.45 (m, 2H), 6.77 (d, J=7.8 Hz, 1H), 7.04 (m, 1H), 7.53 (m 2H), 7.68 (m, 2H), 7.98 (m, 2H), 11.3 (broad s, 1H), ES MS (M+1) 476.92. HRMS Calcd. For $C_{21}H_{25}ClN_5O_4S$, 475.95. Found (M+1) 476.11.

Category V of HIF-1α prolyl hydroxylase inhibitors relates to compounds having the formula:

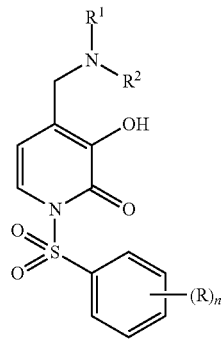

R represents from 1 to 5 optional substitutions for a phenyl ring hydrogen atom, $R^1$ and $R^2$ are each independently hydrogen or substituted or unsubstituted $C_1$-$C_{10}$ linear or branched alkyl, wherein the alkyl unit can be substituted by one or more units independently chosen from:

i) $C_1$-$C_8$ linear, $C_3$-$C_8$ branched, or $C_3$-$C_8$ cyclic alkoxy;

ii) hydroxy;

iii) halogen;

iv) cyano;

v) amino, $C_1$-$C_8$ mono-alkylamino, $C_1$-$C_8$ di-alkylamino;

vi) —$SR^{40}$; $R^{40}$ is hydrogen or $C_1$-$C_4$ linear or $C_3$-$C_4$ branched alkyl;

vii) substituted or unsubstituted $C_6$ of $C_{10}$ aryl;

viii) substituted or unsubstituted $C_1$-$C_9$ heterocyclic; or ix) substituted or unsubstituted $C_1$-$C_9$ heteroaryl.

Table V provides non-limiting examples of this category of HIF-1α prolyl hydroxylase inhibitors.

TABLE V

| No. | R | $R^1$ | $R^2$ |
|---|---|---|---|
| E1 | 4-methyl | benzyl | hydrogen |
| E2 | 4-methyl | 4-methoxybenzyl | hydrogen |
| E3 | 4-methyl | 4-fluorobenzyl | hydrogen |
| E4 | 4-methyl | 4-chlorobenzyl | hydrogen |
| E5 | 4-methyl | 4-methylbenzyl | hydrogen |
| E6 | 4-methyl | 2-(pyridin-2-yl)ethyl | hydrogen |
| E7 | 4-methyl | [1,3]dioxolan-2-ylmethyl | hydrogen |
| E8 | 4-methyl | tetrahydrofuran-2-ylmethyl | hydrogen |
| E9 | 4-methyl | 2-methoxyethyl | hydrogen |
| E10 | 4-methyl | 1-hydroxy-2-methylpropan-2-yl | hydrogen |
| E11 | 4-methyl | pyridin-4-ylmethyl | hydrogen |
| E12 | 4-methyl | furan-2-ylmethyl | hydrogen |
| E13 | 4-methyl | 2-(methylthio)ethyl | hydrogen |
| E14 | 4-methyl | 1-phenylethyl | hydrogen |
| E15 | 4-methyl | 3-imidazol-1-ylpropyl | hydrogen |
| E16 | 4-methyl | cycloheptyl | hydrogen |
| E17 | 4-methyl | 4-methylcyclohexyl | hydrogen |
| E18 | 4-methyl | 1-benzylpiperidin-4-yl | hydrogen |
| E19 | 4-methyl | azepan-2-on-3-yl | hydrogen |
| E20 | 4-methyl | 1-benzylpyrrolidin-3-yl | hydrogen |
| E21 | 4-methyl | benzyl | methyl |
| E22 | 4-methyl | 4-methoxybenzyl | methyl |
| E23 | 4-methyl | 4-fluorobenzyl | methyl |
| E24 | 4-methyl | 4-chlorobenzyl | methyl |
| E25 | 4-methyl | 4-methylbenzyl | methyl |
| E26 | 4-methyl | 2-(pyridin-2-yl)ethyl | methyl |
| E27 | 4-methyl | [1,3]dioxolan-2-ylmethyl | methyl |
| E28 | 4-methyl | tetrahydrofuran-2-ylmethyl | methyl |
| E29 | 4-methyl | 2-methoxyethyl | methyl |
| E30 | 4-methyl | 1-hydroxy-2-methylpropan-2-yl | methyl |
| E31 | 4-methyl | pyridin-4-ylmethyl | methyl |
| E32 | 4-methyl | furan-2-ylmethyl | methyl |
| E33 | 4-methyl | carboxymethyl | methyl |
| E34 | 4-methyl | 2-(methylthio)ethyl | methyl |
| E35 | 4-methyl | 1-phenylethyl | methyl |
| E36 | 4-methyl | 3-imidazol-1-ylpropyl | methyl |
| E37 | 4-methyl | cycloheptyl | methyl |
| E38 | 4-methyl | 4-methylcyclohexyl | methyl |
| E39 | 4-methyl | 1-benzylpiperidin-4-yl | methyl |
| E40 | 4-methyl | azepan-2-on-3-yl | methyl |
| E41 | 4-methyl | 1-benzylpyrrolidin-3-yl | methyl |

The disclosed compounds of this category can be prepared by the procedure outlined herein below in Scheme IV and described in Examples 4.

Scheme IV

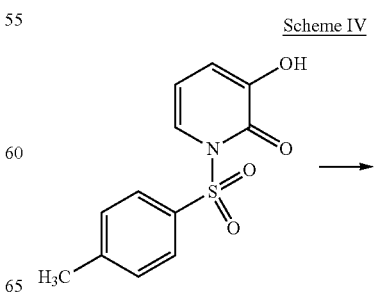

7

-continued

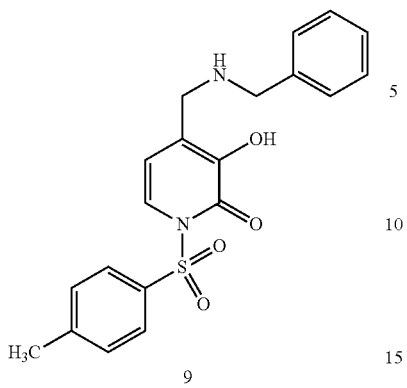

9

Reagents and conditions: (a) benzyl bromide, HCHO, H₂O/EtOH; rt, 12 hr.

Example 4

1-(4'-Methylbenzenesulfonyl)-3-hydroxy-4-[(benzylamino)methyl]-pyridin-2(1H)-one (9)

1-(4'-Methylbenzenesulfonyl)-3-hydroxy-4-(benzylaminomethyl)pyridin-2(1H)-one (9): 1-(4'-Methylbenzenesulfonyl)-3-hydroxypyridin-2(1H)-one (7) (250 mg, 0.94 mmol) and formaldehyde (200 mg, 2.07 mmol) are combined in aqueous ethanol (10 mL) and stirred for 30 minutes. Benzylamine (229 mg, 2.07 mmol) is then added and the reaction stirred for 12 hours. The solvent is removed by evaporation and the residue dissolved in methanol (5 mL) and purified via prep HPLC eluting with water/acetonitrile to afford the desired product as the trifluoracetate salt. $^1$H NMR (300 MHz, DMSO) d 2.44 (s, 3H), 3.96 (s, 2H), 4.16 (s, 2H), 6.69 (d, J=8.1 Hz), 7.40 (m, 7H), 7.52 (m, 1H), 7.73 (d, J=8.1 Hz, 1H), 7.97 (d, J=8.1 Hz, 1H), 9.71 (broad s, 2H), 10.44 (broad s, 1H); ES MS (M+1) 396.67; HRMS Calcd. For $C_{20}H_{20}N_2O_4S$, 384.45. Found (M+1) 385.12.

The following is a further non-limiting example of this category of HIF-1α prolyl hydroxylase inhibitors.

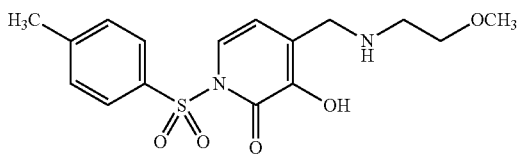

1-(4'-Methylbenzenesulfonyl)-3-hydroxy-4-[(2-methoxyethylamino)methyl]-pyridin-2(1H)-one:
$^1$H NMR (300 MHz, DMSO) δ 2.43 (s, 3H), 3.12 (m, 2H), 3.29 (s, 3H), 3.56 (t, J=5.1 Hz, 2H), 3.99 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz); $^{19}$F NMR (252 MHz, DMSO) δ 88.6; $^{13}$C NMR (75 MHz, DMSO) δ 21.5, 43.8, 46.2, 46.5, 58.5, 67.2, 106.7, 119.2, 120.2, 123.9, 128.4, 129.7, 130.1, 133.1, 146.8, 147.0, 156.0; ES MS (M+1) 353.12. HRMS Calcd. For $C_{16}H_{20}N_2O_5S$, 352.41. Found (M+1) 353.11.

Category VI of HIF-1α prolyl hydroxylase inhibitors relates to compounds having the formula:

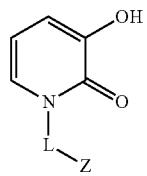

wherein L is chosen from $CH_2$ or $SO_2$, and Z is substituted or unsubstituted phenyl. Non-limiting examples of inhibitors according to this category are disclosed in Table VI below.

TABLE VI

| No. | L | Z |
| --- | --- | --- |
| F1 | $CH_2$ | 2-chlorophenyl |
| F2 | $CH_2$ | 3-chlorophenyl |
| F3 | $CH_2$ | 4-chlorophenyl |
| F4 | $CH_2$ | 2-fluorophenyl |
| F5 | $CH_2$ | 3-fluorophenyl |
| F6 | $CH_2$ | 4-fluorophenyl |
| F7 | $CH_2$ | 2,3-dichlorophenyl |
| F8 | $CH_2$ | 2,4-dichlorophenyl |
| F9 | $CH_2$ | 2,5-dichlorophenyl |
| F10 | $CH_2$ | 2,6-dichlorophenyl |
| F11 | $CH_2$ | 3,4-dichlorophenyl |
| F12 | $CH_2$ | 3,5-dichlorophenyl |
| F13 | $CH_2$ | 2,3-difluorophenyl |
| F14 | $CH_2$ | 2,4-difluorophenyl |
| F15 | $CH_2$ | 2,5-difluorophenyl |
| F16 | $CH_2$ | 2,6-difluorophenyl |
| F17 | $CH_2$ | 3,4-difluorophenyl |
| F18 | $CH_2$ | 3,5-difluorophenyl |
| F19 | $CH_2$ | 2-cyanophenyl |
| F20 | $CH_2$ | 3-cyanophenyl |
| F21 | $CH_2$ | 4-cyanophenyl |
| F22 | $SO_2$ | 2-chlorophenyl |
| F23 | $SO_2$ | 3-chlorophenyl |
| F24 | $SO_2$ | 4-chlorophenyl |
| F25 | $SO_2$ | 2-fluorophenyl |
| F26 | $SO_2$ | 3-fluorophenyl |
| F27 | $SO_2$ | 4-fluorophenyl |
| F28 | $SO_2$ | 2,3-dichlorophenyl |
| F29 | $SO_2$ | 2,4-dichlorophenyl |
| F30 | $SO_2$ | 2,5-dichlorophenyl |
| F31 | $SO_2$ | 2,6-dichlorophenyl |
| F32 | $SO_2$ | 3,4-dichlorophenyl |
| F33 | $SO_2$ | 3,5-dichlorophenyl |
| F34 | $SO_2$ | 2,3-difluorophenyl |
| F35 | $SO_2$ | 2,4-difluorophenyl |
| F36 | $SO_2$ | 2,5-difluorophenyl |
| F37 | $SO_2$ | 2,6-difluorophenyl |
| F38 | $SO_2$ | 3,4-difluorophenyl |
| F39 | $SO_2$ | 3,5-difluorophenyl |
| F40 | $SO_2$ | 2-cyanophenyl |
| F41 | $SO_2$ | 3-cyanophenyl |
| F42 | $SO_2$ | 4-cyanophenyl |

The compounds encompassed within this category can be prepared according to Scheme I for Z equal to $CH_2$ and according to Scheme III for Z equal to $SO_2$.

Pharmaceutically Acceptable Salts

The disclosed compounds useful for treating colitis and other inflammatory bowel diseases and syndromes can be in the form of a pharmaceutically acceptable salt. Pharmaceutically acceptable salts can be used by the formulator to provide a form of the disclosed inhibitor that is more compatible with the intended delivery of the inhibitor to a subject or for compatibility of formulation.

The following are examples of procedures for preparing the pharmaceutically acceptable salt of the disclosed inhibitor, tert-butyl-{[1-(4-chlorobenzyl)-3-hydroxy-2-oxo-1,2-dihydropyridin-4-yl]methyl}piperazine-1-carboxylate.

A suspension of tert-butyl-{[1-(4-chlorobenzyl)-3-hydroxy-2-oxo-1,2-dihydropyridin-4-yl]methyl}piperazine-1-carboxylate (242 mg, 0.56 mmol) in MeOH (15 mL) was heated at reflux until a homogeneous solution was obtained. Heating was stopped and 0.1N HCl (6.7 mL, 1.2 eq.) was added while still hot and the solution was cooled to room temperature. The volatiles were evaporated under reduced pressure and the amorphous residue was crystallized in acetone (5 mL). The solid was collected by filtration.

A suspension of tert-butyl-{[1-(4-chlorobenzyl)-3-hydroxy-2-oxo-1,2-dihydropyridin-4-yl]methyl}piperazine-1-carboxylate (217 mg, 0.5 mmol) in MeOH (15 mL) was heated at reflux until a homogeneous solution was obtained. Heating was stopped and methanesulfonic acid (115.2 mg, 1.2 eq.) was added while still hot and the solution was cooled to room temperature. The volatiles were evaporated under reduced pressure and the amorphous residue was crystallized in acetone (5 mL). The solid was collected by filtration.

Table VII herein below provides examples of pharmaceutically acceptable salts of tert-butyl-{[1-(4-chlorobenzyl)-3-hydroxy-2-oxo-1,2-dihydropyridin-4-yl]methyl}-piperazine-1-carboxylate formed from organic and inorganic acids. Start

TABLE VII

| Acid | Yield | Purity* | M.P. (° C.) | color |
|---|---|---|---|---|
| Free base | — | 99.3% | 183-184 | pink |
| HCl | 90% | 99.7% | 185-186 | white |
| H$_2$SO$_4$ | 93% | 99.7% | 175 (dec.) | slightly pink |
| p-toluenesulfonyl | 74% | 99.8% | 185-186 | white |
| methanesulfonyl | 79% | 99.9% | 155-157 | white |

*Determined by HPLC analysis $^1$H NMR analysis was used to determine the form of the salt, for example, that the mesylate salt formed herein above had the following formula:

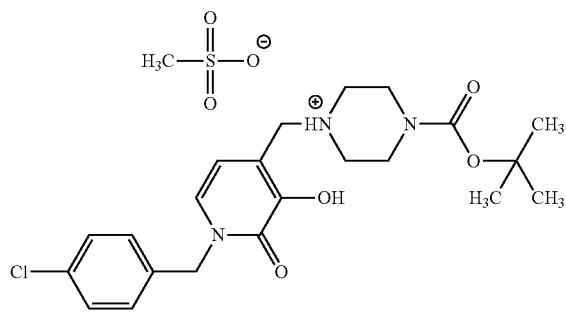

$^1$H NMR analysis was used to determine at which position in the molecule that salt formation was taking place. The chemical shifts for the protons on the methylene group bridging the piperazine and the pyridinone rings shifted from 3.59 ppm in the free base to 4.31 ppm of the salt. In addition, the piperazine methylene groups adjacent to the tertiary amine shifted from 2.50 ppm to approximately 3.60 ppm. The chemical shifts for the remaining protons were largely unchanged. These data indicate that the tertiary amine nitrogen of the piperazine ring is protonated in salt forms. In addition, integration of the methyl protons of the methane sulfonyl unit relative to the core compound indicates the presence of one equivalent of the acid.

The formulator can determine the solubility of the pharmaceutically acceptable salts of the disclosed inhibitors by any method desirable. The following is a non-limiting example of a procedure for evaluating the solubility of a salt of a disclosed inhibitor. A suspension of tert-butyl-{[1-(4-chlorobenzyl)-3-hydroxy-2-oxo-1,2-dihydropyridin-4-yl]methyl}-piperazine-1-carboxylate methanesulfonate (26.6 mg) in distilled deionized water (3.0 mL) is sonicated for 20 min with water bath temperature under 25° C. The suspension is filtered to remove any insoluble salt. The clear filtrate solution (200 µL) is diluted with distilled deionized water (800 µL) and subjected to HPLC analysis. The following are results for the pharmaceutically acceptable salts outlined in Table VII above.

| Salt | Solubility (mg/mL) | Purity* |
|---|---|---|
| Free base | ~0.001 | 99.3% |
| hydrochloride | 5.9 | 99.7% |
| hydrogensulfonate | 13.2 | 99.7% |
| p-toluenesulfonate | 2.3 | 99.8% |
| methanesulfonate | 16.6 | 99% |

*Determined by HPLC analysis

The following are non-limiting examples of other acids that can be used to form pharmaceutically acceptable salts of the disclosed inhibitors: acetate, citrate, maleate, succinate, lactate, glycolate, tartrate, bromide, iodide, sulfate, bisulfate, carbonate, bicarbonate, phosphate, formate, propionate, butyrate, pyruvate, oxalate, malonate, fumarate, and the like.

Acute and chronic inflammation of the bowel is caused by a number of diseases. Typically the epithelial cells on the surface of mucosal tissue have an induced state of hypoxia due to the presence of inflammation. The body's response to this hypoxic condition is to increase the presence of hypoxia inducible factor-1 alpha (HIF-1α) which drives the expression of downstream HIF-1 target genes, inter alia, erythropoietin. As such, HIF-1α is an important mediator in the body's response to inflammation. The cellular concentration of HIF-1α is regulated by prolyl hydroxylase enzymes that serve to destabilize HIF-1α during periods of normoxia resulting in the destruction of this protein.

Inhibition of HIF-1α prolyl hydroxylase thus leads to increased stabilization of HIF-1α resulting in up regulation of HIF-1 which leads to a corresponding increased response to inflammation. In subjects suffering from one or more inflammatory epithelial diseases, treatment with one or more effective HIF-1α prolyl hydroxylase inhibitors can increase the level of the body's cellular inflammatory response. In addition, during periods of low inflammation in the case of chronic diseases, HIF-1α prolyl hydroxylase inhibitors can increase the amount of epithelial cell healing over that which the body would normally provide. As such, administration of one or more HIF-1α prolyl hydroxylase inhibitors to a subject suffering from an inflammatory disease such as Crohn's disease, or alternatively to a subject diagnosed with an inflammatory disease provides a method for curing, controlling, mediating, reducing, or otherwise affecting the severity of the condition.

Methods

Disclosed herein are methods for treating a subject having or suffering from one or more diseases or conditions affecting intestinal epithelial tissue. In one aspect, disclosed herein is a method for treating a subject having an inflammatory bowel disease, comprising administering to the subject an effective amount of one or more of the disclosed HIF-1α prolyl hydroxylase inhibitors or pharmaceutically acceptable salts thereof. Non-limiting examples of inflammatory bowel diseases includes Crohn's disease, ulcerative colitis, collagenous colitis, lymphocytic colitis, ischemic colitis, diversion colitis, Behçet's syndrome, and indeterminate colitis. As such, disclosed are the following methods. The disclosed methods also relate to methods for treating a subject that is diagnosed with one or more of the following conditions, syndromes, illnesses, pathologies, maladies, diseases, and the like.

A method for treating Crohn's disease in a subject, comprising administering to the subject an effective amount of one or more of the disclosed HIF-1α prolyl hydroxylase inhibitors or pharmaceutically acceptable salts thereof. One embodiment of this method relates to administering to a subject with Crohn's disease an effective amount of a pharmaceutical composition as disclosed herein. Another embodiment of this method relates to administering to a subject with Crohn's disease an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating ulcerative colitis in a subject, comprising administering to the subject an effective amount of one or more of the disclosed HIF-1α prolyl hydroxylase inhibitors or pharmaceutically acceptable salts thereof. One embodiment of this method relates to administering to a subject with ulcerative colitis an effective amount of a pharmaceutical composition as disclosed herein. Another embodiment of this method relates to administering to a subject with ulcerative colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating collagenous colitis in a subject, comprising administering to the subject an effective amount of one or more of the disclosed HIF-1α prolyl hydroxylase inhibitors or pharmaceutically acceptable salts thereof. One embodiment of this method relates to administering to a subject with collagenous colitis an effective amount of a pharmaceutical composition as disclosed herein. Another embodiment of this method relates to administering to a subject with collagenous colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating lymphocytic colitis in a subject, comprising administering to the subject an effective amount of one or more of the disclosed HIF-1α prolyl hydroxylase inhibitors or pharmaceutically acceptable salts thereof. One embodiment of this method relates to administering to a subject with lymphocytic colitis an effective amount of a pharmaceutical composition as disclosed herein. Another embodiment of this method relates to administering to a subject with lymphocytic colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating ischemic colitis in a subject, comprising administering to the subject an effective amount of one or more of the disclosed HIF-1α prolyl hydroxylase inhibitors or pharmaceutically acceptable salts thereof. One embodiment of this method relates to administering to a subject with ischemic colitis an effective amount of a pharmaceutical composition as disclosed herein. Another embodiment of this method relates to administering to a subject with ischemic colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating diversion colitis in a subject, comprising administering to the subject an effective amount of one or more of the disclosed HIF-1α prolyl hydroxylase inhibitors or pharmaceutically acceptable salts thereof. One embodiment of this method relates to administering to a subject with diversion colitis an effective amount of a pharmaceutical composition as disclosed herein. Another embodiment of this method relates to administering to a subject with diversion colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating ulcerative colitis in a subject, comprising administering to the subject an effective amount of one or more of the disclosed HIF-1α prolyl hydroxylase inhibitors or pharmaceutically acceptable salts thereof. One embodiment of this method relates to administering to a subject with ulcerative colitis an effective amount of a pharmaceutical composition as disclosed herein. Another embodiment of this method relates to administering to a subject with ulcerative colitis an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

A method for treating Behçet's syndrome in a subject, comprising administering to the subject an effective amount of one or more of the disclosed HIF-1α prolyl hydroxylase inhibitors or pharmaceutically acceptable salts thereof. One embodiment of this method relates to administering to a subject with Behçet's syndrome an effective amount of a pharmaceutical composition as disclosed herein. Another embodiment of this method relates to administering to a subject with Behçet's syndrome an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

Further disclosed herein are methods for treating a subject having or suffering from one or more inflammatory epithelial diseases conditions, syndromes, illnesses, pathologies, maladies and the like. In one aspect, disclosed herein is a method for treating a subject having inflammatory epithelial disease of the respiratory tract, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the respiratory tract an effective amount of a pharmaceutical composition as disclosed herein. Another embodiment of this method relates to administering to a subject having inflammatory epithelial disease of the respiratory tract an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

In another aspect, disclosed herein is a method for treating a subject having inflammatory epithelial disease of the mucosa, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the mucosa an effective amount of a pharmaceutical composition as disclosed herein. Another embodiment of this method relates to administering to a subject having inflammatory epithelial disease of the mucosa an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

In a further aspect, disclosed herein is a method for treating a subject having inflammatory epithelial disease of the skin, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the skin an effective amount of a pharmaceutical composition as disclosed herein. Another embodiment of this method relates to administering to a subject having inflammatory epithelial disease of the skin an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

In a still further aspect, disclosed herein is a method for treating a subject having inflammatory epithelial disease of the GI tract, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the GI tract an effective amount of a pharmaceutical composition as disclosed herein. Another embodiment of this method relates to administering to a subject having inflammatory epithelial disease of the GI tract an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

In a yet still further aspect, disclosed herein is a method for treating a subject having inflammatory epithelial disease of the lining of one or more major organs and/or endocrine glands, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the lining of one or more major organs and/or endocrine glands an effective amount of a pharmaceutical composition as disclosed herein. Another embodiment of this method relates to administering to a subject having inflammatory epithelial disease of the lining of one or more major organs and/or endocrine glands an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

In a still another aspect, disclosed herein is a method for treating a subject having inflammatory epithelial disease of the vascular tissue, comprising administering to the subject an effective amount of one or more of the disclosed HIF-1α prolyl hydroxylase inhibitors or pharmaceutically acceptable salts thereof. One embodiment of this method relates to administering to a subject having inflammatory epithelial disease of the vascular tissue an effective amount of a pharmaceutical composition as disclosed herein. Another embodiment of this method relates to administering to a subject having inflammatory epithelial disease of the vascular tissue an effective amount of a pharmaceutical composition as disclosed herein that comprises an effective amount of one or more of the disclosed HIF-1α prolyl hydroxylase inhibitors or pharmaceutically acceptable salts thereof in combination with an effective amount of one or more other pharmaceutical agents.

Still further disclosed herein is the use of an effective amount of one or more of the disclosed HIF-1α prolyl hydroxylase inhibitors or pharmaceutically acceptable salts thereof for making a medicament to treat an inflammatory disease in intestinal epithelial tissue, such as inflammatory bowel disease, including Crohn's disease, ulcerative colitis, collagenous colitis, lymphocytic colitis, ischemic colitis, diversion colitis, Behçet's syndrome, and indeterminate colitis. Also disclosed herein is the use of an effective amount of one or more of the disclosed HIF-1α prolyl hydroxylase inhibitors or pharmaceutically acceptable salts thereof for making a medicament to treat an inflammatory epithelial disease, including the respiratory tract, mucosa, skin, GI tract, lining of major organs and endocrine glands, and vascular tissue.

Formulations

Medicaments and Pharmaceutical Compositions

The present disclosure further relates to pharmaceutical compositions that can be used as a method for treating one or more of the disclosed diseases. In addition, the disclosed formulations can be used for making a medicament or a pharmaceutical composition useful for treating one or more of the disclosed diseases, conditions, ailments, syndromes, and the like. The disclosed medicaments or pharmaceutical compositions comprise an effective amount of one or more HIF-1α prolyl hydroxylase inhibitors or pharmaceutically acceptable salts thereof according to the present disclosure.

One aspect of the disclosed compositions comprises:
  a) an effective amount of one or more of the disclosed HIF-1α prolyl hydroxylase inhibitors or a pharmaceutically acceptable salt thereof; and
  b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:
- a) from about 0.001 mg to about 1000 mg of one or more disclosed HIF-1α prolyl hydroxylase inhibitors or a pharmaceutically acceptable salt thereof; and
- b) one or more excipients.

Another example according to the present disclosure relates to the following compositions:
- a) from about 0.01 mg to about 100 mg of one or more disclosed HIF-1α prolyl hydroxylase inhibitors or a pharmaceutically acceptable salt thereof; and
- b) one or more excipients.

A further example according to the present disclosure relates to the following compositions:
- a) from about 0.1 mg to about 10 mg of one or more disclosed HIF-1α prolyl hydroxylase inhibitors or a pharmaceutically acceptable salt thereof; and
- b) one or more excipients.

A still further example of compositions according to the present disclosure comprise:
- a) an effective amount of one or more disclosed HIF-1α prolyl hydroxylase inhibitors or a pharmaceutically acceptable salt thereof; and
- b) one or more chemotherapeutic agents or chemotherapeutic compounds as further described herein.

One category of chemotherapeutic agents or chemotherapeutic compounds includes cytotoxic drugs, for example, 6-hydroxymethylacylfulvene, cyclophosphamide, dacarbazine, carmustine, doxorubicin, and methotrexate.

Another category of chemotherapeutic agents or chemotherapeutic compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel;

docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Other chemotherapeutic agents that can be used in combination with the disclosed HIF-1α inhibitors include, but are not limited to, mitotic inhibitors (vinca alkaloids). These include vincristine, vinblastine, vindesine and Navelbine™ (vinorelbine, 5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed HIF-1α prolyl hydroxylase inhibitors herein can be administered in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

A yet still further example of compositions according to the present disclosure comprise:
a) an effective amount of one or more disclosed HIF-1α prolyl hydroxylase inhibitors or a pharmaceutically acceptable salt thereof; and
b) one or more vaccines for treatment of an infectious disease.

The disclosed compositions and the form of pharmaceutical preparations comprising the compounds useful for treating colitis and other inflammatory bowel diseases and syndromes alone, or in combination with another drug or other therapeutic agent, inter alia, chemotherapeutic agent or chemotherapeutic compound, can vary according to the intended route of administration.

Orally administered preparations can be in the form of solids, liquids, emulsions, suspensions, or gels, or in dosage unit form, for example as tablets or capsules. Tablets can be compounded in combination with other ingredients customarily used, such as talc, vegetable oils, polyols, gums, gelatin, starch, and other carriers. The compounds useful for treating colitis and other inflammatory bowel diseases and syndromes can be dispersed in or combined with a suitable liquid carrier in solutions, suspensions, or emulsions.

Parenteral compositions intended for injection, either subcutaneously, intramuscularly, or intravenously, can be prepared as liquids or solid forms for solution in liquid prior to injection, or as emulsions. Such preparations are sterile, and liquids to be injected intravenously should be isotonic. Suitable excipients are, for example, water, dextrose, saline, and glycerol.

Administration of pharmaceutically acceptable salts of the substances described herein is included within the scope of the present disclosure. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., *Journal of Pharmaceutical Sciences* 66:1-19 (1977) the disclosure of which is hereby incorporated by reference.

Substances for injection can be prepared in unit dosage form in ampules, or in multidose containers. The compounds useful for treating colitis and other inflammatory bowel diseases and syndromes or compositions comprising one or more compounds useful for treating colitis and other inflammatory bowel diseases and syndromes to be delivered can be present in such forms as suspensions, solutions, or emulsions in oily or preferably aqueous vehicles. Alternatively, the salt of the HIF-1α prolyl hydroxylase inhibitor can be in lyophilized form for reconstitution, at the time of delivery, with a suitable vehicle, such as sterile pyrogen-free water. Both liquids as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms can further comprise suitable formulatory agents, such as starch or sugar, glycerol or saline. The compositions per unit dosage, whether liquid or solid, can contain from 0.1% to 99% of polynucleotide material.

Procedures

EGLN-1 Activity Assay

The EGLN-1 (or EGLN-3) enzyme activity is determined using mass spectrometry (matrix-assisted laser desorption ionization, time-of-flight MS, MALDI-TOF MS. Recombinant human EGLN-1-179/426 is prepared as described above and in the Supplemental Data. Full-length recombinant human EGLN-3 is prepared in a similar way, however it is necessary to use the His-MBP-TVMV-EGLN-3 fusion for the assay due to the instability of the cleaved protein. For both enzymes, the HIF-1α peptide corresponding to residues 556-574 is used as substrate. The reaction is conducted in a total volume of 50 μL containing TrisCl (5 mM, pH 7.5), ascorbate (120 μM), 2-oxoglutarate (3.2 μM), HIF-1α (8.6 μM), and bovine serum albumin (0.01%). The enzyme, quantity predetermined to hydroxylate 20% of substrate in 20 minutes, is added to start the reaction. Where inhibitors are used, compounds are prepared in dimethyl sulfoxide at 10-fold final assay concentration. After 20 minutes at room temperature, the reaction is stopped by transferring 10 μL of reaction mixture to 50 μL of a mass spectrometry matrix solution (α-cyano-4-hydroxycinnamic acid, 5 mg/mL in 50% acetonitrile/0.1% TFA, 5 mM $NH_4PO_4$). Two microliters of the mixture is spotted onto a MALDI-TOF MS target plate for analysis with an Applied Biosystems (Foster City, Calif.) 4700 Proteomics Analyzer MALDI-TOF MS equipped with a Nd:YAG laser (355 nm, 3 ns pulse width, 200 Hz repetition rate). Hydroxylated peptide product is identified from substrate by the gain of 16 Da. Data defined as percent conversion of substrate to product is analyzed in GraphPad Prism 4 to calculate $IC_{50}$ values.

VEGF ELISA Assay

HEK293 cells are seeded in 96-well poly-lysine coated plates at 20,000 cells per well in DMEM (10% FBS, 1% NEAA, 0.1% glutamine). Following overnight incubation, the cells are washed with 100 μL of Opti-MEM (Gibco, Carlsbad, Calif.) to remove serum. Compound in DMSO is serially diluted (beginning with 100 μM) in Opti-MEM and added to the cells. The conditioned media is analyzed for VEGF with a Quantikine human VEGF immunoassay kit (R&D Systems, Minneapolis, Minn.). Optical density measurements at 450 nm are recorded using the Spectra Max 250 (Molecular Devices, Sunnyvale, Calif.). Data defined as % of DFO stimulation is used to calculate $EC_{50}$ values with GraphPad Prism 4 software (San Diego, Calif.).

Mouse Ischemic Hindlimb Study

All animal work is conducted in accordance with the Guide for the Care and Use of Laboratory Animals (National Academy of Sciences; Copyright©1996). Used in these experiments were 9-10 week old male C57Bl/6 mice from Charles River Laboratory (Portage, Mich.). The mice are orally dosed with vehicle (aqueous carbonate buffer, 50 mM; pH 9.0) or with the compound to be tested in vehicle at 50 mg/kg or 100 mg/kg. The animals are dosed three times: day 1 at 8 AM and 5 PM, and on day 2 at 8 AM. One hour after the first dose, unilateral arterial ligation is performed under anesthesia using isoflurane. The femoral artery is ligated proximal to the origin of the popliteal artery. The contralateral limb undergoes a sham surgical procedure. Ligation is performed in an alternating fashion between right and left hindlimbs. Two hours after the 8 AM dosing on day 2, blood is obtained by ventricular stick while the mice are anesthetized with isoflurane. Serum samples for EPO analysis are obtained using gel clot serum separation tubes. Heart, liver, and gastrocnemius muscles are harvested, snap-frozen in liquid nitrogen, and stored in −80° C. until use.

Mouse Serum EPO Assay

The mouse serum EPO is detected using Mouse Quantikine Erythropoietin ELISA kit from R&D Systems according to manufacturer's instructions.

Mouse Tissue HIF Western Blot Analysis

Tissues from mice stored at −80° C. are powdered with mortar and pestle chilled with liquid nitrogen. Nuclear extracts are prepared using an NE-PER kit (Pierce Biotechnology). For immunoprecipitation, nuclear extract is added to monoclonal antibody to HIF-1α (Novus, Littleton, Colo.) at a tissue to antibody ratio of 200:1. The suspension is incubated in a conical micro centrifuge tube for 4 hours at 4° C. Protein A/G-coupled agarose beads (40 μL of a 50% suspension) are then added to the tube. Following overnight tumbling at 4° C., the beads are washed 3 times with ice-cold phosphate buffered saline. The beads are then prepared for SDS-PAGE with 40 μL of Laemmli sample buffer. Proteins separated on SDS-PAGE are transferred onto nitrocellulose sheets with XCell-II Blot Module system (Invitrogen, Carlsbad, Calif.). The blots are blocked with 5% BSA prior to incubation with a rabbit antibody to HIF-1α at 1:100 dilution (Novus). The blots are then washed with Tris-buffered saline/Tween-20 buffer and incubated with horseradish peroxidase-conjugated goat anti-rabbit secondary antibody (Pierce, Rockford, Ill.). Blots are developed with the ECL reagent (Amersham, Piscataway, N.J.). Images of blots are captured with an Epson Expression 1600 scanner.

Table VIII below provides non-limiting examples of the in vivo response for compounds according to the present disclosure, for example, HIFPH2 (EGLN1) inhibition and VEGF stimulation.

TABLE VIII

| No. | Compound | HIFPH2 IC$_{50}$ (μM) | VEGF IC$_{50}$ (μM) |
|---|---|---|---|
| C17 | 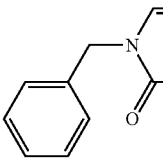<br>1-benzyl-3-hydroxy-4-[(4-methylcyclohexylamino)methyl]pyridin-2(1H)-one | 11 | 27.4 |
| C35 | 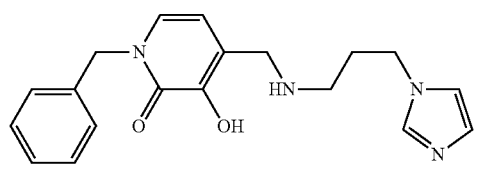<br>1-benzyl-3-hydroxy-4-{[3-(1H-imidazol-1-yl)propylamino]methyl}pyridin-2(1H)-one | 12 | 42.5 |
| C14 | 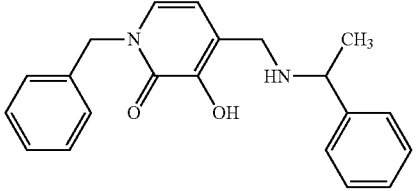<br>1-benzyl-3-hydroxy-4-[(1-phenylethylamino)methyl]pyridin-2(1H)-one | 12 | 20.6 |

TABLE VIII-continued

| No. | Compound | HIFPH2 IC$_{50}$ (μM) | VEGF IC$_{50}$ (μM) |
|---|---|---|---|
| B5 | (R)-1-benzyl-3-hydroxy-4-{[2-(methoxymethyl)pyrrolidin-1-yl]methyl}pyridin-2(1H)-one | 9 | 53 |
| C33 | 1-benzyl-3-hydroxy-4-{[2-(methylthio)ethylamino]methyl}pyridin-2(1H)-one | 16 | 53 |
| B14 | 1-benzyl-3-hydroxy-4-{[4-(6-chloropyridazin-3-yl)piperazin-1-yl]methyl}pyridin-2(1H)-one | 11 | 78 |
| C19 | 3-[(1-benzyl-3-hydroxy-2-oxo-1,2-dihydropyridin-4-yl)methylamino]azepan-2-one | 12 | 62.9 |
| B9 | 1-benzyl-3-hydroxy-4-[(4-benzylpiperazin-1-yl)methyl]pyridin-2(1H)-one | 17 | 12.6 |

TABLE VIII-continued

| No. | Compound | HIFPH2 IC$_{50}$ (μM) | VEGF IC$_{50}$ (μM) |
|---|---|---|---|
| A18 | 1-(2-methoxybenzyl)-3-hydroxy-4-(azepan-1-ylmethyl)pyridin-2-(1H)-one | 18 | 29.2 |
| D10 | 1-[(4-methylphenyl)sulfonyl]-3-hydroxy-4-(1,4'-bipiperidin-1'-ylmethyl)pyridin-2(1H)-one | 4.4 | 27 |
| D14 | 1-[(4-methylphenyl)sulfonyl]-3-hydroxy-4-{[4-(6-chloropyridazin-3-yl)piperazin-1-yl]methyl}pyridin-2(1H)-one | 12 | 19 |
| C1 | 1-(4-chlorobenzyl)-3-hydroxy-4-[(4-benzylamino)methyl]pyridin-2-(1H)-one | 12 | 42 |

TABLE VIII-continued

| No. | Compound | HIFPH2 IC$_{50}$ (µM) | VEGF IC$_{50}$ (µM) |
|---|---|---|---|
| A41 | tert-butyl 4-{[1-(4-chlorobenzyl)-3-hydroxy-2-oxo-1,2-dihydropyridin-4-yl]methyl}piperazine-1-carboxylate | 14 | 16.6 |
| E33 | 2-{[(3-hydroxy-2-oxo-1-tosyl-1,2-dihydropyridin-4-yl)methyl](methyl)amino}acetic acid | 21 | 2.1 |
| F3 | 1-(4-chlorobenzyl)-3-hydroxypyridin-2(1H)-one | 1.2 | 7.4 |
| F2 | 1-(3-chlorobenzyl)-3-hydroxypyridin-2(1H)-one | 5 | >100 |

Compound F2 was further tested in the mouse serum EPO assay described herein above and found to have an EPO EC$_{50}$=14 µM.

The disclosed compounds, compositions and methods stabilize HIF-1α and HIF-2α, as well as other factors that are present in a compromised immune system or which is depleted or over taxed by the presence of a disease state and the manifestations of the disease state, inter alia, diarrhea and intestinal pain. The disclosed compounds can be used to treat colitis and other inflammatory bowel diseases, inter alia, indeterminate colitis, Crohn's disease, irritable bowel syndrome and ischemic colitis and can be co-administered with other bowel disease therapy drug.

Induced Colitis Study

Colitis was induced in the subject animals using 2,4,6-trinitrobenzenesulfonic acid (TNBS) as described in Karhausen J O, et al. "Epithelial hypoxia inducible factor-1 is protective in murine experimental colitis." *J. Clin. Invest.* 2004; 114:1098-1106. Briefly, mice were sensitized by epicutaneous application of 1% TNBS (Sigma-Aldrich) in 100% ethanol on days 1-7, followed by intrarectal administration of 5 µL/g body weight of 2.5% TNBS solution in 50% ethanol on day +7. Vehicle-control animals received a corresponding volume of 50% ethanol alone. Only animals that showed an initial response to treatment were included in the study; this response was defined as a 5% loss of weight after induction of colitis. As a further parameter, colon length was determined by measurement of the distance from the most distal aspect of the cecum to the most terminal aspect of the rectum.

Compound A41 was administered daily via 100 mL subcutaneous injection to the scruff of the neck. Animals were treated with either 0.3, 1.0, or 5.0 mg/kg of a compound disclosed in Table VIII or 100 µL cyclodextrin vehicle. Molting and baldness was observed at the injection sites in all groups. Mild fibrosis was also observed during post-mortem examination due to repeated injection at the site of the scruff and vehicle build up.

Animals' weights were measured every 24 hours over the course of the experiment from one day prior to disease induction (Day −1). Upon sacrifice, colon length was measure to assess fibrosis and shortening. The colons were excised for analysis. Samples were taken and fixed in 4% formalin for histological analysis. Blood was taken by cardiac puncture for hematocrit analysis and the remainder stored for serum analysis.

FIG. 1 depicts the results of this study. The control group that did not receive TNSB-induced colitis and only received vehicle is shown by the line indicated with solid circles (●). This line is flat and shows that essentially no weight was lost by this group. The data represented by solid squares (■) represent control animals that had TNSB-induced colitis and only received pre-treatment with vehicle. Therefore, for the two groups of animals not receiving a pre-treatment dose of a compound disclosed in Table VIII, solid circles (●) represent healthy animals while solid squares (■) represent animals with TNSB-induced colitis. Comparing these two lines, it is evidenced that TNSB-induced colitis caused at least about 20% weight loss in untreated animals having induced disease.

Animals having TNSB-induced colitis that were pre-treated with 5 mg/kg of a compound disclosed in Table VIII (open circles (○)) maintained their weight during the course of this study. Animals without TNSB-induced colitis that were pre-treated with 5 mg/kg of a compound disclosed in Table VIII (solid triangles (▲)) had a slight weight loss but the body mass returned to near normal during the course of this study.

Animals having TNSB-induced colitis that were pre-treated with 1 mg/kg of a compound disclosed in Table VIII (solid diamonds (♦)) lost about 10% of their body mass by day 1, but began to recover body mass during the balance of the study. Animals having TNSB-induced colitis that were pre-treated with 0.3 mg/kg of a compound disclosed in Table VIII (solid inverted triangles (▼)) lost less of their body mass at a slower rate by day 3.

FIGS. 2a, 2b, and 2c depict the reversal of three clinical disease indicators for animals within 4 days of the study. Colon length is a marker of colonic inflammation and is reflected as increased shortening due to increased fibrosis associated with the inflammation.

FIG. 2a depicts the percent colon length found in the following treatment groups: (A) healthy mice; (B) mice having TNBS-induced colitis treated with 5 mg/kg a compound disclosed in Table VIII from Day −1; (C) mice having TNBS-induced colitis treated with 5 mg/kg a compound disclosed in Table VIII from Day +2; and (D) mice having TNBS-induced colitis receiving only vehicle.

FIG. 2b depicts the disease activity scores for the animals treated in this study. Severity of inflammation was documented macroscopically, considering changes of bodyweight and general appearance (hair, liveliness). Stools and rectal bleeding, and color, distension and serosal appearance of the colon directly after opening of the abdomen were scored. A maximum macroscopic score of 12 points was allocated, according to the following: as adolescent mice gain at least 5% bodyweight per week, change of bodyweight of more than 5% was scored 0, 0-5% gain=1, loss of bodyweight=2. Hair was normal (0) or dull (1); mice were lively (0) or apathetic (1). Stools were normal (0), semiliquid (1) or liquid (2). Rectal bleeding was given 1 point. Colon colour was normal (0) or red (1); distention was absent (0) or remarkable (1). The serosal aspect was normal (0) or thickened (1). The groups depicted in FIG. 2b are as follows: (A) healthy mice; (B) mice having TNBS-induced colitis treated with 5 mg/kg a compound disclosed in Table VIII from Day −1; (C) mice having TNBS-induced colitis treated with 5 mg/kg a compound disclosed in Table VIII from Day +2; and (D) mice having TNBS-induced colitis receiving only vehicle.

See Cooper H S et al. "Clinicopathologic study of dextran sulfate sodium experimental murine colitis." *Lab Invest.* 1993 August; 69(2):238-249.

FIG. 2c shows the mesenteric lymph node (MLN) total leukocyte count for animals receiving vehicle (A), TNBS induced colitis receiving only ethanol vehicle (B), animals without TNBS induced colitis receiving 10 mg/kg a compound disclosed in Table VIII (C); and animals having TNBS-induced colitis and receiving 10 mg/kg a compound disclosed in Table VIII (D). As can be seen from these data, the animals receiving a treatment with a compound disclosed in Table VIII had a lower leukocyte count than animals with induced colitis receiving no drug.

Figure 3:
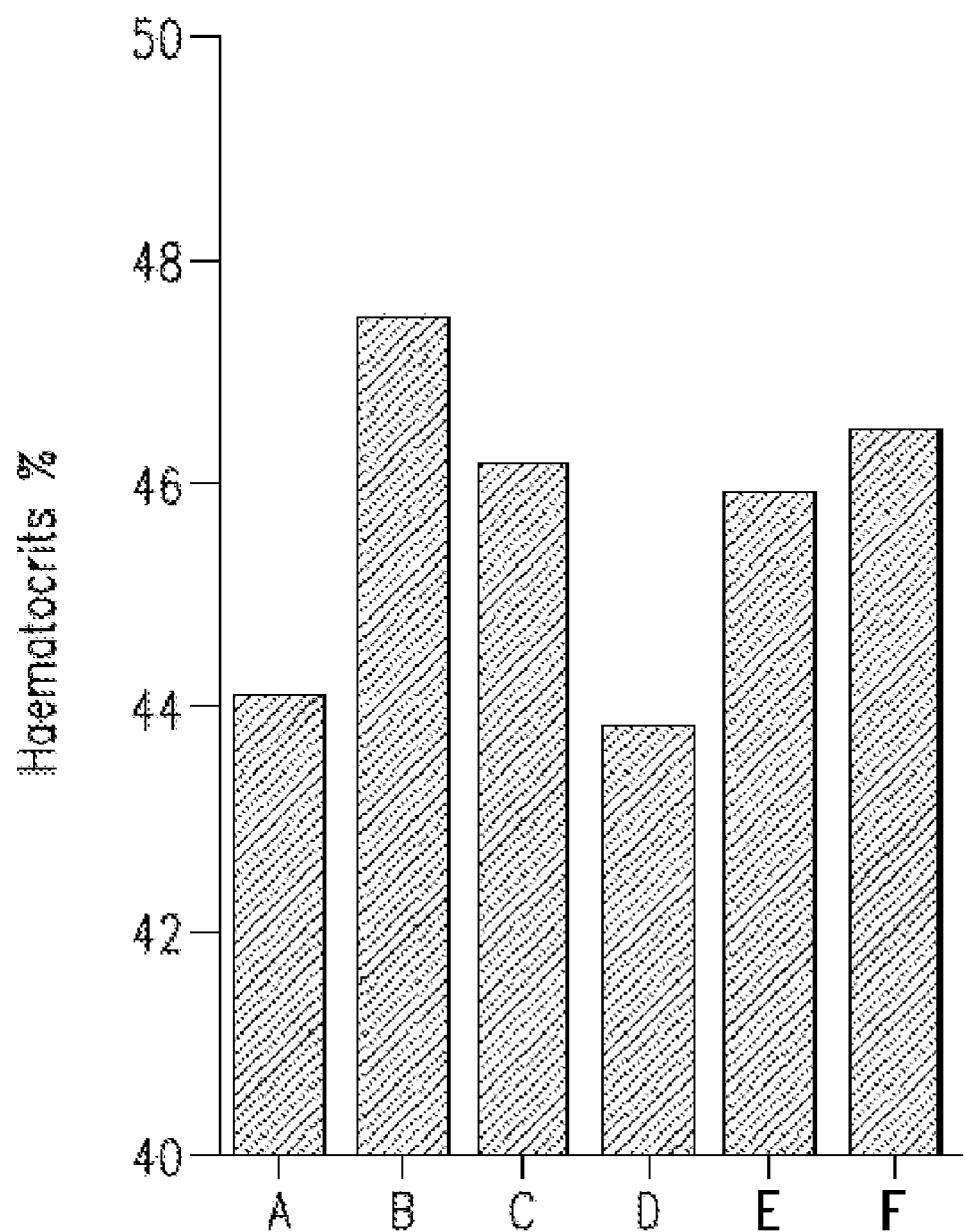
FIG. 3 depicts the change in hematocrit levels for the various groups in this study. Group A (healthy control) was not subjected to TNBS-induced colitis and only received pre-treatment with vehicle; Group B was subjected to TNBS-induced colitis and only received pre-treatment with vehicle; Group C was not subjected to TNBS-induced colitis and received a pre-treatment of 5 mg/kg of a compound disclosed in Table VIII; Group D was subjected to TNBS-induced colitis and received a pre-treatment of 0.3 mg/kg of a compound disclosed in Table VIII; Group E was subjected to TNBS-induced colitis and received a pre-treatment with 1 mg/kg of a compound disclosed in Table VIII; and Group F was subjected to TNBS-induced colitis and received a pre-treatment with 5 mg/kg of a compound disclosed in Table VIII.

FIG. 3 depicts the change in hematocrit levels for the various groups in this study. Group A (healthy control) was not subjected to TNSB-induced colitis and only received a pre-treatment vehicle; Group B was subjected to TNSB-induced colitis and only received a pre-treatment with vehicle; Group C was not subjected to TNSB-induced colitis but received a pre-treatment of 5 mg/kg of a compound disclosed in Table VIII; Group D was subjected to TNSB-induced colitis and received a pre-treatment with 0.3 mg/kg of a compound disclosed in Table VIII; Group E was subjected to TNSB-induced colitis and received a pre-treatment with 1 mg/kg of a compound disclosed in Table VIII; and Group F was subjected to TNSB-induced colitis and received a pre-treatment with 5 mg/kg of a compound disclosed in Table VIII. As evidenced by these data, for animals pre-treated with a compound disclosed in Table VIII there was no change in hematocrit levels.

Xenograft Model: Mouse Colon 26 Carcinoma

Nude mice (Harlan Sprague Dawley, Inc., Indianapolis Ind.) were inoculated subcutaneously in the right flank with 0.1 mL of a 0.9% NaCl mixture containing a suspension of Mouse Colon 26 tumor cells (approx. $1 \times 10^6$ cells/mouse). Nine days following inoculation, the resulting tumors were measured using vernier calipers and tumor weight was calculated using the formula:

$$\text{Tumor weight (mg)} = \frac{\text{width (mm)}^2 \times \text{length mm})}{2}$$

wherein the width can be taken as the smallest diameter and the length the largest diameter of the tumor. Twenty-four mice having tumors in the range of 75-144 mg were then selected. The mice were randomized into three groups of eight mice each. The body weight of each animal was at taken when the mice were pair-matched on day one and recorded. Body weights were then taken twice weekly thereafter in conjunction with tumor measurements. See Britten C. D. et al., "Enhanced antitumor activity of 6-hydroxymethyl-acylfulvene in combination with irinotecan and 5-fluorouracil in the HT29 human colon tumor xenograft model." *Cancer Res* 1999; 59:1049-53, incorporated by reference herein in its entirety.

Beginning on Day 1, 5-fluorouracil (5-FU) was administered intravenously once daily for five days to each animal (Groups 1-3). Starting on Day 2, a compound disclosed in Table VIII was administered subcutaneously every other day for 3 doses (Days 2, 4, and 6) at doses of either 5 mg/kg (Group 2) or 10 mg/kg (Group 3). The study terminated on Day 27 when the control group tumor weight reached an average of 1926.9 mg. The mice were sacrificed and the tumors were collected from all mice. All animals survived the full course of this study. The actual weight of each tumor was recorded. Table IX below shows the results of this study.

TABLE IX

| Group | Drug | Dose (mg/kg) | Route | Tumor Wgt. | Tumor Growth Inhibition | Mean Tumor shrinkage |
|---|---|---|---|---|---|---|
| 1 | 5-FU | 10 | IV | 1926.9 ± 284.9 | — | — |
| 2 | 5-FU inhibitor* | 10 5 | IV SC | 1398.0 ± 384.6 | 18.5 (7/8) | 52.0 (1/8) |
| 3 | 5-FU inhibitor* | 10 10 | IV SC | 1118.2 ± 378.9 | 24.3 (6/8) | 87.5 (1/8) |

*The inhibitor is a compound disclosed in Table VIII

As evidenced in Table IX overall tumor weight was significantly reduced in both groups receiving a compound disclosed in Table VIII in combination with 5-fluorouracil than Group 1 which received 5-fluorouracil alone. Mean tumor shrinkage for animals in Group 3 was 87% with one animal having complete shrinkage of the tumor.

Kits

Also disclosed are kits comprising the HIF-1α prolyl hydroxylase inhibitors be delivered into a human or a mammal suffering from or diagnosed with one or more diseases or conditions affecting intestinal epithelial tissue, inter alia, Crohn's disease, ulcerative colitis, collagenous colitis, lymphocytic colitis, ischemic colitis, diversion colitis, Behçet's syndrome, and indeterminate colitis. The kits can comprise one or more packaged unit doses of a composition comprising one or more HIF-1α prolyl hydroxylase inhibitors to be delivered into a human or mammal. The units dosage ampules or multidose containers, in which the HIF-1α prolyl hydroxylase inhibitors to be delivered are packaged prior to use, can comprise an hermetically sealed container enclosing an amount of polynucleotide or solution containing a substance suitable for a pharmaceutically effective dose thereof, or multiples of an effective dose. The HIF-1α prolyl hydroxylase inhibitor can be packaged as a sterile formulation, and the hermetically sealed container is designed to preserve sterility of the formulation until use.

The disclosed HIF-1α prolyl hydroxylase inhibitors can also be present in liquids, emulsions, or suspensions for delivery of active therapeutic agents in aerosol form to cavities of the body such as the nose, throat, or bronchial passages. The ratio of HIF-1α prolyl hydroxylase inhibitors to the other compounding agents in these preparations will vary as the dosage form requires.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the HIF-1α prolyl hydroxylase inhibitor in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

When the HIF-1α prolyl hydroxylase inhibitors are to be delivered into a mammal, the mammal can be a non-human primate, horse, pig, rabbit, dog, sheep, goat, cow, cat, guinea pig or rodent. The terms human and mammal do not denote a particular age or sex. Thus, adult and newborn subjects, as well as fetuses, whether male or female, are intended to be covered. A patient, subject, human or mammal refers to a subject afflicted with a disease or disorder. The term "patient" includes human and veterinary subjects.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure

What is claimed is:

1. A method for treating a subject for an inflammatory epithelial disease, comprising administering to a subject an effective amount of one or more compounds having the formula:

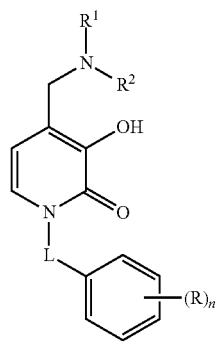

wherein L is chosen from $CH_2$ or $SO_2$;
R represents from 0 to 5 substitutions for hydrogen;
the index n is an integer from 0 to 5;
$R^1$ and $R^2$ are each independently chosen from:
  i) hydrogen;
  ii) substituted or unsubstituted $C_1$-$C_{10}$ linear, branched, or cyclic alkyl;
  iii) substituted or unsubstituted $C_2$-$C_{10}$ linear, branched, or cyclic alkenyl;
  iv) substituted or unsubstituted $C_2$-$C_{10}$ linear or branched alkynyl;
  v) substituted or unsubstituted $C_6$ or $C_{10}$ aryl;
  vi) substituted or unsubstituted $C_1$-$C_9$ heterocyclic;
  vii) substituted or unsubstituted $C_1$-$C_9$ heteroaryl; or
  viii) $R^1$ and $R^2$ can be taken together to form a substituted or unsubstituted heterocyclic or substituted or unsubstituted heteroaryl ring having from form 2 to 20 carbon atoms and from 1 to 7 heteroatoms; or
a pharmaceutically acceptable salt thereof.

2. The method according to claim 1, wherein the one or more compounds are in the form of a pharmaceutically acceptable salt chosen from hydrochloride salt, hydrogen sulfate salt, sulfate salt, p-toluenesulfonyl salt, methansulfonyl salt and mixtures thereof.

3. The method according to claim 1, wherein the inflammatory epithelial disease is a disease affecting intestinal epithelial tissue.

4. The method according to claim 3, wherein the disease is Crohn's disease.

5. The method according to claim 3, wherein the disease is ulcerative colitis.

6. The method according to claim 3, wherein the disease is collagenous colitis.

7. The method according to claim 3, wherein the disease is lymphocytic colitis.

8. The method according to claim 3, wherein the disease is ischemic colitis.

9. The method according to claim 3, wherein the disease is diversion colitis.

10. The method according to claim 3, wherein the disease is Behçet's syndrome.

11. The method according to claim 3, wherein the disease is indeterminate colitis.

12. The method according to claim 1, wherein the inflammatory epithelial disease is chosen from a disease affecting the respiratory tract, mucosa, skin, GI tract, lining of major organs and endocrine glands, vascular tissue, and combinations thereof.

13. The method according to claim 1, wherein L is $CH_2$.

14. The method according to claim 1, wherein L is $SO_2$.

15. The method according to claim 1, wherein each R is a substitution for hydrogen independently chosen from:
  i) substituted or unsubstituted $C_1$-$C_{12}$ linear, $C_3$-$C_{12}$ branched, or $C_3$-$C_{12}$ cyclic alkyl;
  ii) substituted or unsubstituted $C_1$-$C_{12}$ linear, $C_3$-$C_{12}$ branched, or $C_3$-$C_{12}$ cyclic alkenyl;
  iii) substituted or unsubstituted $C_2$-$C_{12}$ linear or $C_3$-$C_{12}$ branched alkynyl;
  iv) $C_6$ or $C_{10}$ substituted or unsubstituted aryl;
  v) $C_1$-$C_9$ substituted or unsubstituted heterocyclic;
  vi) $C_1$-$C_{11}$ substituted or unsubstituted heteroaryl;
  vii) halogen;
  viii) —[C($R^{23a}$)($R^{23b}$)]$_x$O$R^{10}$;
    $R^{10}$ is chosen from:
    a) —H;
    b) substituted or unsubstituted $C_1$-$C_{12}$ linear, $C_3$-$C_{12}$ branched, or $C_3$-$C_{12}$ cyclic alkyl;
    c) $C_6$ or $C_{10}$ substituted or unsubstituted aryl or alkylenearyl;
    d) $C_1$-$C_9$ substituted or unsubstituted heterocyclic;
    e) $C_1$-$C_{11}$ substituted or unsubstituted heteroaryl;
  ix) —[C($R^{23a}$)($R^{23b}$)]$_x$N($R^{11a}$)($R^{11b}$);
    $R^{11a}$ and $R^{11b}$ are each independently chosen from:
    a) —H;
    b) —O$R^{12}$;
      $R^{12}$ is hydrogen or $C_1$-$C_4$ linear alkyl;
    c) substituted or unsubstituted $C_1$-$C_{12}$ linear, $C_3$-$C_{12}$ branched, or $C_3$-$C_{12}$ cyclic alkyl;
    d) $C_6$ or $C_{10}$ substituted or unsubstituted aryl;
    e) $C_1$-$C_9$ substituted or unsubstituted heterocyclic;
    f) $C_1$-$C_{11}$ substituted or unsubstituted heteroaryl; or
    g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;
  x) —[C($R^{23a}$)($R^{23b}$)]$_x$C(O)$R^{13}$;
    $R^{13}$ is:
    a) substituted or unsubstituted $C_1$-$C_{12}$ linear, $C_3$-$C_{12}$ branched, or $C_3$-$C_{12}$ cyclic alkyl;
    b) —O$R^{14}$;
      $R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
    c) —N($R^{15a}$)($R^{15b}$);
      $R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;
  xi) —[C($R^{23a}$)($R^{23b}$)]$_x$OC(O)$R^{16}$;
    $R^{16}$ is:
    a) substituted or unsubstituted $C_1$-$C_{12}$ linear, $C_3$-$C_{12}$ branched, or $C_3$-$C_{12}$ cyclic alkyl;
    b) —N($R^{17a}$)($R^{17b}$)
      $R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;
  xii) —[C($R^{23a}$)($R^{23b}$)]$_x$N$R^{18}$C(O)$R^{19}$;
    $R^{18}$ is:
    a) —H; or
    b) substituted or unsubstituted $C_1$-$C_4$ linear, $C_3$-$C_4$ branched, or $C_3$-$C_4$ cyclic alkyl;
    $R^{19}$ is:
    a) substituted or unsubstituted $C_1$-$C_{12}$ linear, $C_3$-$C_{12}$ branched, or $C_3$-$C_{12}$ cyclic alkyl;
    b) —N($R^{20a}$)($R^{20b}$);
      $R^{20a}$ and $R^{20b}$ are each independently hydrogen, substituted or unsubstituted $C_1$-$C_4$ linear or $C_2$-$C_4$ branched alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

xiii) —[C($R^{23a}$)($R^{23b}$)]$_x$CN;

xiv) —[C($R^{23a}$)($R^{23b}$)]$_x$NO$_2$;

xv) —[C($R^{23a}$)($R^{23b}$)]$_x$R$^{21}$;

$R^{21}$ is $C_1$-$C_{10}$ linear, branched, or cyclic alkyl substituted by from 1 to 21 halogen atoms chosen from —F, —Cl, —Br, or —I;

xvi) —[C($R^{23a}$)($R^{23b}$)]$_x$SO$_2$R$^{22}$;

$R^{22}$ is hydrogen, hydroxyl, substituted or unsubstituted $C_1$-$C_4$ linear or $C_2$-$C_4$ branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl;

$R^{23a}$ and $R^{23b}$ are each independently hydrogen or $C_1$-$C_4$ alkyl; and the index x is an integer from 0 to 5.

16. The method according to claim 1, wherein $R^1$ and $R^2$ are taken together to form a 5-member substituted or unsubstituted $C_1$-$C_4$ heterocyclic or a substituted or unsubstituted $C_1$-$C_4$ heteroaryl ring.

17. The method according to claim 16, wherein $R^1$ and $R^2$ are taken together to form a ring having the formula:

i)
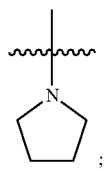

ii)
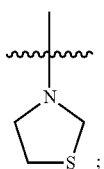

iii)
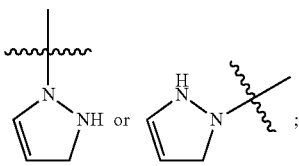

iv)
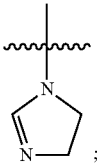

v)
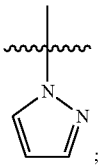

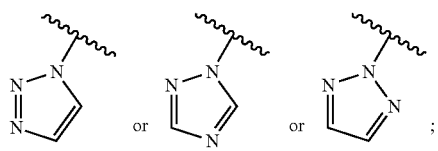

vi)
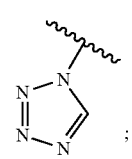

vii)
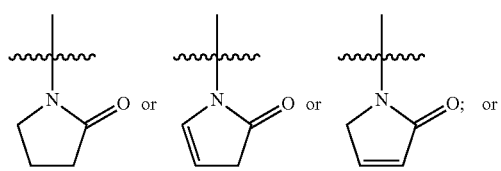

viii)
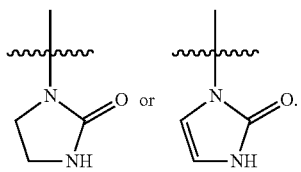

18. The method according to claim 1, wherein $R^1$ and $R^2$ are taken together to form a substituted or unsubstituted $C_4$-$C_{11}$ heterocyclic or a substituted or unsubstituted $C_4$-$C_{11}$ heteroaryl ring.

19. The method according to claim 18, wherein $R^1$ and $R^2$ are taken together to form a ring having the formula:

i)
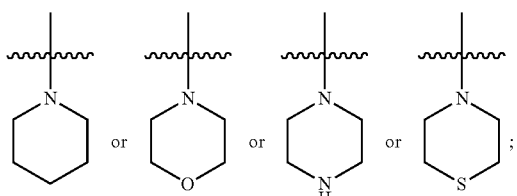

ii)
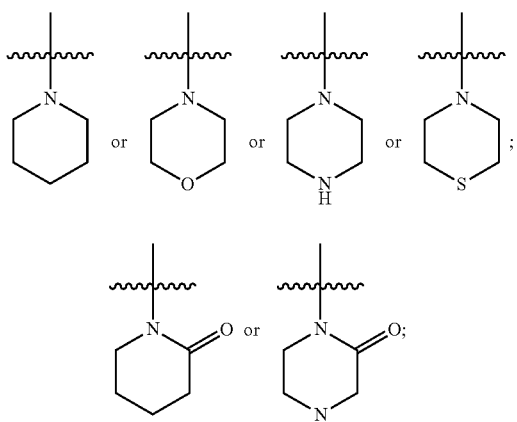

iii)
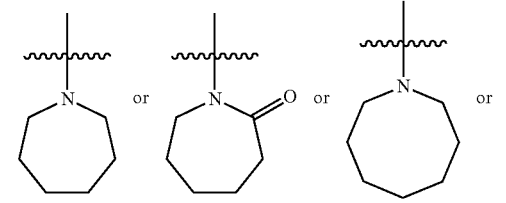

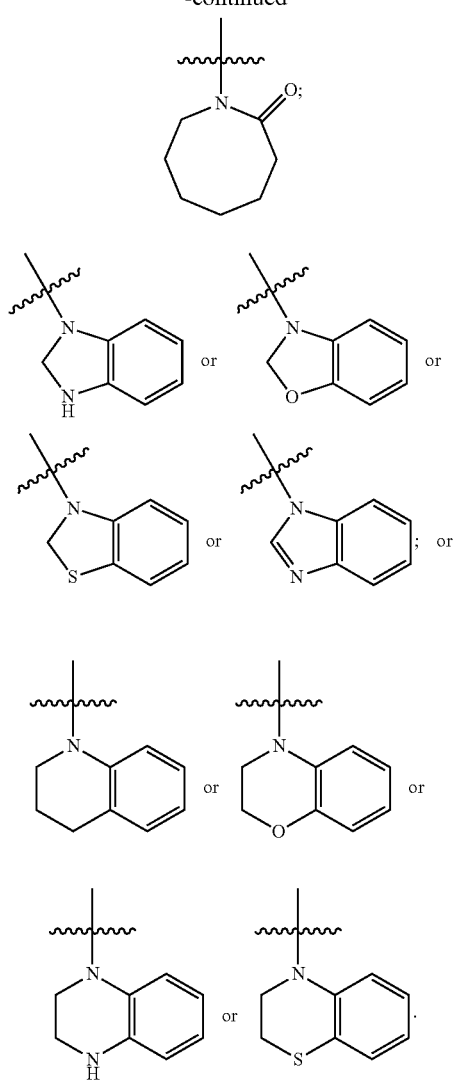

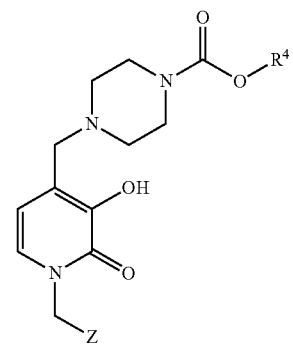

20. The method according to claim 1, wherein $R^1$ and $R^2$ are taken together to form a ring chosen from pyrrolidin-1-yl, 3-hydroxypyrrolidin-1-yl, 2-(pyrdin-2-yl)pyrrolidin-1-yl, 2-methylcarboxypyrrolidin-1-yl, 2-(methoxymethyl)pyrrolidin-1-yl, thiazolidin-3-yl, 1H-imidazol-1-yl, piperidin-1-yl, 4-benzylpiperidin-1-yl, 1,4'-bipiperidinyl-1'-yl, piperazin-1-yl, 4-benzylpiperazin-1-yl, 4-(2-methoxyphenyl)-piperazin-1-ylmethyl, 4-(6-chloropyridazin-3-yl)piperazin-1-yl, 1,4-dioxa-8-azaspiro[4,5]dec-8-yl, morpholin-4-yl, thiomorpholin-4-yl, azepan-1-yl, azocan-1-yl, and 3,4-dihydroquinolin-1(2H)-yl.

21. The method according to claim 1, wherein $R^2$ is hydrogen and $R^1$ is chosen from benzyl, 4-methoxybenzyl, 4-fluorobenzyl, 4-chlorobenzyl, 4-methylbenzyl, 2-(pyridin-2-yl)ethyl, [1,3]dioxolan-2-ylmethyl, tetrahydrofuran-2-ylmethyl, 2-methoxyethyl, 1-hydroxy-2-methylpropan-2-yl, pyridin-4-ylmethyl, furan-2-ylmethyl, 2-(methylthio)ethyl, 1-phenylethyl, 3-imidazol-1-ylpropyl, cycloheptyl, 4-methylcyclohexyl, 1-benzylpiperidin-4-yl, azepan-2-on-3-yl, and 1-benzyl-pyrrolidin-3-yl.

22. The method according to claim 1, wherein the one or more compounds have the formula:

wherein Z is phenyl substituted with from 1 to 5 halogens chosen from fluorine and chlorine;
$R^4$ is $C_1$-$C_4$ linear alkyl or $C_3$-$C_4$ branched alkyl; or
a pharmaceutically acceptable salt thereof.

23. The method according to claim 22, wherein $R^4$ is methyl.

24. The method according to claim 22, wherein $R^4$ is ethyl.

25. The method according to claim 22, wherein $R^4$ is tert-butyl.

26. The method according to claim 22, wherein Z is 4-chlorophenyl.

27. The method according to claim 22, wherein Z is chosen from 2-chlorophenyl, 3-chlorophenyl, 2-fluorophenyl, 3-fluorophenyl, or 4-fluorophenyl.

28. The method according to claim 22, wherein Z is chosen from 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, and 2,6-dichlorophenyl.

29. The method according to claim 1, wherein the one or more compounds is tert-butyl 4-{[1-(4-chlorobenzyl)-3-hydroxy-2-oxo-1,2-dihydropyridin-4-yl]methyl}-piperazine-1-carboxylate or a pharmaceutically acceptable salt chosen from hydrochloride salt, hydrogen sulfate salt, sulfate salt, p-toluenesulfonyl salt, methansulfonyl salt and mixtures thereof.

30. The method according to claim 1, wherein the one or more compounds is chosen from:
Methyl 4-{[1-(4-chlorobenzyl)-3-hydroxy-2-oxo-1,2-dihydropyridin-4-yl]methyl}piperazine-1-carboxylate;
Methyl 4-{[1-(3-chlorobenzyl)-3-hydroxy-2-oxo-1,2-dihydropyridin-4-yl]methyl}piperazine-1-carboxylate;
Methyl 4-{[1-(2-chlorobenzyl)-3-hydroxy-2-oxo-1,2-dihydropyridin-4-yl]methyl}piperazine-1-carboxylate;
Ethyl 4-{[1-(4-chlorobenzyl)-3-hydroxy-2-oxo-1,2-dihydropyridin-4-yl]methyl}piperazine-1-carboxylate;
Ethyl 4-{[1-(3-chlorobenzyl)-3-hydroxy-2-oxo-1,2-dihydropyridin-4-yl]methyl}piperazine-1-carboxylate;
Ethyl 4-{[1-(2-chlorobenzyl)-3-hydroxy-2-oxo-1,2-dihydropyridin-4-yl]methyl}piperazine-1-carboxylate;
tert-Butyl 4-{[1-(3-chlorobenzyl)-3-hydroxy-2-oxo-1,2-dihydropyridin-4-yl]methyl}piperazine-1-carboxylate;
tert-Butyl 4-{[1-(2-chlorobenzyl)-3-hydroxy-2-oxo-1,2-dihydropyridin-4-yl]methyl}piperazine-1-carboxylate;
Methyl 4-{[1-(4-fluorobenzyl)-3-hydroxy-2-oxo-1,2-dihydropyridin-4-yl]methyl}piperazine-1-carboxylate;
Methyl 4-{[1-(3-fluorobenzyl)-3-hydroxy-2-oxo-1,2-dihydropyridin-4-yl]methyl}piperazine-1-carboxylate;
Methyl 4-{[1-(2-fluorobenzyl)-3-hydroxy-2-oxo-1,2-dihydropyridin-4-yl]methyl}piperazine-1-carboxylate;
Ethyl 4-{[1-(4-fluorobenzyl)-3-hydroxy-2-oxo-1,2-dihydropyridin-4-yl]methyl}piperazine-1-carboxylate;

Ethyl 4-{([1-(3-fluorobenzyl)-3-hydroxy-2-oxo-1,2-dihydropyridin-4-yl]methyl}piperazine-1-carboxylate;
Ethyl 4-{[1-(2-fluorobenzyl)-3-hydroxy-2-oxo-1,2-dihydropyridin-4-yl]methyl}piperazine-1-carboxylate;
tert-Butyl 4-{[1-(4-fluorobenzyl)-3-hydroxy-2-oxo-1,2-dihydropyridin-4-yl]methyl}piperazine-1-carboxylate;
tert-Butyl 4-{[1-(3-fluorobenzyl)-3-hydroxy-2-oxo-1,2-dihydropyridin-4-yl]methyl}piperazine-1-carboxylate; and
tert-Butyl 4-{[1-(2-fluorobenzyl)-3-hydroxy-2-oxo-1,2-dihydropyridin-4-yl]methyl}piperazine-1-carboxylate.

31. A composition for treating a subject for an inflammatory epithelial disease, comprising
a) an effective amount of one or more compounds having the formula:

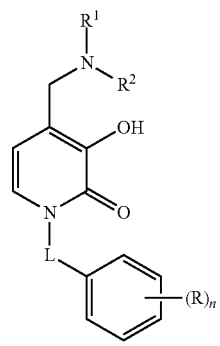

wherein L is chosen from $CH_2$ or $SO_2$;
R represents from 0 to 5 substitutions for hydrogen;
the index n is an integer from 0 to 5;
$R^1$ and $R^2$ are each independently chosen from:
i) hydrogen;
ii) substituted or unsubstituted $C_1$-$C_{10}$ linear, branched, or cyclic alkyl;
iii) substituted or unsubstituted $C_2$-$C_{10}$ linear, branched, or cyclic alkenyl;
iv) substituted or unsubstituted $C_2$-$C_{10}$ linear or branched alkynyl;
v) substituted or unsubstituted $C_6$ or $C_{10}$ aryl;
vi) substituted or unsubstituted $C_1$-$C_9$ heterocyclic;
vii) substituted or unsubstituted $C_1$-$C_9$ heteroaryl; or
i) $R^1$ and $R^2$ can be taken together to form a substituted or unsubstituted heterocyclic or substituted or unsubstituted heteroaryl ring having from form 2 to 20 carbon atoms and from 1 to 7 heteroatoms;
$R^4$ is $C_1$-$C_4$ linear or $C_3$-$C_4$ branched alkyl; or
a pharmaceutically acceptable salt thereof; and
b) one or more excipients.

32. The composition according to claim 31, wherein the one or more compounds are in the form of a pharmaceutically acceptable salt chosen from hydrochloride salt, hydrogen sulfate salt, sulfate salt, p-toluenesulfonyl salt, methansulfonyl salt and mixtures thereof.

33. The composition according to claim 31, wherein the one or more compounds have the formula:

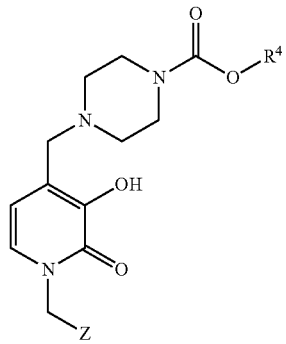

wherein Z is phenyl substituted with from 1 to 5 halogens chosen from fluorine and chlorine;
$R^4$ is $C_1$-$C_4$ linear alkyl or $C_3$-$C_4$ branched alkyl; or
a pharmaceutically acceptable salt thereof.

34. The composition according to claim 33, wherein $R^4$ is methyl.

35. The composition according to claim 33, wherein $R^4$ is ethyl.

36. The composition according to claim 33, wherein $R^4$ is tert-butyl.

37. The composition according to claim 33, wherein Z is 4-chlorophenyl.

38. The composition according to claim 33, wherein Z is chosen from 2-chlorophenyl, 3-chlorophenyl, 2-fluorophenyl, 3-fluorophenyl, or 4-fluorophenyl.

39. The composition according to claim 31, wherein the one or more compounds is tert-butyl 4-{[1-(4-chlorobenzyl)-3-hydroxy-2-oxo-1,2-dihydropyridin-4-yl]methyl}-piperazine-1-carboxylate or a pharmaceutically acceptable salt hydrochloride salt, hydrogen sulfate salt, sulfate salt, p-toluenesulfonyl salt, methansulfonyl salt and mixtures thereof.

40. The composition according to claim 31, further comprising one or more chemotherapeutic compounds.

41. The composition according to claim 40, wherein the one or more chemotherapeutic compounds are chosen from 6-hydroxymethylacylfulvene, cyclophosphamide, dacarbazine, carmustine, doxorubicin, and methotrexate.

42. The composition according to claim 31, wherein the inflammatory epithelial disease is chosen from Crohn's disease, ulcerative colitis, collagenous colitis, lymphocytic colitis, ischemic colitis, diversion colitis, Behçet's syndrome, and indeterminate colitis.

* * * * *